(12) United States Patent
Cheng et al.

(10) Patent No.: US 10,544,092 B2
(45) Date of Patent: Jan. 28, 2020

(54) MALONONITRILE OXIME ETHER COMPOUND AND USE THEREOF

(71) Applicant: SHENYANG SINOCHEM AGROCHEMICALS R&D CO., LTD., Liaoning (CN)

(72) Inventors: Xueming Cheng, Liaoning (CN); Lixin Zhang, Liaoning (CN); Liang Chen, Liaoning (CN); Qin Sun, Liaoning (CN); Junli Liu, Liaoning (CN); Zhinian Li, Liaoning (CN); Jie Zhao, Liaoning (CN); Jingbo Xu, Liaoning (CN); Hongfei Wu, Liaoning (CN)

(73) Assignee: SHENYANG SINOCHEM AGROCHEMICALS R&D CO., LTD., Liaoning (CN)

( * ) Notice: Subject to any disclaimer, the term of this patent is extended or adjusted under 35 U.S.C. 154(b) by 0 days.

(21) Appl. No.: 16/060,057

(22) PCT Filed: Dec. 22, 2016

(86) PCT No.: PCT/CN2016/111411
§ 371 (c)(1),
(2) Date: Jun. 7, 2018

(87) PCT Pub. No.: WO2017/107939
PCT Pub. Date: Jun. 29, 2017

(65) Prior Publication Data
US 2018/0362450 A1 Dec. 20, 2018

(30) Foreign Application Priority Data
Dec. 25, 2015 (CN) .......................... 2015 1 0998120

(51) Int. Cl.
| | | |
|---|---|---|
| *A01N 33/24* | (2006.01) | |
| *A01N 43/78* | (2006.01) | |
| *C07C 255/64* | (2006.01) | |
| *C07C 251/58* | (2006.01) | |
| *C07C 251/56* | (2006.01) | |
| *C07C 251/54* | (2006.01) | |
| *A01N 43/40* | (2006.01) | |
| *A01N 43/42* | (2006.01) | |
| *A01N 43/56* | (2006.01) | |
| *C07D 213/61* | (2006.01) | |
| *C07D 215/14* | (2006.01) | |
| *C07D 231/12* | (2006.01) | |
| *C07D 231/14* | (2006.01) | |
| *C07D 277/28* | (2006.01) | |
| *C07D 277/64* | (2006.01) | |

(52) U.S. Cl.
CPC ............ *C07C 255/64* (2013.01); *A01N 33/24* (2013.01); *A01N 43/40* (2013.01); *A01N 43/42* (2013.01); *A01N 43/56* (2013.01); *A01N 43/78* (2013.01); *C07D 213/61* (2013.01); *C07D 215/14* (2013.01); *C07D 231/12* (2013.01); *C07D 231/14* (2013.01); *C07D 277/28* (2013.01); *C07D 277/64* (2013.01)

(58) Field of Classification Search
CPC ...... A01N 33/24; A01N 43/78; C07C 255/64; C07C 251/58; C07C 251/56; C07C 251/54
USPC .......................... 514/640; 564/254, 256, 265
See application file for complete search history.

(56) References Cited

U.S. PATENT DOCUMENTS

| | | | |
|---|---|---|---|
| 5,104,872 | A | 4/1992 | Tsubata et al. |
| 5,194,662 | A | 3/1993 | Brand et al. |
| 5,221,691 | A | 6/1993 | Clough et al. |
| 5,342,837 | A | 8/1994 | Clough et al. |
| 5,393,920 | A | 2/1995 | Benoit et al. |
| 5,530,156 | A | 6/1996 | Benoit et al. |
| 5,965,613 | A | 10/1999 | Insenring et al. |
| 6,211,240 | B1 | 4/2001 | Zurflüh |
| 6,288,071 | B1 | 9/2001 | Szczepanski et al. |
| 6,342,633 | B1 | 1/2002 | Zurflüh |
| 8,722,678 | B2 | 5/2014 | Hanagan et al. |

(Continued)

FOREIGN PATENT DOCUMENTS

| | | |
|---|---|---|
| CN | 1065658 | 10/1992 |
| CN | 1024662 C | 5/1994 |

(Continued)

OTHER PUBLICATIONS

Office Action received in Chinese Patent Application No. 201611199611.9 dated Mar. 21, 2018 (4 pages in Chinese).
Search Report received in Chinese Patent Application No. 201611199611.9 dated Sep. 14, 2018 (2 pages).
Office Action received in Chinese Patent Application No. 201611199611.9 dated Sep. 14, 2018 (4 pages in Chinese with machine translation).

(Continued)

*Primary Examiner* — Matthew P Coughlin
*Assistant Examiner* — Sagar Patel
(74) *Attorney, Agent, or Firm* — Smith, Gambrell & Russell, LLP

(57) ABSTRACT

Disclosed is a malononitrile oxime ether compound having a novel structure as shown in the general formula I. Respective substituents in the general formula I as defined in the specification.

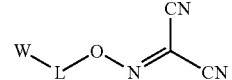

The compound of the general formula I exhibits an excellent microbicidal activity, and can effectively prevent and treat plant diseases caused by bacteria and fungi. Also provided is a use of the compound of the general formula I as a microbicide in the agricultural and other fields.

13 Claims, No Drawings

(56) References Cited

U.S. PATENT DOCUMENTS

| | | |
|---|---|---|
| 2009/0306162 A1 | 12/2009 | Vandenberg |
| 2011/0144173 A1 | 6/2011 | Vandenberg |
| 2011/0224258 A1 | 9/2011 | Pasteris |
| 2013/0096098 A1 | 4/2013 | Gerasimchuk et al. |

FOREIGN PATENT DOCUMENTS

| | | | |
|---|---|---|---|
| CN | 1109686 A | 10/1995 | |
| CN | 1250046 A | 4/2000 | |
| CN | 102227423 A | 10/2011 | |
| CN | 102933577 A | 2/2013 | |
| CN | 103804321 A | 5/2014 | |
| EP | 0370629 A1 | 5/1990 | |
| EP | 0411409 A1 | 2/1991 | |
| EP | 0472300 A2 | 2/1992 | |
| EP | 0564984 A2 | 10/1993 | |
| EP | 0621864 B1 | 12/1996 | |
| EP | 0912499 B1 | 12/2001 | |
| EP | 1940230 B1 | 9/2011 | |
| JP | H04-187667 A | 7/1992 | |
| WO | 97/00859 | 1/1997 | |
| WO | 97/07099 A1 | 2/1997 | |
| WO | 99/06380 A1 | 2/1999 | |
| WO | 99/31070 A1 | 6/1999 | |
| WO | 2008/139481 A2 | 11/2008 | |
| WO | WO-2010065579 A2 * | 6/2010 | ............ A01N 43/78 |
| WO | 2014/179144 A1 | 11/2014 | |

OTHER PUBLICATIONS

Search Report received in Chinese Patent Application No. 201611199611.9 dated Dec. 19, 2018 (2 pages).

Search Report received in Chinese Patent Application No. 201611199611.9 dated Dec. 25, 2018 (1 page).

Search Report received in Chinese Patent Application No. 201611199611.9 dated Mar. 1, 2019 (1 page).

Khattab, S., et al. Oxime Carbonates: Novel Reagents for the Introduction of Fmoc and Alloc Protecting Groups, Free of Side Reactions. European Journal of Organic Chemistry. 2010. pp. 3275-3280.

International Search Report for PCT/CN2016/111411, dated Mar. 29, 2017 in English and Chineses Language.

Asian Journal of of Chemistry, "Synthesis of 2,3,4,5-Tetraphenylfuran,-thiophene and -pyrrole from Toluene", Meliha Burcu Gürdere, et al., vol. 20, No. 2 (2008), pp. 1425-1430.

European Journal of Inorganic Chemistry, "Well-Defined Silica-Supported Zirconium-Benzyl Cationic Species: Improved Heterogenization of Single-Site Polymerization Catalysts", Nicolas Popoff, et al., 2014, pp. 888-895.

Journal of Chemical Society of Pakistan, "Spectrophotometric Determination of $pK_a$'s of 1-Hydroxybenzotriazole and Oxime Derivatives in 95% Acetonitrile-Water", Magda Fouad Fathalla, et al., vol. 33, No. 3, 2011, pp. 324-332.

\* cited by examiner

MALONONITRILE OXIME ETHER COMPOUND AND USE THEREOF

FIELD OF THE INVENTION

The invention relates to fungicide and bactericide in agriculture, Specifically to a class of malononitrile oxime ether compounds and use thereof.

BACKGROUND OF THE INVENTION

The oxime ether derivatives relate to a class of compounds with broad-spectrum biological activity which are widely used for insecticide, herbicide and fungicide in pesticide. Since the first commercial oxime ether fungicide (cymoxanil) was developed by DuPont in 1974, new commercial pesticides are constantly developed, such as pyrifenox, kresoxim-methyl, orysastrobin, etc. Because of their characteristics of high efficiency, low toxicity and low residue, oxime ethers have always been the hotspot of research in many famous companies.

Neither the preparation of malononitrile oxime ether compounds represented by the structure of formula I, nor their fungicidal and bactericidal activities is described in state of the arts.

SUMMARY OF THE INVENTION

The purpose of the present disclosure is to provide a kind of novel malononitrile oxime ether compounds, which can be used to control disease in agricultural or other fields.

In order to achieve the purpose above, the detailed descriptions of the invention are as follows:

The present disclosure provides a kind of malononitrile oxime ether compounds as represented by the structure of formula I:

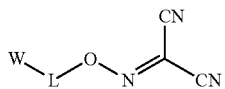

I wherein:
L represents a divalent group selected in the list consisting of

—$(CR^1R^2)_n$—   —$(CR^1R^2)_m$—$CH_2$—$(C=O)$—$CH_2$—$(CR^1R^2)_p$—
—$(CR^1R^2)_m$—$(CR^1=CR^2)$—$(CR^1R^2)_p$—   —$(CR^1R^2)_m$—$(C=O)$—O—$CH_2$—$(CR^1R^2)_p$—
—$(CR^1R^2)_m$—$(C\equiv C)$—$(CR^1R^2)_p$—   —$(CR^1R^2)_m$—O—$(C=O)$—$CH_2$—$(CR^1R^2)_p$—
—$(CR^1R^2)_m$—O—$CH_2$—$(CR^1R^2)_p$—   —$(CR^1R^2)_m$—$(C=O)$—NH—$CH_2$—$(CR^1R^2)_p$—
—$(CR^1R^2)_m$—NH—$CH_2$—$(CR^1R^2)_p$—   —$(CR^1R^2)_m$—NH—$(C=O)$—$CH_2$—$(CR^1R^2)_p$—
or —$(CR^1R^2)_m$—S—$CH_2$—$(CR^1R^2)_p$—;

n represents 1, 2, 3 or 4;
m and p independently represent 0, 1, 2 or 3;
$R^1$ and $R^2$ are independently selected in the list consisting of hydrogen, halogen, cyano, [$C_1$-$C_4$]-alkyl, [$C_1$-$C_4$]-haloalkyl, [$C_3$-$C_5$]-cycloalkyl, [$C_2$-$C_4$]-alkenyl, [$C_2$-$C_4$]-haloalkenyl, [$C_2$-$C_4$]-alkynyl, [$C_2$-$C_4$]-haloalkynyl, [$C_1$-$C_4$]-alkoxy, [$C_1$-$C_4$]-haloalkoxy, [$C_1$-$C_4$]-alkoxy-[$C_1$-$C_4$]-alkyl, [$C_1$-$C_4$]-alkoxy-[$C_1$-$C_4$]-alkoxy and [$C_1$-$C_4$]-haloalkoxy-[$C_1$-$C_4$]-alkyl;

W is selected from non-substituted or substituted aryl and non-substituted or substituted aromatic heterocycle;

And when L is —$(CR^1R^2)_n$—, $R^1$ and $R^2$ are selected from hydrogen and n is 1, W is not benzene;

The preferred compounds of the general formula I in the present disclosure are:

L represents a divalent group selected in the list consisting of

—$(CR^1R^2)_n$—   —$(CR^1R^2)_m$—$CH_2$—$(C=O)$—$CH_2$—$(CR^1R^2)_p$—
—$(CR^1R^2)_m$—$(CR^1CR^2)$—$(CR^1R^2)_p$—   —$(CR^1R^2)_m$—$(C=O)$—O—$CH_2$—$(CR^1R^2)_p$—
—$(CR^1R^2)_m$—$(C\equiv C)$—$(CR^1R^2)_p$—   —$(CR^1R^2)_m$—O—$(C=O)$—$CH_2$—$(CR^1R^2)_p$—
—$(CR^1R^2)_m$—O—$CH_2$—$(CR^1R^2)_p$—   —$(CR^1R^2)_m$—$(C=O)$—NH—$CH_2$—$(CR^1R^2)_p$—
—$(CR^1R^2)_m$—NH—$CH_2$—$(CR^1R^2)_p$—   —$(CR^1R^2)_m$—NH—$(C=O)$—$CH_2$—$(CR^1R^2)_p$—,
—$(CR^1R^2)_m$—S—$CH_2$—$(CR^1R^2)_p$—;

n represents 1, 2, 3 or 4;
m and p independently represent 0, 1, 2 or 3;
$R^1$ and $R^2$ are selected from hydrogen;
W is selected in the list consisting of $W^1$ to $W^{84}$:

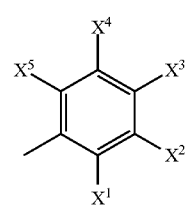

$W^1$

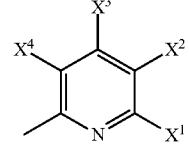

$W^2$

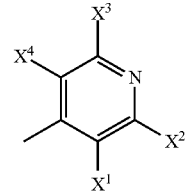

$W^3$

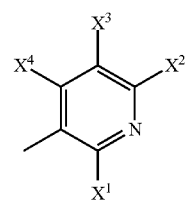

$W^4$

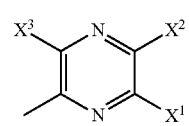

$W^5$

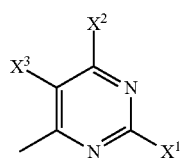 W⁶
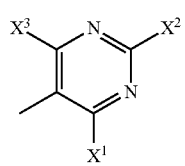 W⁷
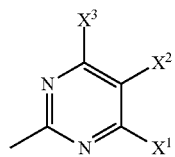 W⁸
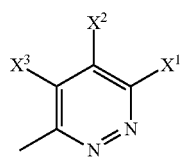 W⁹
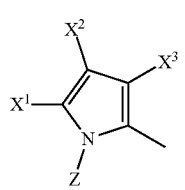 W¹⁰
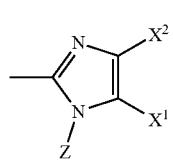 W¹¹
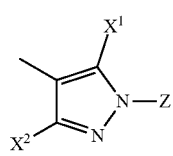 W¹²
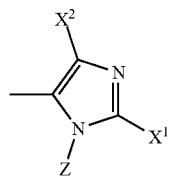 W¹³
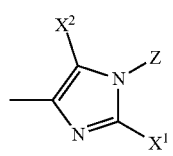 W¹⁴
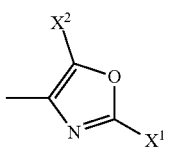 W¹⁵
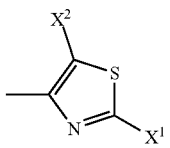 W¹⁶
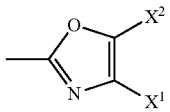 W¹⁷
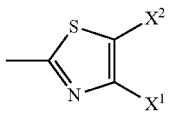 W¹⁸
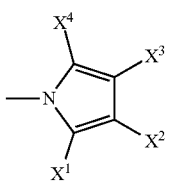 W¹⁹
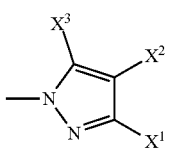 W²⁰
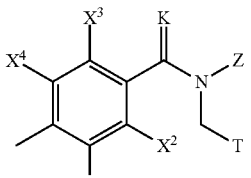 W²¹
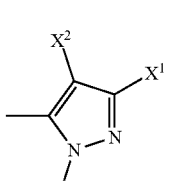 W²²
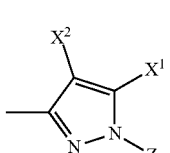 W²³
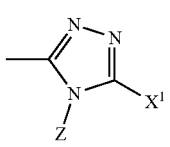 W²⁴

-continued
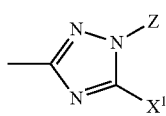
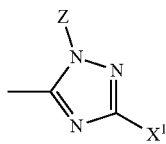
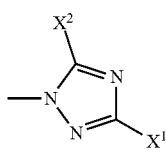
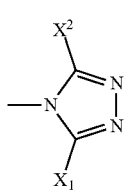
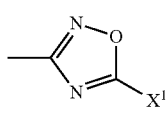
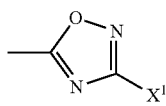
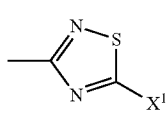
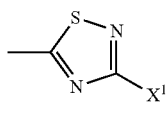
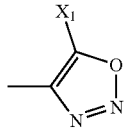
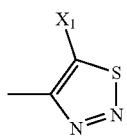
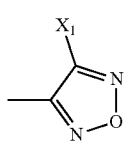
-continued
$W^{25}$
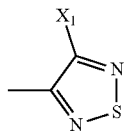
$W^{26}$
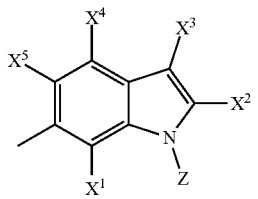
$W^{27}$
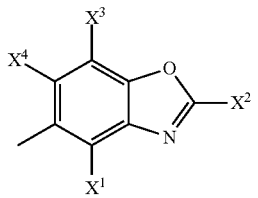
$W^{28}$
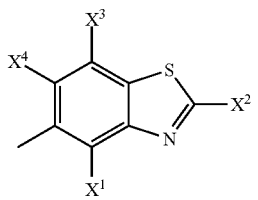
$W^{29}$
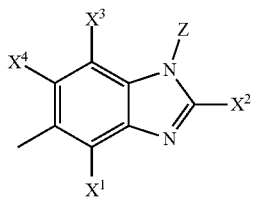
$W^{30}$
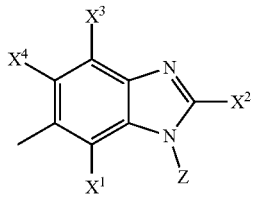
$W^{31}$
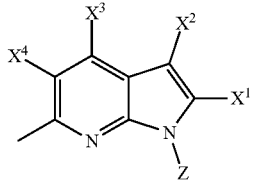
$W^{32}$
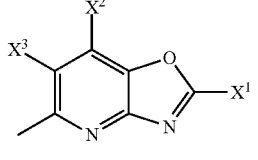
$W^{33}$
$W^{34}$
$W^{35}$
$W^{36}$
$W^{37}$
$W^{38}$
$W^{39}$
$W^{40}$
$W^{41}$
$W^{42}$
$W^{43}$

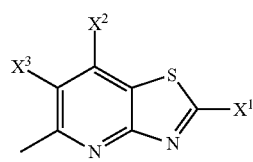
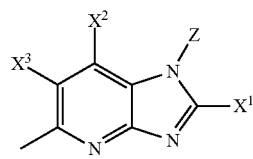
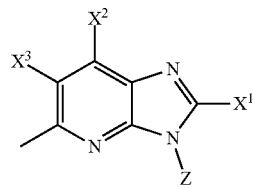
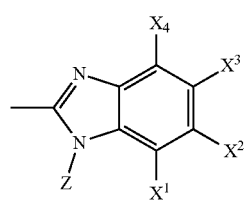
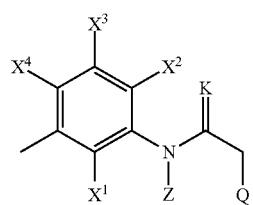
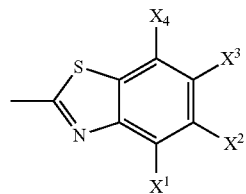
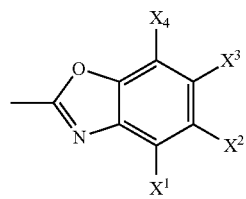
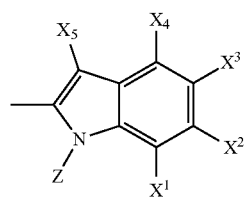
W44
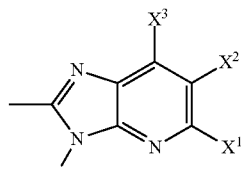
W45
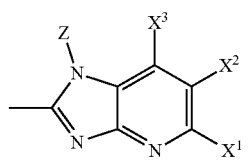
W46
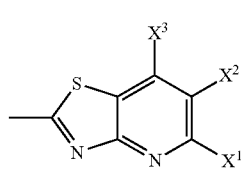
W47
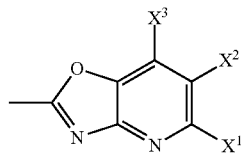
W48
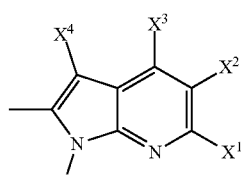
W49
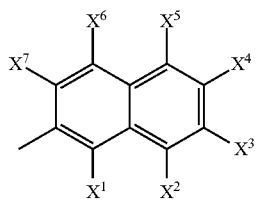
W50
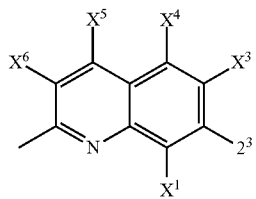
W51
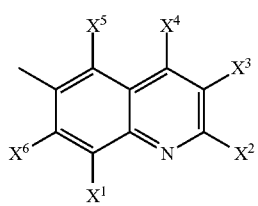
W52
W53
W54
W55
W56
W57
W58
W59

-continued $W^{60}$ $W^{61}$ $W^{62}$ $W^{63}$ $W^{64}$ $W^{65}$ $W^{66}$ $W^{67}$ -continued $W^{68}$ $W^{69}$ $W^{70}$ $W^{71}$ $W^{72}$ $W^{73}$

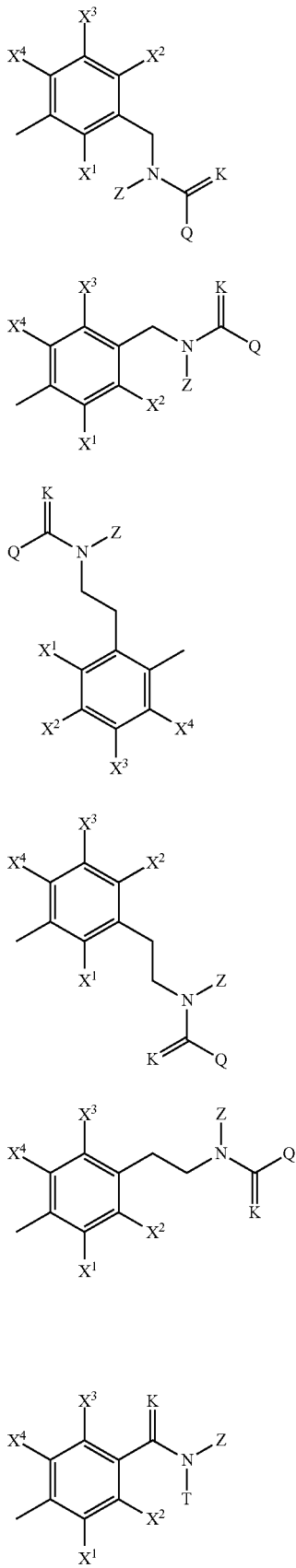
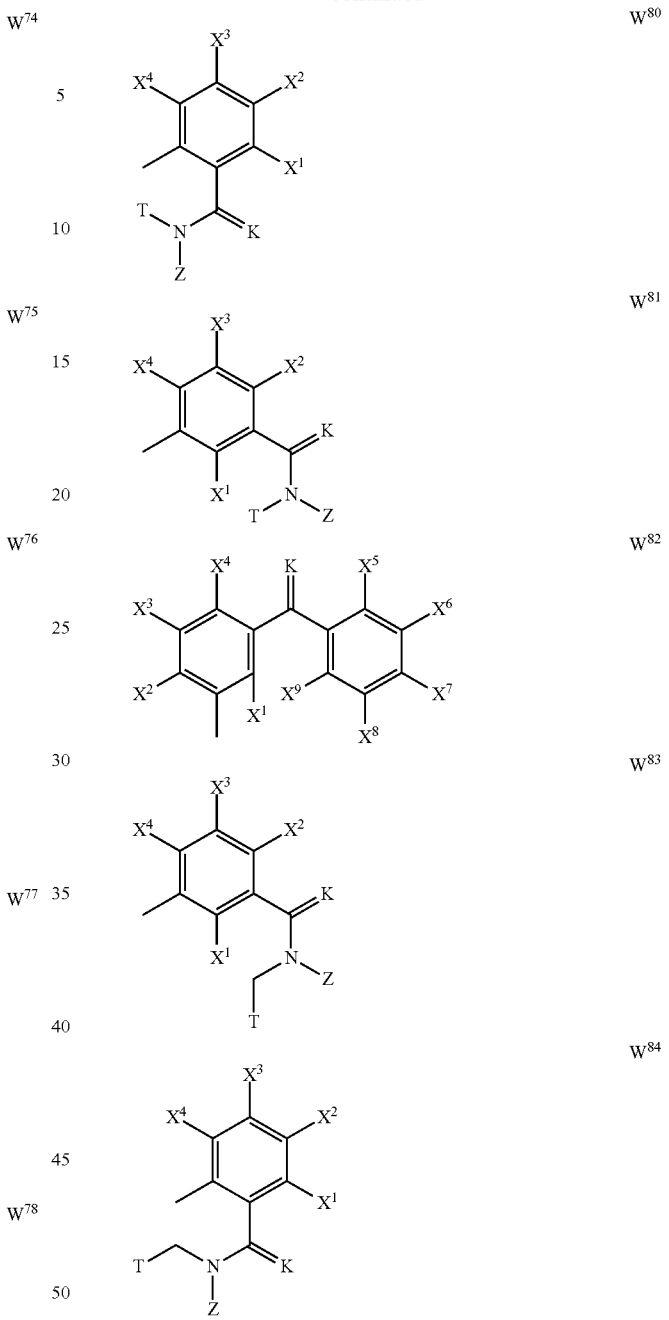

Wherein
$X^1$, $X^2$, $X^4$, $X^5$, $X^6$, $X^7$, $X^8$ and $X^9$ are independently selected in the list consisting of hydrogen halogen, cyano, nitro, —$SF_5$, [$C_1$-$C_8$]-alkyl, [$C_1$-$C_8$]-haloalkyl, [$C_3$-$C_6$]-cycloalkyl, [$C_2$-$C_8$]-alkenyl, [$C_2$-$C_8$]-haloalkenyl, [$C_2$-$C_8$]-alkynyl, [$C_2$-$C_8$]-haloalkynyl, [$C_1$-$C_8$]-alkoxy-[$C_1$-$C_8$]-alkyl, —$OR^3$, —$C(=O)OR^3$, —$N(R^4)S(=O)_2R^5$, —$S(=O)_2NR^3R^5$, —$N(R^4)C(=O)OR^3$, —$CR^4=NOR^3$, —$CH_2ON=C(CN)_2$, —$C(=O)SR^3$, —$C(=S)OR^3$, —$C(=S)SR^3$, —$CR^4=NR^5$, —$CR^4=N-NR^3R^5$, —$OSiR^4R^5R^6$, —$OC(=O)R^4$, —$OC(=O)OR^3$, —$OC(=O)NR^3R^4$, —$OC(=S)NR^3R^4$, —$NR^3R^4$, —$N(R^4)C(=O)NR^3R^5$, —$N(R^4)C(=S)NR^3R^5$, —$N=CR^4R^5$, —$N=C-NR^3R^4$, —$N(R^4)S(=O)_2OR^3$, —$N(R^4)S(=O)OR^3$, —$N(R^4)S(=O)NR^3R^5$, —$N(R^4)S(=O)_2NR^3R^5$, $NR^4C(=O)R^5$, $—SR^3$, $—S(=O)_2R^4$, $—S(=O)R^4$, $—S(=O)OR^3$, $—S(=O)NR^3R^4$, $—S(=O)_2OR^3$, $—S(=O)NR^3R^4$, $—SiR^3R^4R^5$, non-substituted or substituted phenyl, non-substituted or substituted pyridyl, non-substituted or substituted pyrazolyl, non-substituted or substituted thiazolyl, non-substituted or substituted isothiazolyl and non-substituted or substituted thiadiazolyl, wherein substituent group is selected in the list consisting of halogen, cyano, nitro, $[C_1-C_8]$-alkyl, $[C_1-C_8]$-haloalkyl, $[C_1-C_8]$-alkoxy, $[C_1-C_8]$-haloalkoxy, $[C_1-C_8]$-alkylthio or $[C_1-C_8]$-haloalkylthio;

Z is selected in the list consisting of hydrogen, $[C_1-C_8]$-alkyl, $[C_1-C_8]$-haloalkyl, $[C_3-C_6]$-cycloalkyl, $[C_2-C_8]$-alkenyl, $[C_2-C_8]$-haloalkenyl, $[C_2-C_8]$-alkynyl, $[C_2-C_8]$-haloalkynyl, aryl, aryl-$[C_1-C_8]$-alkyl, $[C_1-C_8]$-alkoxy-$[C_1-C_8]$-alkyl, $—C(=O)R^3$ and $—C(=O)OR^3$;

K is selected in the list consisting of oxygen, sulfur, $NR^3$, $N—OR^4$ and $N—NR^3R^4$;

$R^3$ is selected in the list consisting of hydrogen, $[C_1-C_8]$-alkyl, $[C_1-C_8]$-haloalkyl, $[C_3-C_6]$-cycloalkyl, $[C_1-C_8]$-alkoxycarbonyl, $[C_2-C_8]$-alkenyl, $[C_2-C_8]$-haloalkenyl, $[C_1-C_8]$-alkynyl, $[C_2-C_8]$-haloalkynyl, non-substituted or substituted phenyl, non-substituted or substituted pyridyl, non-substituted or substituted pyrazolyl, non-substituted or substituted thiazolyl, non-substituted or substituted isothiazolyl and non-substituted or substituted thiadiazolyl, wherein substituent group is selected in the list consisting of halogen, cyano, nitro, hydroxyl, mercapto, amino, $CONH_2$, COOH, CHO, $[C_1-C_4]$-alkyl, $[C_1-C_4]$-haloalkyl, $[C_3-C_6]$-cycloalkyl, $[C_1-C_3]$-alkoxy, $[C_1-C_3]$-haloalkoxy, $[C_1-C_3]$-alkylthio, $[C_1-C_3]$-haloalkylthio, $[C_1-C_3]$-alkylamino, $[C_1-C_3]$-dialkylamino, $[C_3-C_6]$-cycloalkylamino, $[C_1-C_3]$-alkoxycarbonyl, $[C_1-C_3]$-alkylsulfonyl, $[C_1-C_3]$-alkylaminocarbonyl and $[C_1-C_3]$-alkylaminosulfonyl;

$R^4$, $R^5$ and $R^6$ are independently selected in the list consisting of hydrogen, $[C_1-C_8]$-alkyl, $[C_1-C_8]$-haloalkyl, $[C_3-C_6]$-cycloalkyl, $[C_1-C_8]$-alkoxy, $[C_1-C_8]$-haloalkoxy, $[C_1-C_8]$-alkoxycarbonyl, $[C_2-C_8]$-alkenyl, $[C_2-C_8]$-haloalkenyl, $[C_2-C_8]$-alkynyl, $[C_2-C_8]$-haloalkynyl, non-substituted or substituted phenyl, non-substituted or substituted pyridyl, non-substituted or substituted pyrazolyl, non-substituted or substituted thiazolyl, non-substituted or substituted isothiazolyl and non-substituted or substituted thiadiazolyl, wherein substituent group is selected in the list consisting of halogen, cyano, nitro, hydroxyl, mercapto, amino, $CONH_2$, COOH, CHO, $[C_1-C_4]$-alkyl, $[C_1-C_4]$-haloalkyl, $[C_3-C_6]$-cycloalkyl, $[C_1-C_3]$-alkoxy, $[C_1-C_3]$-haloalkoxy, $[C_1-C_3]$-alkylthio, $[C_1-C_3]$-haloalkylthio, $[C_1-C_3]$-alkylamino, $[C_1-C_3]$-dialkylamino, $[C_3-C_6]$-cycloalkylamino, $[C_1-C_3]$-alkoxycarbonyl, $[C_1-C_3]$-alkylsulfonyl, $[C_1-C_3]$-alkylaminocarbonyl and $[C_1-C_3]$-alkylaminosulfonyl;

Q is selected in the list consisting of non-substituted or substituted phenyl, non-substituted or substituted pyridyl, non-substituted or substituted pyrazolyl, non-substituted or substituted thiazolyl, non-substituted or substituted isothiazolyl and non-substituted or substituted thiadiazolyl, wherein substituent group is selected in the list consisting of halogen, cyano, nitro, hydroxyl, mercapto, amino, $CONH_2$, COOH, CHO, $[C_1-C_4]$-alkyl, $[C_1-C_4]$-haloalkyl, $[C_3-C_6]$-cycloalkyl, $[C_1-C_3]$-alkoxy, $[C_1-C_3]$-haloalkoxy, $[C_1-C_3]$-alkylthio, $[C_1-C_3]$-haloalkylthio, $[C_1-C_3]$-alkylamino, $[C_1-C_3]$-dialkylamino, $[C_3-C_6]$-cycloalkylamino, $[C_1-C_3]$-alkoxycarbonyl, $[C_1-C_3]$-alkylsulfonyl, $[C_1-C_3]$-alkylaminocarbonyl and $[C_1-C_3]$-alkylaminosulfonyl;

T is selected in the list consisting of cyano, $[C_1-C_8]$-alkyl, $[C_1-C_8]$-haloalkyl, $[C_3-C_6]$-cycloalkyl, $[C_2-C_8]$-alkenyl, $[C_2-C_8]$-haloalkenyl, $[C_2-C_8]$-alkynyl, $[C_2-C_8]$-haloalkynyl, non-substituted or substituted phenyl, non-substituted or substituted pyridyl, non-substituted or substituted pyrazolyl, non-substituted or substituted thiazolyl, non-substituted or substituted isothiazolyl and non-substituted or substituted thiadiazolyl, wherein substituent group is selected in the list consisting of halogen, cyano, nitro, hydroxyl, mercapto, amino, $CONH_2$, COOH, CHO, $[C_1-C_4]$-alkyl, $[C_1-C_4]$-haloalkyl, $[C_3-C_6]$-cycloalkyl, $[C_1-C_3]$-alkoxy, $[C_1-C_3]$-haloalkoxy, $[C_1-C_3]$-alkylthio, $[C_1-C_3]$-haloalkylthio, $[C_1-C_3]$-alkylamino, $[C_1-C_3]$-dialkylamino, $[C_3-C_6]$-cycloalkylamino, $[C_1-C_3]$-alkoxycarbonyl, $[C_1-C_3]$-alkylsulfonyl, $[C_1-C_3]$-alkylaminocarbonyl and $[C_1-C_3]$-alkylaminosulfonyl. When L is $—(CR^1R^2)_n—$, $R^1$ and $R^2$ are selected from hydrogen and n is 1, W is not benzene;

The further preferred compounds of the general formula I in the present disclosure are:

L is selected in the list consisting of $—(CR^1R^2)_n—$, $—(CR^1R^2)_m—NH—(C=O)—CH_2—(CR^1R^2)_p—$, $—(CR^1R^2)_m—O—CH_2—(CR^1R^2)_p—$, $—(CR^1R^2)_m—S—CH_2—(CR^1R^2)_p—$;

n represents 1, 2, 3 or 4;

m and p independently represent 0, 1, 2 or 3;

$R^1$ and $R^2$ are selected from hydrogen;

W is selected in the list consisting of $W^1$, $W^2$, $W^3$, $W^4$, $W^{12}$, $W^{16}$, $W^{18}$, $W^{21}$, $W^{23}$, $W^5$, $W^{49}$, $W^{67}$, $W^{68}$, $W^{69}$, $W^{70}$, $W^{71}$, $W^{72}$, $W^{73}$, $W^{74}$, $W^{75}$, $W^{76}$, $W^{77}$, $W^{78}$, $W^{79}$, $W^{80}$, $W^{81}$, $W^{82}$, $W^{83}$ and $W^{84}$;

$X^1$, $X^2$, $X^3$, $X^4$, $X^5$, $X^6$, $X^7$, $X^8$ and $X^9$ are independently selected in the list consisting of hydrogen, halogen, cyano, nitro, $[C_1-C_3]$-alkyl, $[C_1-C_3]$-haloalkyl, $[C_1-C_3]$-alkoxy-$[C_1-C_3]$-alkyl, $—OR^3$, $—C(=O)OR^3$, $—N(R^4)S(=O)_2R^5$, $—S(=O)_2NR^3R^5$, $—N(R^4)C(=O)OR^3$, $—CR^4=NOR^3$, $—CH_2ON=C(CN)_2$, $NR^4C(=O)R^5$, non-substituted or substituted phenyl and non-substituted or substituted pyridyl, wherein substituent group is selected in the list consisting of halogen, cyano, nitro, $[C_1-C_3]$-alkyl, $[C_1-C_3]$-haloalkyl, $[C_1-C_3]$-alkoxy, $[C_1-C_3]$-haloalkoxy, $[C_1-C_3]$-alkylthio and $[C_1-C_3]$-haloalkylthio;

Z is selected in the list consisting of hydrogen, $[C_1-C_3]$-alkyl, $[C_1-C_3]$-haloalkyl, phenylmethyl, $—C(=O)R^3$ and $—C(=O)OR^3$;

K is selected in the list consisting of oxygen and sulfur;

$R^3$ is selected in the list consisting of hydrogen, $[C_1-C_3]$-alkyl, $[C_1-C_3]$-haloalkyl, $[C_1-C_8]$-alkoxycarbonyl, non-substituted or substituted phenyl and non-substituted or substituted pyridy, wherein substituent group is selected in the list consisting of halogen, cyano, nitro, $[C_1-C_3]$-alkyl, $[C_1-C_3]$-haloalkyl, $[C_1-C_3]$-alkoxy, $[C_1-C_3]$-haloalkoxy, $[C_1-C_3]$-alkylthio and $[C_1-C_3]$-haloalkylthio;

$R^4$ and $R^5$ are independently selected in the list consisting of hydrogen, $[C_1-C_3]$-alkyl, $[C_1-C_3]$-haloalkyl, $[C_1-C_3]$-alkoxy, $[C_1-C_3]$-haloalkoxy, $[C_1-C_3]$-alkoxycarbonyl, non-substituted or substituted phenyl and non-substituted or substituted pyridyl, wherein substituent group is selected in the list consisting of halogen, cyano, nitro, $[C_1-C_3]$-alkyl, $[C_1-C_3]$-haloalkyl, $[C_1-C_3]$-alkoxy, $[C_1-C_3]$-haloalkoxy, $[C_1-C_3]$-alkylthio and $[C_1-C_3]$-haloalkylthio;

Q is selected in the list consisting of $Q^{1-10}$, non-substituted or substituted phenyl and non-substituted or substituted pyridyl, wherein substituent group is selected in the list consisting of halogen, cyano, nitro, hydroxyl, mercapto, amino, $CONH_2$, COOH, CHO, $[C_1-C_3]$-alkyl, $[C_1-C_3]$-haloalkyl, $[C_3-C_6]$-cycloalkyl, $[C_1-C_3]$-alkoxy, $[C_1-C_3]$-haloalkoxy, $[C_1-C_3]$-alkylthio, $[C_1-C_3]$-haloalkylthio, $[C_1-C_3]$-alkylamino, $[C_1-C_3]$-dialkylamino, $[C_3-C_6]$- cycloalkylamino, [C$_1$-C$_3$]-alkoxycarbonyl, [C$_1$-C$_3$]-alkylsulfonyl, [C$_1$-C$_3$]-alkylaminocarbonyl and [C$_1$-C$_3$]-alkylaminosulfonyl;

Q$^1$
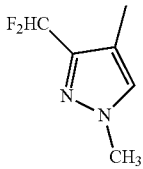

Q$^2$
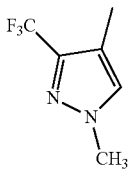

Q$^3$
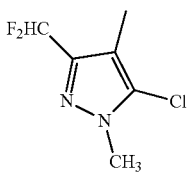

Q$^4$
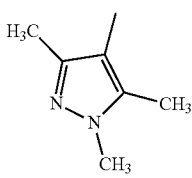

Q$^5$
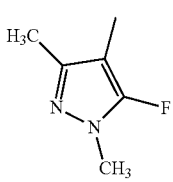

Q$^6$

Q$^7$
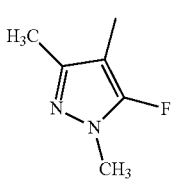

Q$^8$
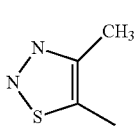

Q$^9$
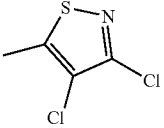

Q$^{10}$
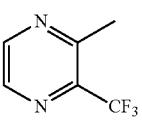

T is selected in the list consisting of cyano, [C$_1$-C$_3$]-alkyl, [C$_1$-C$_3$]-haloalkyl, [C$_3$-C$_6$]-cycloalkyl, non-substituted or substituted phenyl and non-substituted or substituted pyridyl, wherein substituent group is selected in the list consisting of halogen, cyano, nitro, [C$_1$-C$_3$]-alkyl, [C$_1$-C$_3$]-haloalkyl, [C$_3$-C$_6$]-cycloalkyl, [C$_1$-C$_3$]-alkoxy, [C$_1$-C$_3$]-haloalkoxy, [C$_1$-C$_3$]-alkylthio, [C$_1$-C$_3$]-haloalkylthio, [C$_1$-C$_3$]-alkylamino, [C$_1$-C$_3$]-dialkylamino, [C$_3$-C$_6$]-cycloalkylamino, [C$_1$-C$_3$]-alkoxycarbonyl, [C$_1$-C$_3$]-alkylsulfonyl, [C$_1$-C$_3$]-alkylaminocarbonyl and [C$_1$-C$_3$]-alkylaminosulfonyl.

When L is —(CR$^1$R$^2$)$_n$—, R$^1$ and R$^2$ are selected from hydrogen and n is 1, W is not benzene;

The further preferred compounds of the general formula I in the present disclosure are:

L is selected in the list consisting of —(CR$^1$R$^2$)$_n$—, —(CR$^1$R$^2$)$_m$—, NH—C(=O)—CH$_2$—(CR$^1$R$^2$)$_p$—, —(CR$^1$R$^2$)$_m$—O—CH$_2$—(CR$^1$R$^2$)$_p$—, —(CR$^1$R$^2$)$_m$—S—CH$_2$—(CR$^1$R$^2$)$_p$—;

n represents 1 or 2;

m and p independently represent 0, 1 or 2;

R$^1$ and R$^2$ are selected from hydrogen;

W is selected in the list consisting of W$^1$, W$^2$, W$^3$, W$^4$, W$^{12}$, W$^{16}$, W$^{18}$, W$^{21}$, W$^{23}$, W$^{48}$, W$^{49}$, W$^{67}$, W$^{68}$, W$^{69}$, W$^{70}$, W$^{71}$, W$^{72}$, W$^{73}$, W$^{74}$, W$^{75}$, W$^{76}$, W$^{77}$, W$^{78}$, W$^{79}$, W$^{80}$, W$^{81}$, W$^{82}$, W$^{83}$ and W$^{84}$;

X$^1$, X$^2$, X$^3$, X$^4$, X$^5$, X$^6$, X$^7$, X$^8$ and X$^9$ are independently selected in the list consisting of hydrogen, halogen, cyano, nitro, [C$_1$-C$_3$]-alkyl, [C$_1$-C$_3$]-haloalkyl, [C$_1$-C$_3$]-alkoxy-[C$_1$-C$_3$]-alkyl, —OR$^3$, —C(=O)OR$^3$, —N(R$^4$)S(=O)$_2$R$^5$, —S(=O)$_2$NR$^3$R$^5$, —N(R$^4$)C(=O)OR$^3$, —CR$^4$=NOR$^3$, —CH$_2$ON=C(CN)$_2$, NR$^4$C(=O)R$^5$, non-substituted or substituted phenyl and non-substituted or substituted pyridyl, wherein substituent group is selected in the list consisting of halogen, cyano, nitro, [C$_1$-C$_3$]-alkyl, [C$_1$-C$_3$]-haloalkyl, [C$_1$-C$_3$]-alkoxy, [C$_1$-C$_3$]-haloalkoxy, [C$_1$-C$_3$]-alkylthio and [C$_1$-C$_3$]-haloalkylthio;

Z is selected in the list consisting of hydrogen, [C$_1$-C$_3$]-alkyl, [C$_1$-C$_3$]-haloalkyl, phenylmethyl, —C(=O) R$^3$ and —C(=O)OR$^3$;

K is selected in the list consisting of oxygen or sulfur;

R$^3$ is selected in the list consisting of hydrogen, [C$_1$-C$_3$]-alkyl, [C$_1$-C$_3$]-haloalkyl, [C$_1$-C$_3$]-alkoxycarbonyl, non-substituted or substituted phenyl and non-substituted or substituted pyridy, wherein substituent group is selected in the list consisting of halogen, cyano, nitro, [C$_1$-C$_3$]-alkyl, [C$_1$-C$_3$]-haloalkyl, [C$_1$-C$_3$]-alkoxy, [C$_1$-C$_3$]-haloalkoxy, [C$_1$-C$_3$]-alkylthio and [C$_1$-C$_3$]-haloalkylthio;

R$^4$ and R$^5$ are independently selected in the list consisting of hydrogen, [C$_1$-C$_3$]-alkyl, [C$_1$-C$_3$]-haloalkyl, [C$_1$-C$_3$]-alkoxy, [C$_1$-C$_3$]-haloalkoxy, [C$_1$-C$_3$]-alkoxycarbonyl, non-substituted or substituted phenyl and non-substituted or substituted pyridyl, wherein substituent group is selected in the list consisting of halogen, cyano, nitro, [$C_1$-$C_3$]-alkyl, [$C_1$-$C_3$]-haloalkyl, [$C_1$-$C_3$]-alkoxy, [$C_1$-$C_3$]-haloalkoxy, [$C_1$-$C_3$]-alkylthio and [$C_1$-$C_3$]-haloalkylthio;

Q is selected in the list consisting of $Q^{1-10}$, non-substituted or substituted phenyl and non-substituted or substituted pyridyl, wherein substituent group is selected in the list consisting of halogen, cyano, nitro, hydroxyl, mercapto, amino, $CONH_2$, COOH, CHO, [$C_1$-$C_3$]-alkyl, [$C_1$-$C_3$]-haloalkyl, [$C_3$-$C_6$]-cycloalkyl, [$C_1$-$C_3$]-alkoxy, [$C_1$-$C_3$]-haloalkoxy, [$C_1$-$C_3$]-alkylthio, [$C_1$-$C_3$]-haloalkylthio, [$C_1$-$C_3$]-alkylamino, [$C_1$-$C_3$]-dialkylamino, [$C_3$-$C_6$]-cycloalkylamino, [$C_1$-$C_3$]-alkoxycarbonyl, [$C_1$-$C_3$]-alkylsulfonyl, [$C_1$-$C_3$]-alkylaminocarbonyl and [$C_1$-$C_3$]-alkylaminosulfonyl;

T is selected in the list consisting of cyano, [$C_1$-$C_3$]-alkyl, [$C_1$-$C_3$]-haloalkyl, [$C_3$-$C_6$]-cycloalkyl, non-substituted or substituted phenyl and non-substituted or substituted pyridyl, wherein substituent group is selected in the list consisting of halogen, cyano, nitro, [$C_1$-$C_3$]-alkyl, [$C_1$-$C_3$]-haloalkyl, [$C_3$-$C_6$]-cycloalkyl, [$C_1$-$C_3$]-alkoxy, [$C_1$-$C_3$]-haloalkoxy, [$C_1$-$C_3$]-alkylthio, [$C_1$-$C_3$]-haloalkylthio, [$C_1$-$C_3$]-alkylamino, [$C_1$-$C_3$]-dialkylamino, [$C_3$-$C_6$]-cycloalkylamino, [$C_1$-$C_3$]-alkoxycarbonyl, [$C_1$-$C_3$]-alkylsulfonyl, [$C_1$-$C_3$]-alkylaminocarbonyl and [$C_1$-$C_3$]-alkylaminosulfonyl.

When L is —$(CR^1R^2)_n$—, $R^1$ and $R^2$ are selected from hydrogen and n is 1, W is not benzene;

The further preferred compounds of the general formula I in the present disclosure are:

L is selected in the list consisting of —$(CR^1R^2)_n$—, —$(CR^1R^2)_m$—NH—(C=O)—$CH_2$—$(CR^1R^2)_p$—, —$(CR^1R^2)_m$—O—$CH_2$—$(CR^1R^2)_p$—, —$(CR^1R^2)_m$—S—$CH_2$—$(CR^1R^2)_p$—;

n represents 1 or 2;
m represents 0 or 1;
p represents 0, 1 or 2;
$R^1$ and $R^2$ are selected from hydrogen;
W is selected in the list consisting of $W^1$, $W^2$, $W^3$, $W^4$, $W^{12}$, $W^{16}$, $W^{18}$, $W^{21}$, $W^{23}$, $W^{48}$, $W^{49}$, $W^{67}$, $W^{68}$, $W^{69}$, $W^{70}$, $W^{71}$, $W^{72}$, $W^{73}$, $W^{74}$, $W^{75}$, $W^{76}$, $W^{77}$, $W^{78}$, $W^{79}$, $W^{80}$, $W^{81}$, $W^{82}$, $W^{83}$ and $W^{84}$;

$X^1$, $X^2$, $X^3$, $X^4$, $X^5$, $X^6$, $X^7$, $X^8$ and $X^9$ are independently selected in the list consisting of hydrogen, halogen, cyano, nitro, [$C_1$-$C_3$]-alkyl, [$C_1$-$C_3$]-haloalkyl, [$C_1$-$C_3$]-alkoxy-[$C_1$-$C_3$]-alkyl, —$OR^3$, —C(=O)$OR^3$, —$N(R^4)S(=O)_2R^5$, —S(=O)$_2NR^3R^5$, —$N(R^4)C(=O)OR^3$, —$CR^4$=$NOR^3$, —$CH_2ON$=C(CN)$_2$, $NR^4C$(=O)$R^5$, non-substituted or substituted phenyl and non-substituted or substituted pyridyl, wherein substituent group is selected in the list consisting of halogen, cyano, nitro, [$C_1$-$C_3$]-alkyl, [$C_1$-$C_3$]-haloalkyl, [$C_1$-$C_3$]-alkoxy and [$C_1$-$C_3$]-haloalkoxy;

Z is selected in the list consisting of hydrogen, methyl, phenylmethyl, —C(=O) $R^3$ and —C(=O)$OR^3$;

K is selected from oxygen;

$R^3$ is selected in the list consisting of hydrogen, [$C_1$-$C_3$]-alkyl, [$C_1$-$C_3$]-haloalkyl, [$C_1$-$C_3$]-alkoxycarbonyl, non-substituted or substituted phenyl and non-substituted or substituted pyridy, wherein substituent group is selected in the list consisting of halogen, cyano, nitro, [$C_1$-$C_3$]-alkyl, [$C_1$-$C_3$]-haloalkyl, [$C_1$-$C_3$]-alkoxy, [$C_1$-$C_3$]-haloalkoxy, [$C_1$-$C_3$]-alkylthio and [$C_1$-$C_3$]-haloalkylthio;

$R^4$ and $R^5$ are independently selected in the list consisting of hydrogen, [$C_1$-$C_3$]-alkyl, [$C_1$-$C_3$]-haloalkyl, [$C_1$-$C_3$]-alkoxy, [$C_1$-$C_3$]-haloalkoxy, [$C_1$-$C_3$]-alkoxycarbonyl, non-substituted or substituted phenyl and non-substituted or substituted pyridyl, wherein substituent group is selected in the list consisting of halogen, cyano, nitro, [$C_1$-$C_3$]-haloalkyl, [$C_1$-$C_3$]-alkoxy, [$C_1$-$C_3$]-haloalkoxy, [$C_1$-$C_3$]-alkylthio and [$C_1$-$C_3$]-haloalkylthio;

Q is selected in the list consisting of $Q^{1-10}$, non-substituted or substituted phenyl and non-substituted or substituted pyridyl, wherein substituent group is selected in the list consisting of halogen, cyano, nitro, hydroxyl, mercapto, amino, $CONH_2$, COOH, CHO, [$C_1$-$C_3$]-alkyl, [$C_1$-$C_3$]-haloalkyl, [$C_3$-$C_6$]-cycloalkyl, [$C_1$-$C_3$]-alkoxy, [$C_1$-$C_3$]-haloalkoxy, [$C_1$-$C_3$]-alkylthio, [$C_1$-$C_3$]-haloalkylthio, [$C_1$-$C_3$]-alkylamino, [$C_1$-$C_3$]-dialkylamino, [$C_3$-$C_6$]-cycloalkylamino, [$C_1$-$C_3$]-alkoxycarbonyl, [$C_1$-$C_3$]-alkylsulfonyl, [$C_1$-$C_3$]-alkylaminocarbonyl and [$C_1$-$C_3$]-alkylaminosulfonyl;

T is selected in the list consisting of cyano, [$C_1$-$C_3$]-alkyl, [$C_1$-$C_3$]-haloalkyl, [$C_3$-$C_6$]-cycloalkyl, non-substituted or substituted phenyl or non-substituted or substituted pyridyl, wherein substituent group is selected in the list consisting of halogen, cyano, nitro, [$C_1$-$C_3$]-alkyl, [$C_1$-$C_3$]-haloalkyl, [$C_3$-$C_6$]-cycloalkyl, [$C_1$-$C_3$]-alkoxy, [$C_1$-$C_3$]-haloalkoxy, [$C_1$-$C_3$]-alkylthio and [$C_1$-$C_3$]-haloalkylthio.

When L is —$(CR^1R^2)_n$—, $R^1$ and $R^2$ are selected from hydrogen and n is 1, W is not benzene;

The further preferred compounds of the general formula I in the present disclosure are:

L is selected in the list consisting of —$(CR^1R^2)_n$—, —$(CR^1R^2)_m$—, NH—(C=O)—$CH_2$—$(CR^1R^2)_p$—, —$(CR^1R^2)_m$—$CH_2(CR^1R^2)_p$—, —$(CR^1R^2)_m$—S—$CH_2$—$(CR^1R^2)_p$—;

n represents 1 or 2;
m represents 0;
p represents 0 or 1;
$R^1$ and $R^2$ are selected from hydrogen;
W is selected in the list consisting of $W^1$, $W^2$, $W^3$, $W^4$, $W^{12}$, $W^{16}$, $W^{18}$, $W^{21}$, $W^{23}$, $W^{48}$, $W^{49}$, $W^{67}$, $W^{68}$, $W^{69}$, $W^{70}$, $W^{71}$, $W^{72}$, $W^{74}$, $W^{79}$, $W^{80}$, $W^{81}$, $W^{82}$ and $W^{83}$;

$X^1$, $X^2$, $X^3$, $X^4$, $X^5$, $X^6$, $X^7$, $X^8$ and $X^9$ are independently selected in the list consisting of hydrogen, fluorine, chlorine, bromine, cyano, nitro, methyl, ethyl, isopropyl, chloromethyl, bromomethyl, difluoromethyl, trifluoromethyl, heptafluoroisopropyl, —$OR^3$, —C(=O)$OR^3$, —$N(R^4)S(=O)_2R^5$, —S(=O)$_2NR^3R^4$, —$N(R')C(=O)OR^3$, —$CR^4$=$NOR^3$, —$CH_2ON$=C(CN)$_2$, $NR^4C$(=O)$R^5$, non-substituted or substituted phenyl and non-substituted or substituted pyridyl, wherein substituent group is selected in the list consisting of halogen, cyano, nitro, trifluoromethyl, heptafluoropropyl, heptafluoroisopropyl, methoxy and trifluoromethoxy;

Z is selected in the list consisting of hydrogen, methyl and phenylmethyl;

K is selected from oxygen;

$R^3$ is selected in the list consisting of hydrogen, methyl, ethyl, propyl, isopropyl, cyclopropyl, difluoromethyl, trifluoromethyl, heptafluoropropyl, heptafluoroisopropyl, methoxycarbonyl, non-substituted or substituted phenyl and non-substituted or substituted pyridy, wherein substituent group is selected in the list consisting of halogen, cyano, nitro and trifluoromethyl;

$R^4$ and $R^5$ are independently selected in the list consisting of hydrogen, methyl, ethyl, propyl, isopropyl, cyclopropyl, difluoromethyl, trifluoromethyl, heptafluoropropyl, heptafluoroisopropyl, methoxy, trifluoromethoxy, methoxycarbonyl, non-substituted or substituted phenyl and non-substituted or substituted pyridyl, wherein substituent group is selected in the list consisting of halogen, cyano, nitro, methyl, ethyl, propyl, chloromethyl, bromomethyl, trifluoromethyl, heptafluoroisopropyl, methoxy and trifluoromethoxy;

Q is selected in the list consisting of $Q^{1-10}$, non-substituted or substituted phenyl and non-substituted or substituted pyridyl, wherein substituent group is selected in the list consisting of halogen, cyano, nitro, hydroxyl, mercapto, amino, [$C_1$-$C_3$]-haloalkyl, [$C_1$-$C_3$]-alkoxy, [$C_1$-$C_3$]-haloalkoxy, [$C_1$-$C_3$]-alkylthio and [$C_1$-$C_3$]-haloalkylthio;

T is selected in the list consisting of cyano, [$C_1$-$C_3$]-alkyl, [$C_1$-$C_3$]-haloalkyl, [$C_3$-$C_6$]-cycloalkyl, non-substituted or substituted phenyl and non-substituted or substituted pyridyl, wherein substituent group is selected in the list consisting of halogen, cyano, nitro, [$C_1$-$C_3$]-alkyl, [$C_1$-$C_3$]-haloalkyl, [$C_1$-$C_6$]-cycloalkyl, [$C_1$-$C_3$]-alkoxy, [$C_1$-$C_3$]-haloalkoxy, [$C_1$-$C_3$]-alkylthio and [$C_1$-$C_3$]-haloalkylthio.

When L is —$(CR^1R^2)_n$—, $R^1$ and $R^2$ are selected from hydrogen and n is 1, W is not benzene;

The further preferred compounds of the general formula I in the present disclosure are:

L is selected in the list consisting of —$CH_2$—, —$CH_2$—$CH_2$—, —NH—(C=O)—$CH_2$— and —O—$CH_2$—$CH_2$—;
W is selected in the list consisting of $W^1$, $W^2$, $W^3$, $W^4$, $W^2$, $W^6$, $W^{18}$, $W^{21}$, $W^{23}$, $W^{48}$, $W^{49}$, $W^{67}$, $W^{68}$, $W^{69}$, $W^{70}$, $W^{71}$, $W^{72}$, $W^{74}$, $W^{79}$, $W^{80}$, $W^{81}$, $W^{82}$ and $W^{83}$;
$X^1$, $X^2$, $X^3$, $X^4$, $X^5$, $X^6$, $X^7$, $X^8$ and $X^9$ are independently selected in the list consisting of hydrogen, fluorine, chlorine, bromine, cyano, nitro, methyl, ethyl, isopropyl, chloromethyl, bromomethyl, difluoromethyl, trifluoromethyl, heptafluoroisopropyl, —$OR^3$, —C(=O)$OR^3$, —N($R^4$)S(=O)$_2$$R^5$, —S(=O)$_2$N$R^3R^4$, —N($R^4$)C(=O)$OR^3$, —$CR^4$=$NOR^3$, —$CH_2$ON=C(CN)$_2$, $NR^4$C(=O)$R^5$, non-substituted or substituted phenyl and non-substituted or substituted pyridyl, wherein substituent group is selected in the list consisting of halogen, cyano, nitro, trifluoromethyl, heptafluoropropyl, heptafluoroisopropyl, methoxy and trifluoromethoxy;
Z is selected in the list consisting of hydrogen, methyl and phenylmethyl;
K is selected from oxygen;
$R^3$ is selected in the list consisting of hydrogen, methyl, ethyl, propyl, isopropyl, cyclopropyl, difluoromethyl, trifluoromethyl, heptafluoropropyl, heptafluoroisopropyl, methoxycarbonyl, non-substituted or substituted phenyl and non-substituted or substituted pyridy, wherein substituent group is selected in the list consisting of halogen, cyano, nitro and trifluoromethyl;
$R^4$ and $R^5$ are independently selected in the list consisting of hydrogen, methyl, ethyl, propyl, isopropyl, cyclopropyl, difluoromethyl, trifluoromethyl, heptafluoropropyl, heptafluoroisopropyl, methoxy, trifluoromethoxy, methoxycarbonyl, non-substituted or substituted phenyl and non-substituted or substituted pyridyl, wherein substituent group is selected in the list consisting of halogen, cyano, nitro, methyl, ethyl, propyl, chloromethyl, bromomethyl, trifluoromethyl, heptafluoroisopropyl, methoxy and trifluoromethoxy;
Q is selected in the list consisting of $Q^{1-10}$, non-substituted or substituted phenyl and non-substituted or substituted pyridyl, wherein substituent group is selected in the list consisting of halogen, cyano, nitro, hydroxyl, mercapto, amino, chloromethyl, bromomethyl, difluoromethyl, trifluoromethyl, heptafluoroisopropyl, methoxy, ethoxy, propoxy, isopropoxy, trifluoromethoxy, methylthio, ethylthio, trifluoromethylthio and trifluoroethylthio;
T is selected in the list consisting of cyano, methyl, ethyl, propyl, isopropyl, cyclopropyl, trifluoromethyl, difluoroethyl, cyclopropyl, cyclobutanyl, cyclopentyl, cyclohexyl, non-substituted or substituted phenyl and non-substituted or substituted pyridyl, wherein substituent group is selected in the list consisting of halogen, cyano, nitro, methyl, ethyl, propyl, isopropyl, chloromethyl, bromomethyl, trifluoromethyl, heptafluoroisopropyl, cyclopropyl, cyclobutanyl, cyclopentyl, cyclohexyl, methoxy, ethoxy, propoxy, isopropoxy, trifluoromethoxy, methylthio, ethylthio, trifluoromethylthio and trifluoroethylthio;

When L is —$(CR^1R^2)_n$—, $R^1$ and $R^2$ are selected from hydrogen and n is 1, W is not benzene;

The more preferred compounds of the general formula I in the present disclosure are:

L is selected in the list consisting of —$CH_2$—, —$CH_2$—$CH_2$—, —NH—(C=O)—$CH_2$— and —O—$CH_2$—$CH_2$—;
W is selected in the list consisting of $W^1$, $W^2$, $W^3$ and $W^4$;
$X^1$, $X^2$, $X^3$, $X^4$, $X^5$, $X^6$, $X^7$, $X^8$ and $X^9$ are independently selected in the list consisting of hydrogen, fluorine, chlorine, bromine, cyano, nitro, methyl, ethyl, isopropyl, chloromethyl, bromomethyl, difluoromethyl, trifluoromethyl, heptafluoroisopropyl, —$OR^3$, —C(=O)$OR^3$, —N($R^4$)S(=O)$_2$$R^5$, —S(=O)$_2$N$R^3R^4$, —N($R^4$)C(=O)$OR^3$, —$CR^4$=$NOR^3$, —$CH_2$ON=C(CN)$_2$, $NR^4$C(=O)$R^5$, non-substituted or substituted phenyl and non-substituted or substituted pyridyl, wherein substituent group is selected in the list consisting of halogen, cyano, nitro, trifluoromethyl, heptafluoropropyl, heptafluoroisopropyl, methoxy and trifluoromethoxy;
$R^3$ is selected in the list consisting of hydrogen, methyl, ethyl, propyl, isopropyl, cyclopropyl, difluoromethyl, trifluoromethyl, heptafluoropropyl, heptafluoroisopropyl, methoxycarbonyl, non-substituted or substituted phenyl and non-substituted or substituted pyridy, wherein substituent group is selected in the list consisting of halogen, cyano, nitro and trifluoromethyl;
$R^4$ and $R^5$ are independently selected in the list consisting of hydrogen, methyl, ethyl, propyl, isopropyl, cyclopropyl, difluoromethyl, trifluoromethyl, heptafluoropropyl, heptafluoroisopropyl, methoxy, trifluoromethoxy, methoxycarbonyl, non-substituted or substituted phenyl and non-substituted or substituted pyridyl, wherein substituent group is selected in the list consisting of halogen, cyano, nitro, methyl, ethyl, propyl, chloromethyl, bromomethyl, trifluoromethyl, heptafluoroisopropyl, methoxy and trifluoromethoxy;
when L represents —$CH_2$—, W is not benzene.

Or the more preferred compounds of the general formula I in the present disclosure are:

L is selected in the list consisting of —$CH_2$—, —$CH_2$—$CH_2$—, —NH—(C=O)—$CH_2$— and —O—$CH_2$—$CH_2$—;
W is selected in the list consisting of $W^{12}$, $W^{16}$, $W^{18}$, $W^{23}$, $W^{49}$, $W^{67}$, $W^{68}$, $W^{69}$ and $W^{82}$;
$X^1$, $X^2$, $X^3$, $X^4$, $X^5$, $X^6$, $X^7$, $X^8$ and $X^9$ are independently selected in the list consisting of hydrogen, fluorine, chlorine, bromine, cyano, nitro, methyl, ethyl, isopropyl, chloromethyl, bromomethyl, difluoromethyl, trifluoromethyl, heptafluoroisopropyl, —$OR^3$, —C(=O)$OR^3$, —N($R^4$)S(=O)$_2$$R^5$, —S(=O)$_2$N$R^3R^4$, —N($R^4$)C(=O)$OR^3$, —$CR^4$=$NOR^3$, —$CH_2$ON=C(CN)$_2$, $NR^4$C(=O)$R^5$, non-substituted or substituted phenyl and non-substituted or substituted pyridyl, wherein substituent group is selected in the list consisting of halogen, cyano, nitro, trifluoromethyl, heptafluoropropyl, heptafluoroisopropyl, methoxy and trifluoromethoxy;
Z is selected in the list consisting of hydrogen, methyl and phenylmethyl;
K is selected from oxygen;
$R^3$ is selected in the list consisting of hydrogen, methyl, ethyl, propyl, isopropyl, cyclopropyl, difluoromethyl, trifluoromethyl, heptafluoropropyl, heptafluoroisopropyl, methoxycarbonyl, non-substituted or substituted phenyl and non-substituted or substituted pyridy, wherein substituent group is selected in the list consisting of halogen, cyano, nitro and trifluoromethyl;

$R^4$ and $R^5$ are independently selected in the list consisting of hydrogen, methyl, ethyl, propyl, isopropyl, cyclopropyl, difluoromethyl, trifluoromethyl, heptafluoropropyl, heptafluoroisopropyl, methoxy, trifluoromethoxy, methoxycarbonyl, non-substituted or substituted phenyl and non-substituted or substituted pyridyl, wherein substituent group is selected in the list consisting of halogen, cyano, nitro, methyl, ethyl, propyl, chloromethyl, bromomethyl, trifluoromethyl, heptafluoroisopropyl, methoxy and trifluoromethoxy;

The most preferred compounds of the general formula I in the present disclosure are:

L is selected in the list consisting of —$CH_2$—, —$CH_2$—$CH_2$—, —NH—(C=O)—$CH_2$— and —O—$CH_2$—$CH_2$—;

W is selected in the list consisting of $W^{21}$, $W^{48}$, $W^{70}$, $W^{71}$, $W^{72}$, $W^{74}$, $W^{79}$, $W^{80}$, $W^{81}$ and $W^{83}$;

$X^1$, $X^2$, $X^3$, $X^4$, $X^5$, $X^6$, $X^7$, $X^8$ and $X^9$ are independently selected in the list consisting of hydrogen, fluorine, chlorine, bromine, cyano, nitro, methyl, ethyl, isopropyl, chloromethyl, bromomethyl, difluoromethyl, trifluoromethyl, heptafluoroisopropyl, methoxy and trifluoromethoxy;

Z is selected in the list consisting of hydrogen or methyl

K is selected from oxygen;

Q is selected in the list consisting of $Q^{1-10}$, non-substituted or substituted phenyl and non-substituted or substituted pyridyl, wherein substituent group is selected in the list consisting of halogen, cyano, nitro, hydroxyl, mercapto, amino, chloromethyl, bromomethyl, difluoromethyl, trifluoromethyl, heptafluoroisopropyl, methoxy, ethoxy, propoxy, isopropoxy, trifluoromethoxy, methylthio, ethylthio, trifluoromethylthio and trifluoroethylthio;

T is selected in the list consisting of cyano, methyl, ethyl, propyl, isopropyl, cyclopropyl, trifluoroethyl, difluoroethyl, cyclopropyl, cyclobutanyl, cyclopentyl, cyclohexyl, non-substituted or substituted phenyl and non-substituted or substituted pyridyl, wherein substituent group is selected in the list consisting of halogen, cyano, nitro, methyl, ethyl, propyl, isopropyl, chloromethyl, bromomethyl, trifluoromethyl, heptafluoroisopropyl, cyclopropyl, cyclobutanyl, cyclopentyl, cyclohexyl, methoxy, ethoxy, propoxy, isopropoxy, trifluoromethoxy, methylthio, ethylthio, trifluoromethylthio and trifluoroethylthio.

The terms used above to definite the compounds of general formula are as follows:

Non-substituted means all substituents are hydrogen.

The "halogen" or "halo" is fluorine, chlorine, bromine or iodine.

The "alkyl" stands for straight or branched chain alkyl, such as methyl, ethyl, n-propyl, isopropyl, butyl, butyl isomers, pentyl, pentyl isomers, hexyl and hexyl isomers.

The "haloalkyl" stands for straight or branched chain alkyl, in which hydrogen atoms can be all or partly substituted with halogen, such as chloromethyl, dichloromethyl, trichloromethyl, fluoromethyl, difluoromethyl, trifluoromethyl, heptafluoroisopropyl, etc.

The "cycloalkyl" is substituted or unsubstituted cyclic alkyl, such as cyclopropyl, cyclopentyl or cyclohexyl, the substitute(s) is (are) methyl, halogen, etc.

The "alkenyl" refers to straight or branched chain alkenyl, such as ethenyl, 1-propenyl, 2-propenyl, and different isomer of butenyl, pentenyl and hexenyl. Alkenyl also includes polyene, such as propa-1,2-dienyl and hexa-2,4-dienyl.

The "haloalkenyl" stands for straight or branched chain alkenyl in which hydrogen atoms can be all or partly substituted with halogen.

The "alkynyl" refers to straight or branched chain alkynyl, such as ethynyl, 1-propynyl, 2-propynyl, and different isomer of butynyl, pentynyl and hexynyl.

Alkynyl also includes groups including more than one triple bonds such as hexa-2,5-diynyl.

The "haloalkynyl" stands for straight or branched chain alkynyl, in which hydrogen atoms can be all or partly substituted with halogen.

The "alkoxy" refers to straight or branched chain alkyl, which is linked to the structure by oxygen atom, such as methoxy, ethoxy, tert-butoxy, etc.

The "haloalkoxy" refers to straight or branched chain alkoxy, in which hydrogen atoms can be all or partly substituted with halogen, such as chloromethoxy, dichloromethoxy, trichloromethoxy, fluoromethoxy, difluoromethoxy, trifluoromethoxy, chlorofluoromethoxy, trifluoroethoxy, etc.

The "alkylthio" refers to straight or branched chain alkyl, which is linked to the structure by sulfur atom, such as methylthio, ethylthio, etc.

The "haloalkylthio" refers to straight or branched chain alkylthio, in which hydrogen atoms can be all or partly substituted with halogen, su
ch as difluoromethylthio, trifluoroethylthio, etc.

The "alkylamino" refers to straight or branched chain alkyl, which is linked to the structure by nitrogen atom, such as methylamino, ethylamino, n-propylamino, isopropylamino, ethylthio or different isomer of butylamino.

The "dialkylamino" refers to two identical or different straight-chain or branched-chain alkyl, which are linked to the structure by nitrogen atom, such as —$N(CH_3)_2$—,

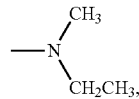

etc.

The "cycloalkylamino" refers to cycloalkyl-NH—, such as cyclopropylamino.

The "alkylaminocarbonyl" refers to alkyl-NH—CO—, such as $CH_3NHCO$—.

The "alkylaminosulfonyl" refers to alkyl-NH—$S(O)_2$—, such as $CH_3NHS(O)_2$—.

The "alkoxyalkyl" refers to alkyl-O-alkyl, such as $CH_3OCH_2$—.

The "haloalkoxyalkyl" refers to alkoxyalkyl, in which hydrogen atoms can be all or partly substituted with halogen, such as $ClCH_2$—O—$CH_2$—, $Cl_2CH$—O—$CH_2$—, $Cl_3C$—O—$CH_2$—, $FCH_2$—O—$CH_2$—, $F_2CH$—O—$CH_2$—, $F_3C$—O—$CH_2$—, $FClCH$—O—$CH_2$—, $CF_3$—$CH_2$—O—$CH_2$—, etc.

The "alkoxyalkoxy" refers to alkyl-O-alkyl-O—, such as $CH_3OCH_2O$—.

The "alkoxycarbonyl" refers to alkyl-O—CO—, such as $CH_3OCO$—.

The "alkylsulfonyl" refers to alkyl-$S(O)_2$—, such as methylsulfonyl.

The "aryl" means aromatic monocyclic groups having 6 to 20 carbon atoms or aromatic polycyclic groups having 6 to 20 carbon atoms, such as phenyl, naphthyl.

The "arylalkyl" refers to aryl-alkyl-, such as $PhCH_2$—.

The "heteroaryl" means heteroaromatic monocyclic groups having 6 to 20 carbon atoms, 1 to 4 heteroatoms selected from N, S, O or heteroaromatic polycyclic groups having 6 to 20 carbon atoms, 1 to 4 heteroatoms selected from N, S, O. Such as pyrrolyl, furyl, thienyl, imidazolyl, pyrazolyl, oxazolyl, thiazolyl, isoxazolyl, isothiazolyl, pyridyl, pyrimidinyl, pyridazinyl, pyridazinonyl, indolyl, benzofuranyl, benzoxazolyl, benzothienyl, benzothiazolyl, benzisoxazolyl, benzisothiazolyl, benzimidazolyl, benzopyrazolyl, quinoxalinyl, etc.

The specific compounds in Table 1 are used to illustrate the present invention, but not to limit it.

TABLE 1

$$W-L-O-N=C(CN)_2 \quad \text{I}$$

| No | W | L |
|----|---|---|
| 1 | 4-CF$_3$S—Ph | —CH$_2$— |
| 2 | 2-Cl—Ph | —CH$_2$— |
| 3 | 3-Cl—Ph | —CH$_2$— |
| 4 | 4-Cl—Ph | —CH$_2$— |
| 5 | 2-F—Ph | —CH$_2$— |
| 6 | 3-F—Ph | —CH$_2$— |
| 7 | 4-F—Ph | —CH$_2$— |
| 8 | 2-Br—Ph | —CH$_2$— |
| 9 | 3-Br—Ph | —CH$_2$— |
| 10 | 4-Br—Ph | —CH$_2$— |
| 11 | 2-I—Ph | —CH$_2$— |
| 12 | 3-I—Ph | —CH$_2$— |
| 13 | 4-I—Ph | —CH$_2$— |
| 14 | 2-Me—Ph | —CH$_2$— |
| 15 | 3-Me—Ph | —CH$_2$— |
| 16 | 4-Me—Ph | —CH$_2$— |
| 17 | 2-MeO—Ph | —CH$_2$— |
| 18 | 3-MeO—Ph | —CH$_2$— |
| 19 | 4-MeO—Ph | —CH$_2$— |
| 20 | 2-CF$_3$—Ph | —CH$_2$— |
| 21 | 3-CF$_3$—Ph | —CH$_2$— |
| 22 | 4-CF$_3$—Ph | —CH$_2$— |
| 23 | 2-CF$_3$O—Ph | —CH$_2$— |
| 24 | 3-CF$_3$O—Ph | —CH$_2$— |
| 25 | 4-CF$_3$O—Ph | —CH$_2$— |
| 26 | 2-CHF$_2$O—Ph | —CH$_2$— |
| 27 | 3-CHF$_2$O—Ph | —CH$_2$— |
| 28 | 4-CHF$_2$O—Ph | —CH$_2$— |
| 29 | 2-(CF$_3$)$_2$CF—Ph | —CH$_2$— |
| 30 | 3-(CF$_3$)$_2$CF—Ph | —CH$_2$— |
| 31 | 4-(CF$_3$)$_2$CF—Ph | —CH$_2$— |
| 32 | 2-NO$_2$—Ph | —CH$_2$— |
| 33 | 3-NO$_2$—Ph | —CH$_2$— |
| 34 | 4-NO$_2$—Ph | —CH$_2$— |
| 35 | 2-CN—Ph | —CH$_2$— |
| 36 | 3-CN—Ph | —CH$_2$— |
| 37 | 4-CN—Ph | —CH$_2$— |
| 38 | 2-N(CH$_3$)$_2$—Ph | —CH$_2$— |
| 39 | 3-N(CH$_3$)$_2$—Ph | —CH$_2$— |
| 40 | 4-N(CH$_3$)$_2$—Ph | —CH$_2$— |
| 41 | 2-pyridyl | —CH$_2$— |
| 42 | 3-pyridyl | —CH$_2$— |
| 43 | 4-pyridyl | —CH$_2$— |
| 44 | 2-furyl | —CH$_2$— |
| 45 | 2-thiazolyl | —CH$_2$— |
| 46 | 3-Cl-2-pyridyl | —CH$_2$— |
| 47 | 4-Cl-2-pyridyl | —CH$_2$— |
| 48 | 5-Cl-2-pyridyl | —CH$_2$— |
| 49 | 6-Cl-2-pyridyl | —CH$_2$— |
| 50 | 2-Cl-3-pyridyl | —CH$_2$— |
| 51 | 4-Cl-3-pyridyl | —CH$_2$— |
| 52 | 5-Cl-3-pyridyl | —CH$_2$— |
| 53 | 6-Cl-3-pyridyl | —CH$_2$— |
| 54 | 2-Cl-4-pyridyl | —CH$_2$— |
| 55 | 3-Cl-4-pyridyl | —CH$_2$— |
| 56 | 1-naphthyl | —CH$_2$— |
| 57 | 2,4-diCl—Ph | —CH$_2$— |
| 58 | 2,6-diCl—Ph | —CH$_2$— |
| 59 | 3,4-diCl—Ph | —CH$_2$— |
| 60 | 3,5-diCl—Ph | —CH$_2$— |
| 61 | 2-Cl-6-F—Ph | —CH$_2$— |
| 62 | 2-Cl-4-Me—Ph | —CH$_2$— |
| 63 | 2,4-di(MeO)—Ph | —CH$_2$— |
| 64 | 2-Cl-4-Et—Ph | —CH$_2$— |

TABLE 1-continued $$\underset{W}{\overset{}{\underset{L}{\bigvee}}} O \underset{N}{\overset{}{\bigvee}} \underset{CN}{\overset{CN}{=}}$$ I

| No | W | L |
|---|---|---|
| 65 | 2-Cl-5-NO$_2$—Ph | —CH$_2$— |
| 66 | 3-Cl-4-Me—Ph | —CH$_2$— |
| 67 | 4-Cl-3-Me—Ph | —CH$_2$— |
| 68 | 2-F-4-Me—Ph | —CH$_2$— |
| 69 | 2-F-4-CN—Ph | —CH$_2$— |
| 70 | 3-F-4-Me—Ph | —CH$_2$— |
| 71 | 2,4-diMe—Ph | —CH$_2$— |
| 72 | 2,5-diMe—Ph | —CH$_2$— |
| 73 | 3,4-diMe—Ph | —CH$_2$— |
| 74 | 3,4-di(MeO)—Ph | —CH$_2$— |
| 75 | 3,5-di(MeO)—Ph | —CH$_2$— |
| 76 | 3,5-di(CF$_3$)—Ph | —CH$_2$— |
| 77 | 2,5-diCl-4-F—Ph | —CH$_2$— |
| 78 | 2,4,5-triCl—Ph | —CH$_2$— |
| 79 | 2,4,6-triCl—Ph | —CH$_2$— |
| 80 | 2,4,6-triCH$_3$—Ph | —CH$_2$— |
| 81 | 2-F-4-CN—Ph | —CH$_2$— |
| 82 | 2,4-diF—Ph | —CH$_2$— |
| 83 | 3,4-diF—Ph | —CH$_2$— |
| 84 | 3,5-diF—Ph | —CH$_2$— |
| 85 | 2,6-diF—Ph | —CH$_2$— |
| 86 | 2,4,5-triF—Ph | —CH$_2$— |
| 87 | 3,4,5-triF—Ph | —CH$_2$— |
| 88 | 2,4,6-triF—Ph | —CH$_2$— |
| 89 | 2,3,4,5,6-5F—Ph | —CH$_2$— |
| 90 | 4-tert-butylphenyl | —CH$_2$— |
| 91 | 4-(MeOOC)phenyl | —CH$_2$— |
| 92 | 4-(HOOC)phenyl | —CH$_2$— |
| 93 | 3-phenoxyphenyl | —CH$_2$— |
| 94 | 2-phenoxyphenyl | —CH$_2$— |

TABLE 1-continued $$W-L-O-N=C(CN)_2 \quad \text{(I)}$$

| No | W | L |
|---|---|---|
| 95 | 4-phenoxyphenyl | —CH₂— |
| 96 | biphenyl-2-yl | —CH₂— |
| 97 | biphenyl-3-yl | —CH₂— |
| 98 | biphenyl-4-yl | —CH₂— |
| 99 | 4'-fluorobiphenyl-2-yl | —CH₂— |
| 100 | 2',4',6'-trichlorobiphenyl-2-yl | —CH₂— |
| 101 | 3',4',5'-trifluorobiphenyl-2-yl | —CH₂— |
| 102 | 2-methylbiphenyl-3-yl | —CH₂— |

TABLE 1-continued $$\underset{W-L-O-N}{\overset{CN}{\underset{CN}{\parallel}}}$$  I

| No | W | L |
|---|---|---|
| 103 | (4-chloromethyl-phenyl) | —CH₂— |
| 104 | (4-((dicyanomethylene-amino)oxymethyl)phenyl) | —CH₂— |
| 105 | (3-((dicyanomethylene-amino)oxymethyl)phenyl) | —CH₂— |
| 106 | (2,4,6-trimethyl-3-((dicyanomethylene-amino)oxymethyl)phenyl) | —CH₂— |
| 107 | (2-chloro-thiazol-5-yl) | —CH₂— |
| 108 | (pyrimidin-2-yl) | —CH₂— |
| 109 | (2-(methoxymethylene)(methoxycarbonyl)methyl-phenyl) | —CH₂— |
| 110 | (2-(methoxyimino)(methoxycarbonyl)methyl-phenyl) | —CH₂— |

TABLE 1-continued $$W-L-O-N=C(CN)_2 \quad \text{I}$$

| No | W | L |
|---|---|---|
| 111 | 2-(N-methoxy-N-methoxycarbonylamino)phenyl | —CH$_2$— |
| 112 | 3-benzoylphenyl | —CH$_2$— |
| 113 | 4-benzoylphenyl | —CH$_2$— |
| 114 | 2-benzoylphenyl | —CH$_2$— |
| 115 | 2-phenylthiazol-4-yl | —CH$_2$— |
| 116 | 2-(4-chlorophenyl)thiazol-4-yl | —CH$_2$— |
| 117 | 2-(4-fluorophenyl)thiazol-4-yl | —CH$_2$— |
| 118 | 1-benzyl-1H-pyrazol-3-yl | —CH$_2$— |
| 119 | benzothiazol-2-yl | —CH$_2$— |

TABLE 1-continued

| No | W | L |
|---|---|---|
| 120 | 5-chloro-benzothiazol-2-yl | —CH₂— |
| 121 | 2-(pyridine-3-carboxamido)phenyl | —CH₂— |
| 122 | 2-(4-fluorobenzamido)phenyl | —CH₂— |
| 123 | 2-(4-chlorobenzamido)phenyl | —CH₂— |
| 124 | 2-(4-chloro-N-methylbenzamido)phenyl | —CH₂— |
| 125 | 2-(2-chloro-N-methylpyridine-3-carboxamido)phenyl | —CH₂— |
| 126 | 2-(3-(difluoromethyl)-1-methyl-1H-pyrazole-4-carboxamido)phenyl | —CH₂— |

TABLE 1-continued $$\underset{W}{\overset{}{\diagdown}}L\underset{}{\overset{}{\diagdown}}O\underset{}{\overset{}{\diagdown}}N\underset{}{\overset{CN}{\diagup}}\underset{CN}{\diagdown}$$ I

| No | W | L |
|---|---|---|
| 127 | (3-difluoromethyl-1-methyl-1H-pyrazol-4-yl)-C(O)-N(CH₃)-(2-substituted phenyl) | —CH₂— |
| 128 | (3-trifluoromethyl-1-methyl-1H-pyrazol-4-yl)-C(O)-NH-(2-substituted phenyl) | —CH₂— |
| 129 | (3-trifluoromethyl-1-methyl-1H-pyrazol-4-yl)-C(O)-N(CH₂-cyclopropyl)-(2-substituted phenyl) | —CH₂— |
| 130 | (4-isobutylphenyl)-CH(CH₃)-C(O)-NH-(2-substituted phenyl) | —CH₂— |
| 131 | F₃HCF₂HCF₂HC-C(O)-NH-(2-substituted phenyl) | —CH₂— |
| 132 | CH₃-C(O)-NH-(2-substituted phenyl) | —CH₂— |
| 133 | (4-trifluoromethyl-2-methyl-thiazol-5-yl)-C(O)-NH-(2-substituted phenyl) | —CH₂— |

TABLE 1-continued $$\underset{W}{\overset{}{\diagdown}} L \underset{\diagup}{\overset{O}{\diagdown}} N \underset{\diagdown}{\overset{CN}{\diagup}} CN \quad I$$

| No | W | L |
|---|---|---|
| 134 | *2-methylbenzamide-phenyl* | —CH₂— |
| 135 | *2-iodobenzamide-phenyl* | —CH₂— |
| 136 | *2-trifluoromethylbenzamide-phenyl* | —CH₂— |
| 137 | *2-trifluoromethyl-6-fluorobenzamide-phenyl* | —CH₂— |
| 138 | *N-phenyl-4-methyl-1,2,3-thiadiazole-5-carboxamide* | —CH₂— |
| 139 | *3-(difluoromethyl)-5-chloro-1-methyl-N-methyl-N-phenylpyrazole-4-carboxamide* | —CH₂— |
| 140 | *1,3,5-trimethyl-N-phenylpyrazole-4-carboxamide* | —CH₂— |

TABLE 1-continued
$$\underset{W}{\overset{}{\bigvee}}L\overset{}{\diagdown}O\overset{}{\diagdown}N\overset{CN}{\diagup}$$
I
| No | W | L |
|----|---|---|
| 141 | 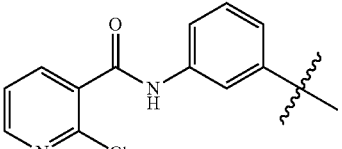 | —CH$_2$— |
| 142 | 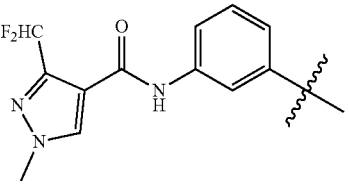 [SMILES: *c1cccc(NC(=O)c2cn(C)nc2C(F)F)c1] | —CH$_2$— |
| 143 | 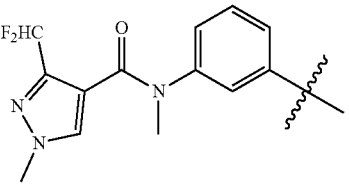 [SMILES: *c1cccc(N(C)C(=O)c2cn(C)nc2C(F)F)c1] | —CH$_2$— |
| 144 | 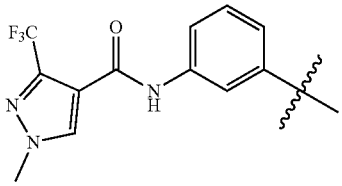 [SMILES: *c1cccc(NC(=O)c2cn(C)nc2C(F)(F)F)c1] | —CH$_2$— |
| 145 | 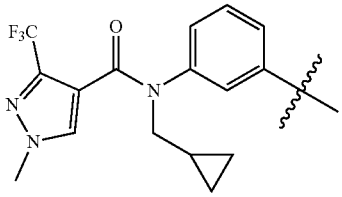 [SMILES: *c1cccc(N(CC2CC2)C(=O)c2cn(C)nc2C(F)(F)F)c1] | —CH$_2$— |
| 146 | 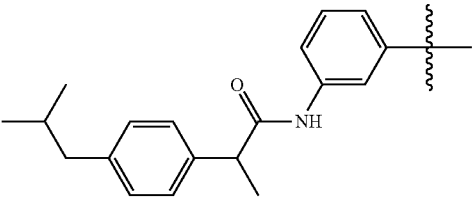 [SMILES: *c1cccc(NC(=O)C(C)c2ccc(CC(C)C)cc2)c1] | —CH$_2$— |
| 147 | 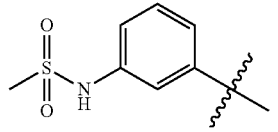 [SMILES: *c1cccc(NS(C)(=O)=O)c1] | —CH$_2$— |
| 148 | 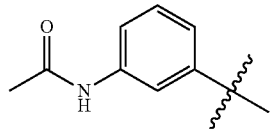 [SMILES: *c1cccc(NC(C)=O)c1] | —CH$_2$— |

TABLE 1-continued $$\underset{\text{W}}{\text{W}}\overset{}{\text{L}}\overset{}{\text{O}}\overset{}{\text{N}}\overset{\text{CN}}{\underset{\text{CN}}{\diagdown}}$$ I

| No | W | L |
|---|---|---|
| 149 | 3-(trifluoromethyl)-2-methyl-thiazole-5-carboxamide-N-(3-phenyl) | —CH₂— |
| 150 | 2-methyl-pyridine-3-carboxamide-N-(3-phenyl) | —CH₂— |
| 151 | 2-iodo-benzamide-N-(3-phenyl) | —CH₂— |
| 152 | 2-(trifluoromethyl)-benzamide-N-(3-phenyl) | —CH₂— |
| 153 | 2-(trifluoromethyl)-6-fluoro-benzamide-N-(3-phenyl) | —CH₂— |
| 154 | 4-methyl-1,2,3-thiadiazole-5-carboxamide-N-(3-phenyl) | —CH₂— |
| 155 | 3-(difluoromethyl)-5-chloro-1-methyl-pyrazole-4-carboxamide-N-ethyl-N-(3-phenyl) | —CH₂— |
| 156 | 1,3,5-trimethyl-pyrazole-4-carboxamide-N-(3-phenyl) | —CH₂— |

TABLE 1-continued
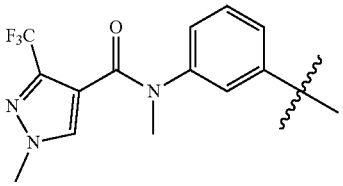 [SMILES: *c1cccc(N(C)C(=O)c2cn(C)nc2C(F)(F)F)c1]
| No | W | L |
|---|---|---|
| 157 |  | —CH₂— |
| 158 | 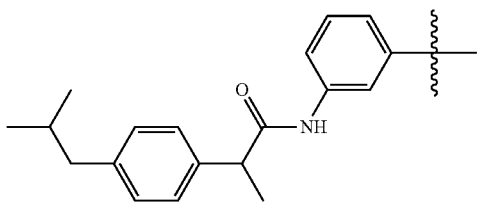 | —CH₂— |
| 159 |  | —CH₂— |
| 160 | 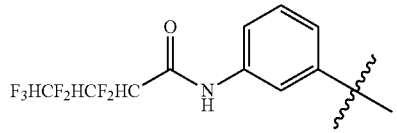 | —CH₂— |
| 161 |  | —CH₂— |
| 162 | 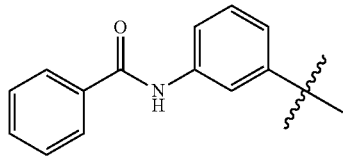 [SMILES: *c1cccc(NC(=O)c2ccccc2)c1] | —CH₂— |
| 163 |  | —CH₂— |
| 164 | 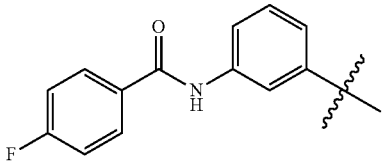 [SMILES: *c1cccc(NC(=O)c2ccc(F)cc2)c1] | —CH₂— |

TABLE 1-continued structure I: W−L−O−N=C(CN)(CN)

| No  | W | L |
|-----|---|---|
| 165 | 3-(difluoromethyl)-1-methyl-N-(2-chloro-3-attachment-phenyl)-1H-pyrazole-4-carboxamide | —CH₂— |
| 166 | 3-(difluoromethyl)-1-methyl-N-(2-fluoro-3-attachment-phenyl)-1H-pyrazole-4-carboxamide | —CH₂— |
| 167 | 3-(difluoromethyl)-1-methyl-N-(3-attachment-benzyl)-1H-pyrazole-4-carboxamide | —CH₂— |
| 168 | N-(3-attachment-phenyl)-N',N'-dimethylsulfamide | —CH₂— |
| 169 | 3-(difluoromethyl)-5-chloro-1-methyl-N-(4-attachment-phenyl)-1H-pyrazole-4-carboxamide | —CH₂— |
| 170 | 1,3,5-trimethyl-N-(4-attachment-phenyl)-1H-pyrazole-4-carboxamide | —CH₂— |

TABLE 1-continued
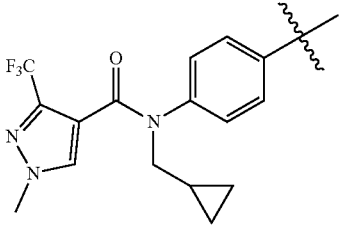 [SMILES: *c1ccc(N(CC2CC2)C(=O)c2cn(C)nc2C(F)(F)F)cc1]
I
| No | W | L |
|---|---|---|
| 171 |  | —CH₂— |
| 172 |  | —CH₂— |
| 173 | 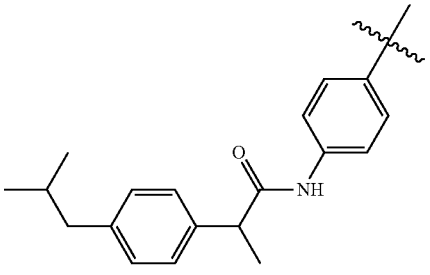 [SMILES: *c1ccc(NC(=O)C(C)c2ccc(CC(C)C)cc2)cc1] | —CH₂— |
| 174 |  | —CH₂— |
| 175 |  | —CH₂— |
| 176 | 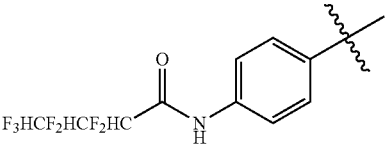 | —CH₂— |

TABLE 1-continued $$\underset{\text{W}}{\overset{\text{}}{\diagdown}}\text{L}\underset{\text{}}{\overset{\text{O}}{\diagdown}}\text{N}\underset{\text{CN}}{\overset{\text{CN}}{\diagup}}\quad\text{I}$$

| No | W | L |
|---|---|---|
| 177 | 4-chloro-N-methyl-N-(4-yl-phenyl)benzamide | —CH₂— |
| 178 | N-(4-yl-phenyl)acetamide | —CH₂— |
| 179 | 2-methyl-4-(trifluoromethyl)-N-(4-yl-phenyl)thiazole-5-carboxamide | —CH₂— |
| 180 | 2-methyl-N-(4-yl-phenyl)benzamide | —CH₂— |
| 181 | 2-iodo-N-(4-yl-phenyl)benzamide | —CH₂— |
| 182 | 2-(trifluoromethyl)-N-(4-yl-phenyl)benzamide | —CH₂— |
| 183 | 4-yl-N-phenylbenzamide | —CH₂— |

TABLE 1-continued $$\underset{W}{\diagdown}L\diagup O\diagdown N\diagup\diagdown_{CN}^{CN}\quad I$$

| No | W | L |
|---|---|---|
| 184 | 3-(phenylcarbamoyl)phenyl (N-phenyl benzamide, meta-attached) | —CH$_2$— |
| 185 | 4-[N-methyl-N-phenylcarbamoyl]phenyl | —CH$_2$— |
| 186 | 3-[N-methyl-N-(4-chlorophenyl)carbamoyl]phenyl | —CH$_2$— |
| 187 | 4-[(3,4,5-trifluorophenyl)carbamoyl]phenyl | —CH$_2$— |
| 188 | 4-[(3-isopropoxyphenyl)carbamoyl]phenyl | —CH$_2$— |
| 189 | 2-[(3-isopropoxyphenyl)carbamoyl]phenyl | —CH$_2$— |
| 190 | 3-[(3-isopropoxyphenyl)carbamoyl]phenyl | —CH$_2$— |

TABLE 1-continued $$\text{W}\diagdown\text{L}\diagdown\text{O}\diagdown\text{N}=\text{C}(\text{CN})_2 \quad \text{I}$$

| No | W | L |
|---|---|---|
| 191 | N-methyl-N-(3-isopropoxyphenyl)-4-benzamide | —CH₂— |
| 192 | N-methyl-N-(3-isopropoxyphenyl)-2-benzamide | —CH₂— |
| 193 | N-methyl-N-(3-isopropoxyphenyl)-3-benzamide | —CH₂— |
| 194 | N-(2,2,2-trifluoroethyl)-4-benzamide | —CH₂— |
| 195 | N-methyl-3-benzamide | —CH₂— |
| 196 | N-methoxy-N-methyl-3-benzamide | —CH₂— |
| 197 | N-methoxy-N-methyl-4-benzamide | —CH₂— |
| 198 | N-(cyanomethyl)-4-benzamide | —CH₂— |

TABLE 1-continued $$\text{W} - \text{L} - \text{O} - \text{N} = \text{C}(\text{CN})_2 \quad \text{I}$$

| No | W | L |
|---|---|---|
| 199 | 3-(NCCH₂NHC(O))-phenyl | —CH₂— |
| 200 | 4-(MeO(Me)NC(O))-phenyl | —CH₂— |
| 201 | 4-(PhN(Me)SO₂)-phenyl | —CH₂— |
| 202 | 6-methoxybenzothiazol-2-yl | —NH—(C=O)—CH₂— |
| 203 | quinolin-6-yl | —CH₂— |
| 204 | 4'-((NC)₂C=N-O-CH₂)-biphenyl-4-yl | —CH₂— |
| 205 | 2'-cyanobiphenyl-4-yl | —CH₂— |
| 206 | 2-((NC)₂C=N-O-CH₂)-phenyl | —CH₂— |

TABLE 1-continued
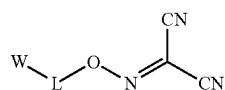
I
| No | W | L |
|---|---|---|
| 207 | benzimidazol-2-yl | —CH₂— |
| 208 | 3-(2,2,2-trifluoroethylcarbamoyl)phenyl | —CH₂— |
| 209 | phenyl | —CH₂—CH₂— |
| 210 | 4-nitrophenyl | —O—CH₂—CH₂— |
| 211 | 3-[N-(3,4-dimethoxyphenyl)-N-(tert-butoxycarbonyl)carbamoyl]phenyl | —CH₂— |
| 212 | 3-[N-(2,6-dimethyl-4-(1,2,2,2-tetrafluoro-1-(trifluoromethyl)ethyl)phenyl)carbamoyl]phenyl | —CH₂— |
| 213 | 3-[N-(4'-chlorobiphenyl-2-yl)carbamoyl]phenyl | —CH₂— |

TABLE 1-continued
I
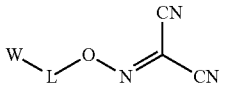
| No | W | L |
|---|---|---|
| 214 | 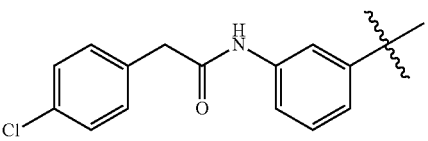 [SMILES: *c1cccc(NC(=O)Cc2ccc(Cl)cc2)c1] | —CH$_2$— |
| 215 | 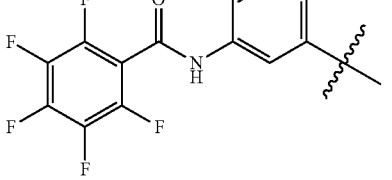 | —CH$_2$— |
| 216 | 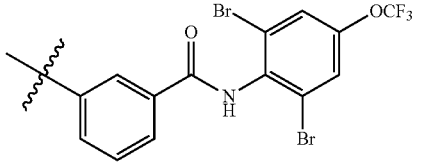 [SMILES: *c1cccc(C(=O)Nc2c(Br)cc(OC(F)(F)F)cc2Br)c1] | —CH$_2$— |
| 217 | 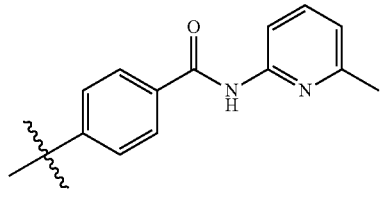 [SMILES: *c1ccc(C(=O)Nc2cccc(C)n2)cc1] | —CH$_2$— |
| 218 | 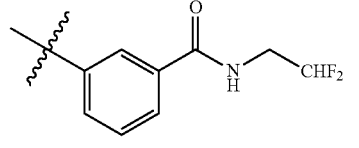 [SMILES: *c1cccc(C(=O)NCC(F)F)c1] | —CH$_2$— |
| 219 | 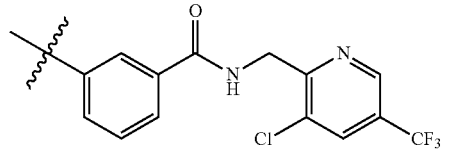 [SMILES: *c1cccc(C(=O)NCc2ncc(C(F)(F)F)cc2Cl)c1] | —CH$_2$— |
| 220 | 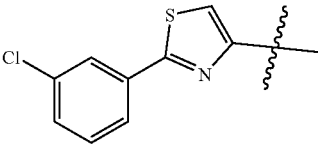 [SMILES: *c1csc(-c2cccc(Cl)c2)n1] | —CH$_2$— |
| 221 |  | —CH$_2$— |

TABLE 1-continued
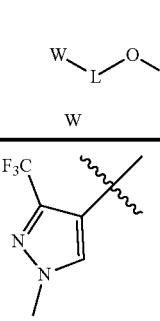
| No | W | L |
|---|---|---|
| 222 |  | —CH₂— |
| 223 | 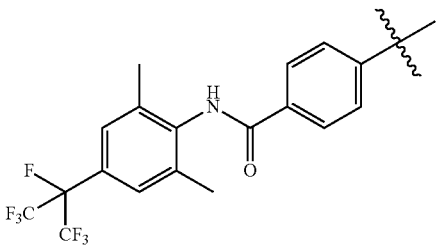 [SMILES: *c1ccc(C(=O)Nc2c(C)cc(C(F)(C(F)(F)F)C(F)(F)F)cc2C)cc1] | —CH₂— |
| 224 |  | —CH₂— |
| 225 | 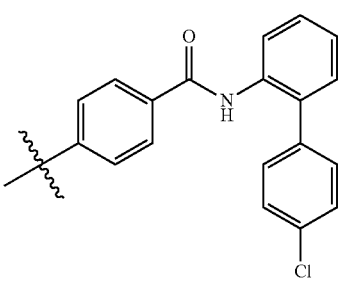 [SMILES: *c1ccc(C(=O)Nc2ccccc2-c2ccc(Cl)cc2)cc1] | —CH₂— |
| 226 |  | —CH₂— |
| 227 | 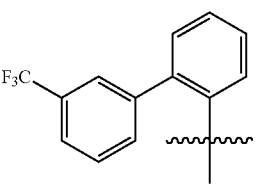 [SMILES: *c1ccccc1-c1cccc(C(F)(F)F)c1] | —CH₂— |
| 228 |  | —CH₂— |

TABLE 1-continued

| No | W | L |
|---|---|---|
| 229 | 4-(N-(2,2-difluoroethyl)carbamoyl)phenyl | —CH₂— |
| 230 | 4-(N-((3-chloro-5-(trifluoromethyl)pyridin-2-yl)methyl)carbamoyl)phenyl | —CH₂— |
| 231 | 2-(3-fluorophenyl)thiazol-4-yl | —CH₂— |
| 232 | 2-(2-fluorophenyl)thiazol-4-yl | —CH₂— |
| 233 | 4-((3-chloro-5-(trifluoromethyl)pyridin-2-yl)oxy)phenyl | —CH₂— |
| 234 | pyridazin-3-yl | —CH₂— |
| 235 | 4H-1,2,4-triazol-3-yl | —CH₂— |
| 236 | 1,2,5-thiadiazol-3-yl | —CH₂— |
| 237 | benzo[d]thiazol-5-yl | —CH₂— |

TABLE 1-continued

![Structure I: W-L-O-N=C(CN)(CN)]  I

| No | W | L |
|---|---|---|
| 238 | (naphthalen-2-yl) | —CH₂— |
| 239 | (4-(pyridin-2-yloxy)phenyl) | —CH₂— |
| 240 | (1-acetyl-1H-imidazol-5-yl) | —CH₂— |
| 241 | (1,2,3-thiadiazol-4-yl) | —CH₂— |
| 242 | (1H-indol-6-yl) | —CH₂— |
| 243 | (1H-benzimidazol-5-yl) | —CH₂— |
| 244 | (naphthalen-1-yl) | —CH₂— |
| 245 | (4-(2,4-dichlorophenoxy)phenyl) | —CH₂— |
| 246 | (4-((5-(trifluoromethyl)pyridin-2-yl)oxy)phenyl) | —CH₂— |

TABLE 1-continued
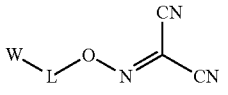
| No | W | L |
|---|---|---|
| 247 | 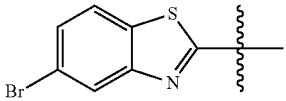 | —CH₂— |
| 248 | 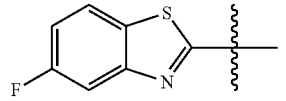 [SMILES: *c1nc2cc(F)ccc2s1] | —CH₂— |
| 249 | 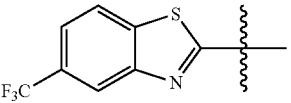 | —CH₂— |
| 250 | 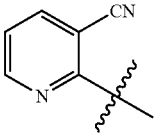 [SMILES: *c1ncccc1C#N] | —CH₂— |
| 251 | 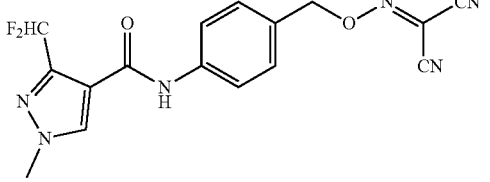 | —CH₂— |
| 252 | 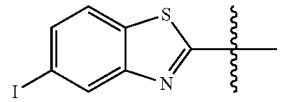 [SMILES: *c1nc2cc(I)ccc2s1] | —CH₂— |
| 253 | 3,4-diBr—Ph | —CH₂— |
| 254 | 3,4-diI—Ph | —CH₂— |
| 255 | 3-F-4-Cl—Ph | —CH₂— |
| 256 | 3-Br-4-Cl—Ph | —CH₂— |
| 257 | 3-I-4-Cl—Ph | —CH₂— |
| 258 | 3-Cl-4-F—Ph | —CH₂— |
| 259 | 3-Cl-4-Br—Ph | —CH₂— |
| 260 | 3-Cl-4-I—Ph | —CH₂— |
| 261 | 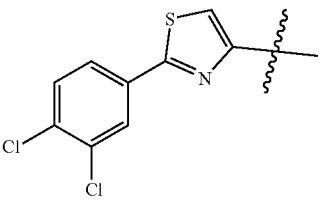 [SMILES: *c1csc(-c2ccc(Cl)c(Cl)c2)n1] | —CH₂— |
| 262 | 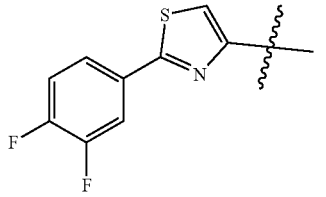 [SMILES: *c1csc(-c2ccc(F)c(F)c2)n1] | —CH₂— |

TABLE 1-continued

I

W-L-O-N=C(CN)₂

| No | W | L |
|---|---|---|
| 263 | 3,4-dibromophenyl-thiazol-4-yl | —CH₂— |
| 264 | 2,6-difluorophenyl-thiazol-2-yl | —CH₂— |
| 265 | 3-chloro-4-fluorophenyl-thiazol-4-yl | —CH₂— |
| 266 | 4-chloro-3-fluorophenyl-thiazol-4-yl | —CH₂— |
| 267 | 4-bromophenyl-thiazol-4-yl | —CH₂— |
| 268 | 3-bromo-4-chlorophenyl-thiazol-4-yl | —CH₂— |

¹H NMR (300 MHz, CDCl₃) data and physical properties of some representative compounds are as follows:

TABLE 2

| No | compound | ¹H NMR | physical properities |
|---|---|---|---|
| 1 | 3 | 5.48(s, 2H), 7.28-7.43(m, 4H). | yellow oil |
| 2 | 4 | 5.48(s, 2H), 7.34(d, 2H), 7.41(dd, 2H). | yellow oil |
| 3 | 5 | 5.60(s, 2H), 7.04-7.47(m, 4H), | yellow oil |
| 4 | 7 | 5.61(s, 2H), 7.09-7.15(m, 2H), 7.37-7.41(m, 2H). | yellow oil |

TABLE 2-continued

| No | compound | ¹H NMR | physical properties |
|---|---|---|---|
| 5 | 9 | 5.47(s, 2H), 7.30-7.32(t, 2H), 7.53-7.58(m, 2H). | white solid |
| 6 | 19 | 3.83(s, 3H), 5.46(s, 2H), 6.93(dd, 2H), 6.93(dd, 2H), 7.33(dd, 2H). | colourless oil |
| 7 | 22 | 5.59(s, 2H), 7.52(d, 2H), 7.71(d. 2H). | colourless oil |
| 8 | 23 | 5.62(s, 2H), 7.26-7.39(m, 2H), 7.45-7.50(m, 2H). | yellow oil |
| 9 | 25 | 5.52(s, 2H), 7.28(d, 2H), 7.44(d, 2H). | white solid |
| 10 | 32 | 6.00(s, 2H), 7.55-7.63(m, 2H), 7.75(t, 1H), 8.22(d, 1H). | yellow oil |
| 11 | 34 | 5.63(s, 2H), 7.58(d, 2H), 8.30(dd, 2H). | yellow solid |
| 12 | 36 | 5.54(s, 2H), 7.54-7.74(m, 3H). | yellow oil |
| 13 | 37 | 5.57(s, 2H), 7.51(d, 2H), 7.75(d, 2H). | white solid |
| 14 | 53 | 5.53(s, 2H), 7.43(d, 2H), 7.72(dd, 1H), 8.46(d, 1H). | yellow solid |
| 15 | 58 | 5.88(s, 2H), 7.34-7.42(m, 3H). | yellow oil |
| 16 | 59 | 5.46(s, 2H), 7.22-7.25(m, 1H), 7.49-7.53(m, 2H). | yellow solid |
| 17 | 60 | 5.45(s, 2H), 7.27(d, 2H), 7.43(t, 1H). | yellow oil |
| 18 | 81 | 5.64(s, 2H), 7.45-7.55(m, 3H). | yellow solid |
| 19 | 83 | 5.46(s, 2H), 7.15-7.27(m, 3H). | yellow oil |
| 20 | 85 | 5.66(s, 2H), 6.98(t, 2H), 7.44(m, 1H). | yellow oil |
| 21 | 86 | 5.52(s, 2H), 7.02-7.05(m, 1H), 7.23-7.28(m, 1H). | yellow oil |
| 22 | 91 | 3.94(s, 3H), 5.57(s, 2H), 7.45(d, 2H), 8.09(d, 2H). | yellow oil |
| 23 | 93 | 5.48(s, 2H), 7.01-7.47(m, 9H). | yellow oil |
| 24 | 96 | 5.48(s, 2H), 7.29-7.49(m, 9H). | yellow oil |
| 25 | 102 | 2.26(s, 3H), 5.65(s, 2H), 7.27-7.45(m, 8H). | yellow solid |
| 26 | 103 | 4.59(d, 2H), 5.52(s, 2H), 7.28(d, 2H), 7.46(d, 2H). | yellow oil |
| 27 | 104 | 5.65(s, 4H), 7.46-7.54(m, 4H). | yellow oil |
| 28 | 106 | 2.41(s, 6H), 2.44(s, 3H), 5.69(s, 4H), 7.03(s, 1H). | white solid |
| 29 | 107 | 5.62(s, 2H), 7.66(s, 1H). | brown oil |
| 30 | 109 | 3.72(s, 3H), 3.85(s, 3H), 5.45(s, 2H), 7.20-7.22(t, 1H), 7.38-7.43(m, 2H), 7.63(s, 1H). | yellow oil |
| 31 | 110 | 3.91(s, 3H), 4.07(s, 3H), 5.39(s, 2H), 7.46-7.51(m, 3H). | yellow oil |
| 32 | 111 | 3.74(s, 3H), 3.83(s, 3H), 5.60(s, 2H), 7.44-7.46(m, 4H). | yellow oil |
| 33 | 112 | 5.59(s, 2H), 7.50-7.63(m, 5H), 7.80-7.87(m, 4H). | yellow oil |
| 34 | 113 | 5.61(s, 2H), 7.49-7.53(m, 4H), 7.60-7.63(m, 1H), 7.80-7.87(m, 4H). | yellow solid |
| 35 | 114 | 5.74(s, 2H), 7.47-7.56(m, 5H), 7.61-7.64(m, 2H), 7.78-7.80(m, 2H). | yellow solid |
| 36 | 115 | 5.68(s, 2H), 7.40(s, 1H), 7.44-7.47(m, 3H), 7.93-7.97(m, 2H). | yellow solid |
| 37 | 116 | 5.67(s, 2H), 7.42-7.45(d, 3H), 7.88-7.91(d, 2H). | white solid |
| 38 | 118 | 5.31(s, 2H), 5.41(s, 2H), 7.24(s, 2H), 7.36-7.38(d, 3H), 7.49(s, 1H), 7.62(s, 1H). | yellow oil |
| 39 | 119 | 5.90(s, 2H), 7.48-7.56(m, 2H), 7.93-7.96(m, 1H), 8.10(d, 1H). | red oil |
| 40 | 120 | 5.90(s, 2H), 7.44-7.48(m, 1H), 7.86(d, 1H). 8.07(d, 3H). | red solid |
| 41 | 122 | 5.61(s, 2H), 7.18-7.32(m, 3H), 7.42-7.52(m, 2H), 7.85-7.87(d, 1H), 7.91-7.96(m, 2H). | white solid |
| 42 | 126 | 4.12(s, 3H). 5.60(s, 2H) 7.29-7.34(m, 1H), 7.42-7.60(m, 3H), 7.73-7.82(m, 3H). | yellow solid |
| 43 | 142 | 3.97(s, 3H), 5.53(s, 2H), 7.18-7.79(m, 6H). | yellow solid |
| 44 | 147 | 5.53(s, 2H), 7.27-7.30(t, 1H), 7.45-7.50(t, 1H), 7.59-7.61(t, 1H), 7.70(s, 1H). | yellow solid |
| 45 | 164 | 2.33(s, 3H), 4.13(s, 3H), 5.62(s, 2H), 7.25-7.78(m, 5H). | yellow solid |
| 46 | 167 | 4.09(s, 3H), 4.62(d, 2H), 5.52(s, 2H), 6.33(s, 1H), 7.32-7.83(m, 6H) | yellow solid |
| 47 | 185 | 3.51(s, 3H), 5.42(s, 2H), 7.03(s, 1H), 7.05(s, 1H), 7.16-7.27(m, 5H), 7.33-7.36(2H). | yellow solid |
| 48 | 201 | 3.21(s, 3H), 5.58(s, 2H), 7.09-7.13(m, 2H), 7.30-7.33(t, 3H), 7.45(d, 2H), 7.61(d, 2H). | white oil |
| 49 | 202 | 3.89(d, 3H), 5.27(s, 2H), 7.07-7.11(m, 1H), 7.30-7.31(d, 1H), 7.65-7.69(m, 1H). | yellow solid |
| 50 | 203 | 5.72(s, 2H), 7.48-7.52(m, 1H), 7.71-7.74(m, 1H), 7.87(s, 1H), 8.17-8.25(m, 2H), 8.99(d, 2H). | brown oil |
| 51 | 204 | 5.57(s, 4H), 7.48(s, 4H), 7.65(s, 4H). | while solid |
| 52 | 205 | 5.59(s, 2H), 7.46-7.54(m, 4H), 7.61-7.68(m, 3H), 7.78-7.80(d, 1H). | yellow solid |
| 53 | 206 | 5.65(s, 4H), 7.46-7.55(m, 4H). | colourless oil |
| 54 | 208 | 4.16(t, 2H), 5.57(s, 2H), 7.55-7.58(m, 2H), 7.84-7.86(m, 2H). | yellow oil |
| 55 | 209 | 3.72(t, 2H), 4.76(t, 2H), 7.20-7.34(m, 5H). | yellow oil |
| 56 | 210 | 4.42(dd, 2H), 4.94-4.97(m, 2H), 7.0(dd, 2H), 8.24(dd, 2H). | while solid |
| 57 | 212 | 2.35(s, 6H), 5.60(s, 2H), 7.37(s, 1H), 7.48(s, 1H), 7.61(d, 1H), 7.97(d, 1H). | yellow oil |
| 58 | 213 | 5.52(s, 2H), 7.28-7.59(m, 5H), 7.71(s, 2H), 7.82(s, 2H), 8.41(d, 1H). | yellow solid |
| 59 | 215 | 3.73(s, 2H), 5.48(s, 2H), 7.11-7.14(m, 3H), 7.28-7.41(m, 4H), 7.61(s, 1H). | yellow solid |
| 60 | 218 | 2.48(s, 3H), 5.59(s, 2H), 6.96(d, 1H), 7.51(d, 2H), 7.66(t, 1H), 7.99(dd, 2H), 8.18(d, 1H), 8.57(s, 1H). | yellow oil |
| 61 | 220 | 4.93(d, 2H), 5.60(s, 2H), 7.56-7.58(t, 2H), 7.94-8.00(m, 3H), 8.79(s, 1H). | yellow oil |
| 62 | 221 | 5.68(s, 2H), 7.40-7.45(m, 3H), 7.80-7.83(m, 1H), 7.96(d, 1H) | brown oil |
| 63 | 223 | 2.34(s, 6H), 5.60(s, 2H), 7.37(s, 1H), 7.52(t, 2H), 7.96-7.99(d, 2H). | yellow solid |
| 64 | 222 | 3.40(s, 3H), 5.51(s, 2H), 7.59(s, 1H) | yellow oil |
| 65 | 225 | 5.43(s, 2H), 7.36-7.70(m, 8H). | yellow oil |
| 66 | 226 | 5.55(s, 2H), 7.23-7.90(m, 4H), 8.31(d, 1H), 8.77(s, 1H). | yellow solid |
| 67 | 228 | 2.47(s, 3H), 5.58(s, 2H), 6.96(d, 1H), 7.56-7.70(m, 3H), 7.97-7.99(m, 2H), 8.19(d, 1H). | yellow solid |
| 68 | 229 | 3.81-3.92(m, 2H), 5.57(d, 2H), 5.98(m, 1H), 7.48(d, 2H), 7.85(d, 2H). | yellow oil |
| 69 | 230 | 4.93(d, 2H), 5.59(s, 2H), 7.50(d, 2H), 7.80(s, 1H), 7.96-7.99(m, 3H), 8.77(s, 1H). | yellow solid |
| 70 | 233 | 5.55(s, 2H), 7.24(d, 2H), 7.48(d, 2H), 8.01(d, 2H), 8.28(d, 2H) | yellow oil |
| 71 | 250 | 5.85(s, 2H), 7.51-7.55(m, 1H), 8.08-8.11(m, 1H), 8.86-8.88(m, 1H). | yellow solid |
| 72 | 251 | 4.12(s, 3H), 5.50(s, 2H), 7.39-7.80(m, 6H). | yellow solid |

The compounds of general formula I in the present disclosure can be prepared by the following methods, unless further specification, the substituents in the reaction schemes are the same as above definitions:

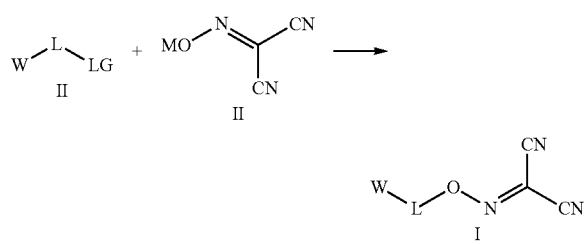

Intermediates II and III are reacted in appropriate solvent to yield the compounds of the general formula I at a certain temperature from −10° C. to boiling point for 30 minutes to 48 hours. The suitable solvent is selected from dichloromethane, chloroform, tetrachloride, hexane, benzene, toluene, methanol, ethanol, ethyl acetate, acetonitrile, dioxane, tetrahydrofuran, N,N-dimethylformamide, dimethyl sulfoxide, etc.

In the preparation method above: LG represents a leaving group, suitable leaving groups can be selected in the list consisting of a halogen atom or other customary nucleofugal groups such as triflate, mesylate or tosylate. M means cation, such as $Na^+$, $K^+$, $CS^+$, $Ag^+$, $NH_4^+$, etc.

Intermediate II are commercially available or can be prepared according to the following methods described in *European Journal of Inorganic Chemistry*, 2014(5), 888-895, 2014 or *Asian Journal of Chemistry*, 20(2), 1425-1430, 2008, etc. (the definition of each substituent is as defined above unless otherwise stated.)

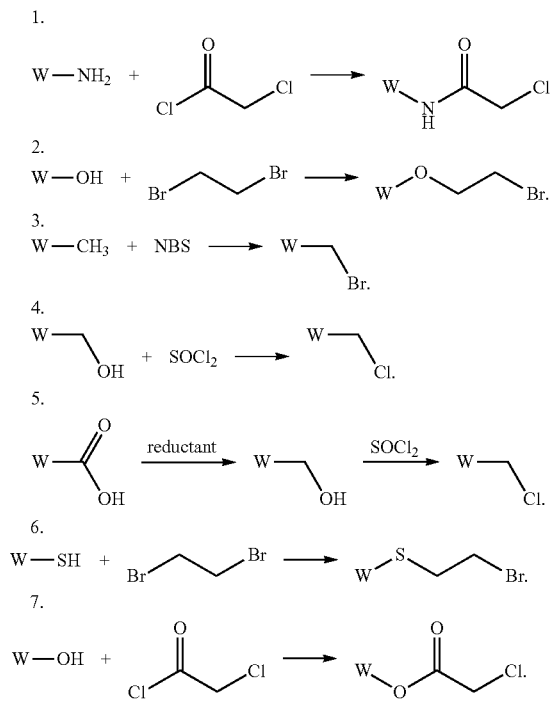

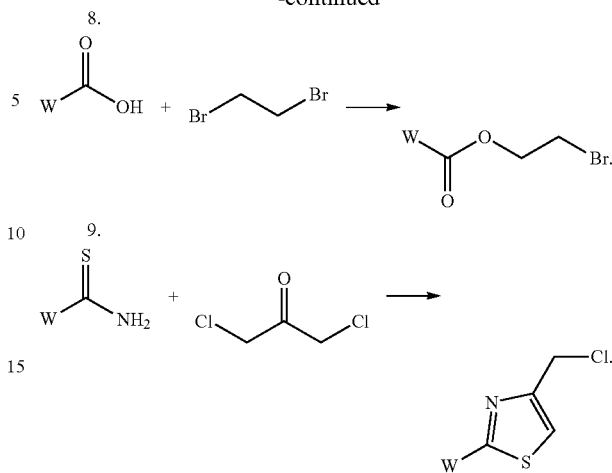

Intermediate III can be prepared according to the methods described in CN103804321, WO2008139481, US20130096098, *Journal of the Chemical Society of Pakistan*, 33(3), 324-332, 2011, etc.

The compounds of formula I according to the invention can be used to control the fungal diseases caused by oomycetes, basidiomycetes, ascomycetes, deuteromycetes, etc. The active compounds show good activity at low dosages against cucumber downy mildew, cucumber gray mold, cucumber anthracnose, cucumber powdery mildew, tomato early blight, tomato late blight, pepper blight, grape downy mildew, grape white rot, apple ring rot, *alternaria* leaf spot of apple, rice sheath blight, rice blast, wheat rust, wheat leaf spot, wheat powdery mildew, *sclerotia sclerotium*, southern leaf blight of corn, etc.

The compounds of formula I according to the invention show good bactericidal activity and also can be used to control various plant bacterial diseases, such as bacterial wilt, bacterial blight, canker, soft rot, bacterial angular leaf spot, bacterial leaf streak, bacterial leaf blight, wildfire, bacterial scab, etc.

The present invention also includes to a fungicidal\bactericidal compositions containing the compounds having general formula I as active ingredient, and the weight percentage of the active ingredient in the composition is 0.1-99%. The fungicidal\bactericidal compositions also include the carrier being acceptable in agriculture.

According to the invention, there is also provided a method of preparing the composition defined above: the compounds having formula I is mixed with carrier(s). The composition according to the invention can contain a single compound of the present invention or a mixture of several compounds of the present invention.

A carrier in a composition according to the present invention is any material satisfied with the following conditions: the carrier with the active ingredient is formulated to facilitated to the locus to be treated, which may for example be a plant, seed, or soil, or to facilitate storage, transport or handling. A carrier may be a solid or a liquid, including material which is normally a gas but which has been compressed to form a liquid. are generally used in the formulation of insecticidal, bactericidal compositions. The carriers usually used in the formulation of insecticidal and fungicidal compositions can be used.

Suitable solid carriers include natural or synthetic clays or natural or synthetic silicates, such as diatomite, talc, attapulgite, aluminum silicate (kaolin), montmorillonite, mica; calcium carbonate; calcium sulfate; ammonium sulfate; synthetic monox, synthetic calcium silicate or synthetic aluminum silicate; element such as carbon, sulfur; natural or synthetic resins such as benzofuran resins, polyvinyl chloride, styrene polymers or copolymers; solid polychlorophenol; asphalt; wax such as beeswax, paraffin.

Suitable liquid carriers include water; alcohol such as isopropanol, ethanol; ketone such as acetone, methyl ethyl ketone, methyl isopropyl ketone, cyclohexyl ketone; ether; aromatic hydrocarbons such as benzene, toluene, xylene; petroleum fraction, such as kerosene, mineral oil; chlorinated hydrocarbons such as carbon tetrachloride, perchlorethylene, trichlorethylene. Mixtures of different liquids are often suitable.

DETAILED DESCRIPTION OF THE INVENTION

The following examples are illustrative of the present invention, but without being restricted thereby.

PREPARATION EXAMPLE

Example 1: The Preparation of Compound 4

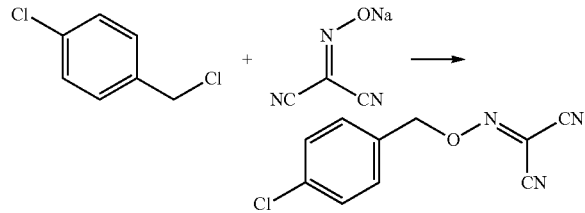

To a solution of malononitrile oxime ether sodium salt (0.22 g, 1.86 mmol) dissolved in 15 mL acetonitrile in a 50 mL reaction flask was added p-chlorobenzyl chloride (0.3 g, 1.86 mmol). The reaction was stirred at room temperature, and monitored by Thin-Layer Chromatography (ethyl acetate:petroleum ether=1:8) until the reaction was over, the excessive acetonitrile was evaporated under reduced pressure, the residual was purified by column chromatography on silica gel (eluent: ethyl acetate:petroleum ether=1:10; silica gel: 100-140 mesh, Qingdao Marine Chemical Co., Ltd.) to obtain the title compound 4 (0.21 g) as yellow oil with yield of 51%.

Example 2: The Preparation of Compound 25

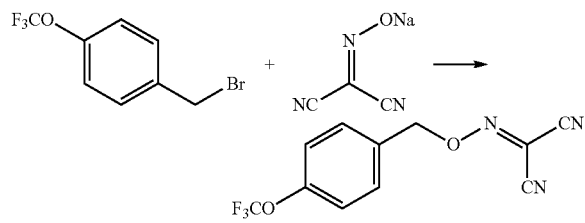

To a solution of malononitrile oxime ether sodium salt (0.12 g, 0.98 mmol) dissolved in 15 mL acetonitrile in a 50 mL reaction flask was added 1-(bromomethyl)-4-(trifluoromethoxy)benzene (0.25 g, 0.98 mmol). The reaction was stirred at room temperature, and monitored by Thin-Layer Chromatography (ethyl acetate:petroleum ether=1:8) until the reaction was over, the excessive acetonitrile was evaporated under reduced pressure, the residual was purified by column chromatography on silica gel (eluent: ethyl acetate:petroleum ether=1:10; silica gel: 100-140 mesh, Qingdao Marine Chemical Co., Ltd.) to obtain the title compound 25 (0.16 g) as white solid with yield of 61%.

Example 3: The Preparation of Compound 37

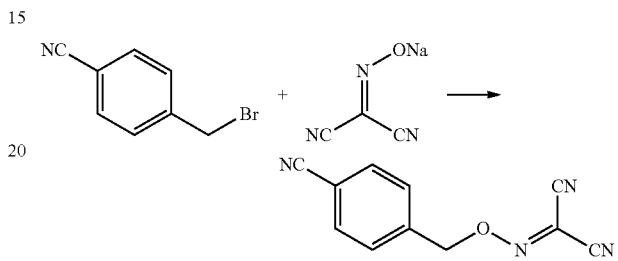

To a solution of malononitrile oxime ether sodium salt (0.18 g, 1.53 mmol) dissolved in 15 mL acetonitrile in a 50 mL reaction flask was added 4-(bromomethyl)benzonitrile (0.3 g, 1.53 mmol). The reaction was stirred at room temperature, and monitored by Thin-Layer Chromatography (ethyl acetate:petroleum ether=1:8) until the reaction was over, the excessive acetonitrile was evaporated under reduced pressure, the residual was purified by column chromatography on silica gel (eluent: ethyl acetate:petroleum ether=1:10; silica gel: 100-140 mesh, Qingdao Marine Chemical Co., Ltd.) to obtain the title compound 37 (0.18 g) as white solid with yield of 56%.

Example 4: The Preparation of Compound 53

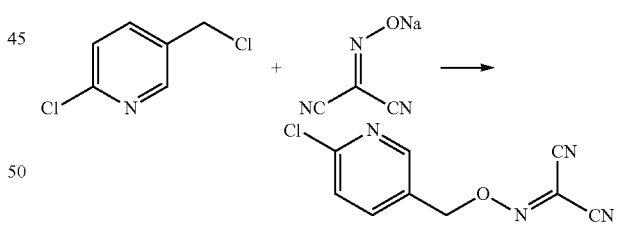

To a solution of malononitrile oxime ether sodium salt (0.25 g, 2.16 mmol) dissolved in 15 mL acetonitrile in a 50 mL reaction flask was added 2-chloro-5-(chloromethyl)pyridine (0.35 g, 2.16 mmol). The reaction was stirred at room temperature, and monitored by Thin-Layer Chromatography (ethyl acetate:petroleum ether=1:8) until the reaction was over, the excessive acetonitrile was evaporated under reduced pressure, the residual was purified by column chromatography on silica gel (eluent: ethyl acetate:petroleum ether=1:10; silica gel: 100-140 mesh, Qingdao Marine Chemical Co., Ltd.) to obtain the title compound 53 (0.21 g) as yellow solid with yield of 44%.

Example 5: The Preparation of Compound 59

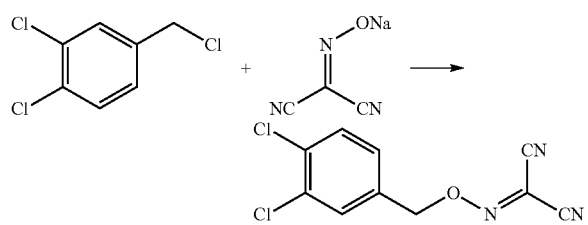

To a solution of malononitrile oxime ether sodium salt (0.18 g, 1.53 mmol) dissolved in 15 mL acetonitrile in a 50 mL reaction flask was added 1,2-dichloro-4-(chloromethyl)benzene (0.3 g, 1.53 mmol). The reaction was stirred at room temperature, and monitored by Thin-Layer Chromatography (ethyl acetate:petroleum ether=1:8) until the reaction was over, the excessive acetonitrile was evaporated under reduced pressure, the residual was purified by column chromatography on silica gel (eluent: ethyl acetate:petroleum ether=1:10; silica gel: 100-140 mesh, Qingdao Marine Chemical Co., Ltd.) to obtain the title compound 59 (0.22 g) as yellow solid with yield of 56%.

Example 6: The Preparation of Compound 96

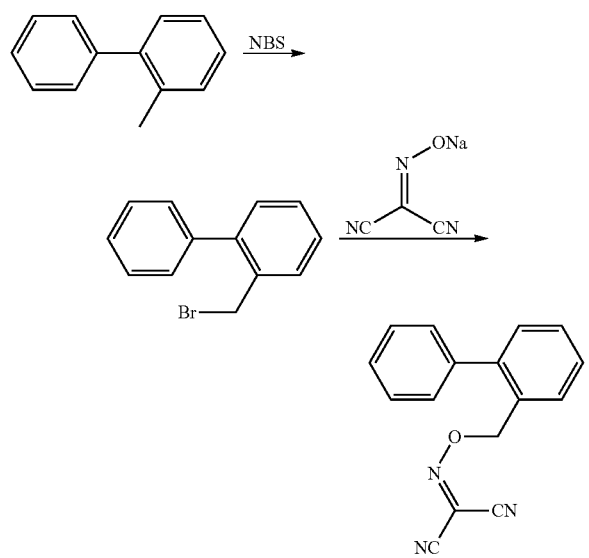

A mixture of 2-methyl-1,1'-biphenyl (0.8 g, 4.76 mmol), NBS (0.85 g, 4.76 mmol), AIBN (0.02 g) and tetrachloromethane (25 ml) was refluxed and monitored by Thin-Layer Chromatography until the reaction was over. The excessive tetrachloromethane was evaporated under reduced pressure, the residual was purified by column chromatography on silica gel (eluent: ethyl acetate:petroleum ether=1:10; silica gel: 100-140 mesh, Qingdao Marine Chemical Co., Ltd.) to obtain 2-(bromomethyl)-1,1'-biphenyl (0.81 g) with yield of 69%.

To a solution of malononitrile oxime ether sodium salt (0.24 g, 2.02 mmol) dissolved in 15 mL acetonitrile in a 50 mL reaction flask was added 2-(bromomethyl)-1,1'-biphenyl (0.5 g, 2.02 mmol). The reaction was stirred at room temperature, and monitored by Thin-Layer Chromatography (ethyl acetate:petroleum ether=1:8) until the reaction was over, the excessive acetonitrile was evaporated under reduced pressure, the residual was purified by column chromatography on silica gel (eluent: ethyl acetate:petroleum ether=1:10; silica gel: 100-140 mesh, Qingdao Marine Chemical Co., Ltd.) to obtain the title compound 96 (0.31 g) as yellow oil with yield of 59%.

Example 7: The Preparation of Compound 102

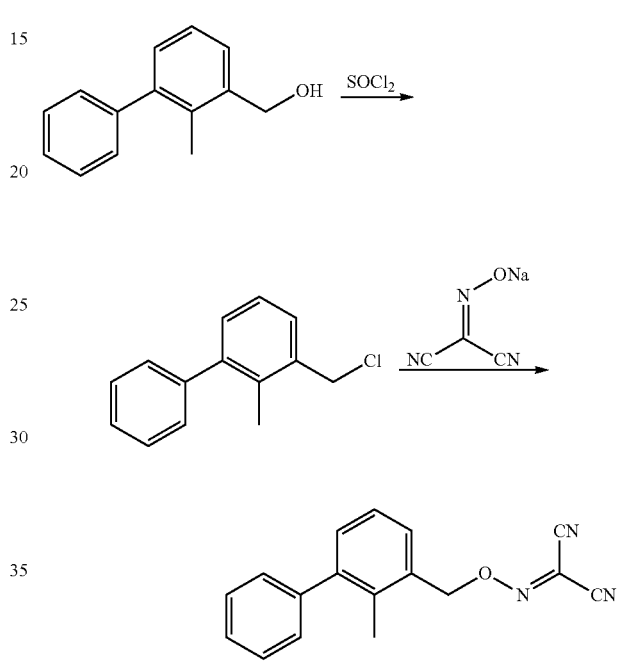

To a solution of (2-methyl-[1,1'-biphenyl]-3-yl)methanol (1 g, 5.04 mmol) dissolved in 25 mL acetonitrile in a 50 mL reaction flask was added slowly thionyl chloride (10 mL). The reaction was stirred overnight, and monitored by Thin-Layer Chromatography until the reaction was over, and the poured into water (100 mL). The water phase was extracted with ethyl acetate (2×50 mL), the organic phase were washed with saturated brine, dried over anhydrous magnesium sulfate, filtered and then concentrated under reduced pressure. the residual was purified by column chromatography on silica gel (eluent: ethyl acetate:petroleum ether=1:10; silica gel: 100-140 mesh, Qingdao Marine Chemical Co., Ltd.) to get pure 3-(chloromethyl)-2-methyl-1,1'-biphenyl (0.95 g) with yield of 87%.

To a solution of malononitrile oxime ether sodium salt (0.27 g, 2.31 mmol) dissolved in 15 mL acetonitrile in a 50 mL reaction flask was added 3-(chloromethyl)-2-methyl-1,1'-biphenyl (0.5 g, 2.31 mmol). The reaction was stirred at room temperature, and monitored by Thin-Layer Chromatography (ethyl acetate:petroleum ether=1:5) until the reaction was over, the excessive acetonitrile was evaporated under reduced pressure, the residual was purified by column chromatography on silica gel (eluent: ethyl acetate:petroleum ether=1:5; silica gel: 100-140 mesh, Qingdao Marine Chemical Co., Ltd.) to obtain the title compound 102 (0.31 g) as yellow solid with yield of 60%.

Example 8: The Preparation of Compound 114

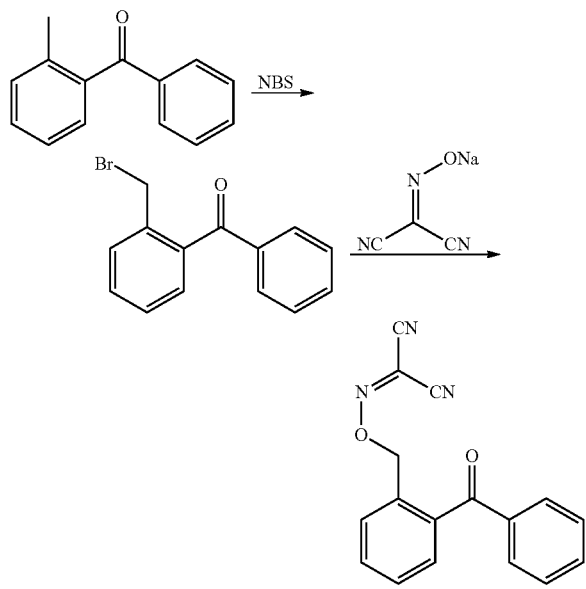

A mixture of phenyl(o-tolyl)methanone (0.8 g, 4.08 mmol), NBS (0.73 g, 4.76 mmol), AIBN (0.01 g) and tetrachloromethane (25 ml) was refluxed and monitored by Thin-Layer Chromatography until the reaction was over. The excessive tetrachloromethane was evaporated under reduced pressure, the residual was purified by column chromatography on silica gel (eluent: ethyl acetate:petroleum ether=1:10; silica gel: 100-140 mesh, Qingdao Marine Chemical Co., Ltd.) to obtain (2-(bromomethyl)phenyl)(phenyl)methanone (0.95 g) with yield of 85%.

To a solution of malononitrile oxime ether sodium salt (0.26 g, 2.18 mmol) dissolved in 15 mL acetonitrile in a 50 mL reaction flask was added (2-(bromomethyl)phenyl)(phenyl)methanone (0.6 g, 2.18 mmol). The reaction was stirred at room temperature, and monitored by Thin-Layer Chromatography (ethyl acetate:petroleum ether=1:3) until the reaction was over, the excessive acetonitrile was evaporated under reduced pressure, the residual was purified by column chromatography on silica gel (eluent: ethyl acetate:petroleum ether=1:5; silica gel: 100-140 mesh, Qingdao Marine Chemical Co., Ltd.) to obtain the title compound 114 (0.42 g) as yellow solid with yield of 67%.

Example 9: The Preparation of Compound 115

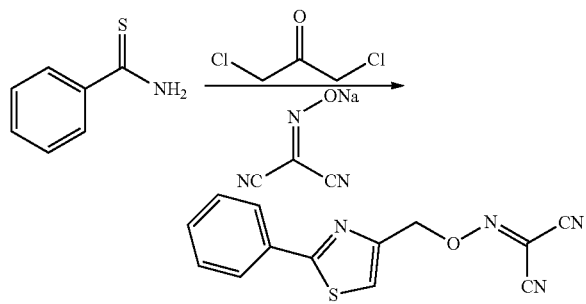

A mixture of benzothioamide (1.5 g, 10.93 mmol), 1,3-dichloropropan-2-one (0.64 g, 10.93 mmol) and ethanol (50 ml) was refluxed in a 100 mL reaction flask and monitored by Thin-Layer Chromatography until the reaction was over. The excessive ethanol was evaporated under reduced pressure, the residual was purified by column chromatography on silica gel (eluent: ethyl acetate:petroleum ether=1:10; silica gel: 100-140 mesh, Qingdao Marine Chemical Co., Ltd.) to obtain 4-(chloromethyl)-2-phenylthiazole (1.9 g) with yield of 83%.

To a solution of malononitrile oxime ether sodium salt (0.28 g, 2.38 mmol) dissolved in 25 mL acetonitrile in a 50 mL reaction flask was added 4-(chloromethyl)-2-phenylthiazole (0.5 g, 2.38 mmol). The reaction was stirred at room temperature, and monitored by Thin-Layer Chromatography (ethyl acetate:petroleum ether=1:5) until the reaction was over, the excessive acetonitrile was evaporated under reduced pressure, the residual was purified by column chromatography on silica gel (eluent: ethyl acetate:petroleum ether=1:5; silica gel: 100-140 mesh, Qingdao Marine Chemical Co., Ltd.) to obtain the title compound 115 (0.35 g) as yellow solid with yield of 55%.

Example 10: The Preparation of Compound 119

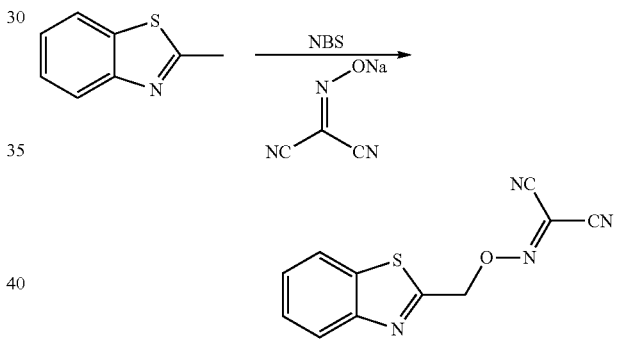

A mixture of 2-methylbenzo[d]thiazole (0.8 g, 5.36 mmol), NBS (0.95 g, 5.36 mmol), AIBN (0.01 g) and tetrachloromethane (25 ml) was refluxed and monitored by Thin-Layer Chromatography until the reaction was over. The excessive tetrachloromethane was evaporated under reduced pressure, the residual was purified by column chromatography on silica gel (eluent: ethyl acetate:petroleum ether=1:10; silica gel: 100-140 mesh, Qingdao Marine Chemical Co., Ltd.) to obtain 2-(bromomethyl)benzo[d]thiazole (0.75 g) with yield of 61%.

To a solution of malononitrile oxime ether sodium salt (0.26 g, 2.19 mmol) dissolved in 15 mL acetonitrile in a 50 mL reaction flask was added 2-(bromomethyl)benzo[d]thiazole (0.5 g, 2.19 mmol). The reaction was stirred at room temperature, and monitored by Thin-Layer Chromatography (ethyl acetate:petroleum ether=1:5) until the reaction was over, the excessive acetonitrile was evaporated under reduced pressure, the residual was purified by column chromatography on silica gel (eluent: ethyl acetate:petroleum ether=1:5; silica gel: 100-140 mesh, Qingdao Marine Chemical Co., Ltd.) to obtain the title compound 119 (0.31 g) as red solid with yield of 58%.

Example 11: The Preparation of Compound 142

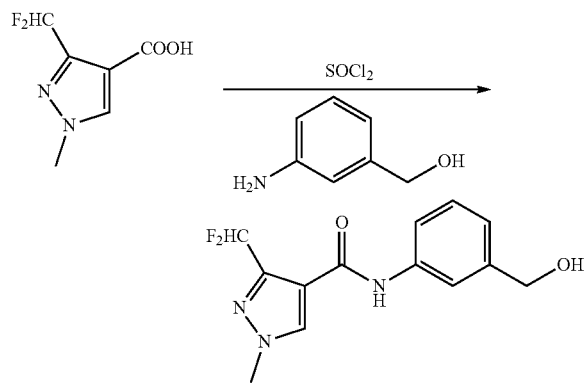

3-(difluoromethyl)-1-methyl-1H-pyrazole-4-carboxylic acid (2 g, 11.36 mmol) was dissolved in 20 mL sulfuryl dichloride, and then heated to reflux for 3 h, the excessive sulfuryl dichloride was evaporated under reduced pressure to get 3-(difluoromethyl)-1-methyl-1H-pyrazole-4-carbonyl chloride, and then the carbonyl chloride was dissolved in 30 mL dichloromethane for the following reaction. To a cooled solution of (3-aminophenyl)methanol (1.4 g, 11.36 mmol) dissolved in 20 mL dichloromethane and 5 mL triethylamine was added slowly the solution of the carbonyl chloride at 0-5° C. After the reaction was stirred for 6 h at room temperature, analysis by Thin-Layer Chromatography showed complete conversion to product, the excessive solvent was evaporated under reduced pressure. the residual was purified by column chromatography on silica gel (eluent: ethyl acetate:petroleum ether=1:3; silica gel: 100-140 mesh, Qingdao Marine Chemical Co., Ltd.) to obtain 3-(difluoromethyl)-N-(3-(hydroxymethyl)phenyl)-1-methyl-1H-pyrazole-4-carboxamide (2.32 g) as white solid with yield of 73%. $^1$H NMR (300 MHz, CDCl$_3$) δ (ppm): 4.11 (s, 3H), 4.73 (s, 2H), 7.16-7.81 (m, 6H).

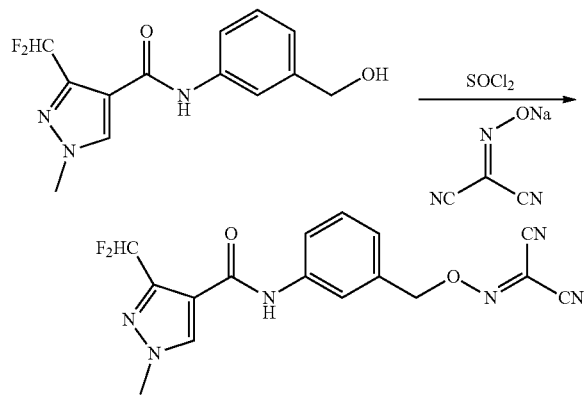

To a solution of 3-(difluoromethyl)-N-(3-(hydroxymethyl)phenyl)-1-methyl-1H-pyrazole-4-carboxamide (1 g, 3.56 mmol) dissolved in 25 mL acetonitrile in a 50 mL reaction flask was added slowly thionyl chloride (10 mL). The reaction was stirred overnight, and monitored by Thin-Layer Chromatography until the reaction was over, and the poured into water (100 mL). The water phase was extracted with ethyl acetate (2×50 mL), the organic phase were washed with saturated brine, dried over anhydrous magnesium sulfate, filtered and then concentrated under reduced pressure. the residual was purified by column chromatography on silica gel (eluent: ethyl acetate:petroleum ether=1:3; silica gel: 100-140 mesh, Qingdao Marine Chemical Co., Ltd.) to get N-(3-(chloromethyl)phenyl)-3-(difluoromethyl)-1-methyl-1H-pyrazole-4-carboxamide (0.83 g) with yield of 78%.

To a solution of malononitrile oxime ether sodium salt (0.20 g, 1.67 mmol) dissolved in 15 mL acetonitrile in a 50 mL reaction flask was added N-(3-(chloromethyl)phenyl)-3-(difluoromethyl)-1-methyl-1H-pyrazole-4-carboxamide (0.5 g, 1.67 mmol). The reaction was stirred at room temperature, and monitored by Thin-Layer Chromatography (ethyl acetate:petroleum ether=1:2) until the reaction was over, the excessive acetonitrile was evaporated under reduced pressure, the residual was purified by column chromatography on silica gel (eluent: ethyl acetate:petroleum ether=1:3; silica gel: 100-140 mesh, Qingdao Marine Chemical Co., Ltd.) to obtain the title compound 142 (0.21 g) as yellow solid with yield of 35%.

Example 12: The Preparation of Compound 167

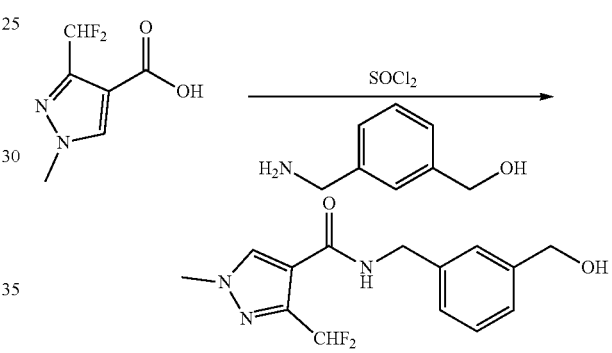

To 3-(difluoromethyl)-1-methyl-1H-pyrazole-4-carboxylic acid (1.5 g, 8.52 mmol) was added dropwise 20 mL sulfuryl dichloride, and then heated to reflux for 3 h, the excessive sulfuryl dichloride was evaporated under reduced pressure to get 3-(difluoromethyl)-1-methyl-1H-pyrazole-4-carbonyl chloride, and then the carbonyl chloride was dissolved in 30 mL dichloromethane for the following reaction. To a cooled solution of (3-(aminomethyl)phenyl)methanol (1.17 g, 8.52 mmol) dissolved in 20 mL dichloromethane and 5 mL triethylamine was added dropwise the solution of the carbonyl chloride at 0-5° C. After the reaction was stirred for 6 h at room temperature, analysis by Thin-Layer Chromatography showed complete conversion to product, the excessive solvent was evaporated under reduced pressure. the residual was purified by column chromatography on silica gel (eluent: ethyl acetate:petroleum ether=1:3; silica gel: 100-140 mesh, Qingdao Marine Chemical Co., Ltd.) to obtain 3-(difluoromethyl)-N-(3-(hydroxymethyl)benzyl)-1-methyl-1H-pyrazole-4-carboxamide (1.8 g) as white solid with yield of 72%.

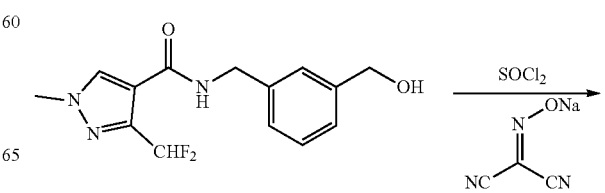

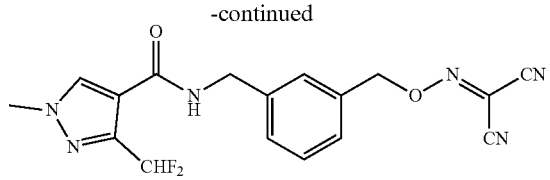

To a solution of 3-(difluoromethyl)-N-(3-(hydroxymethyl)benzyl)-1-methyl-1H-pyrazole-4-carboxamide (0.5 g, 1.69 mmol) dissolved in 25 mL acetonitrile in a 50 mL reaction flask was added slowly thionyl chloride (8 mL). The reaction was stirred overnight, and monitored by Thin-Layer Chromatography until the reaction was over, and the poured into water (100 mL). The water phase was extracted with ethyl acetate (2×50 mL), the organic phase were washed with saturated brine, dried over anhydrous magnesium sulfate, filtered and then concentrated under reduced pressure. the residual was purified by column chromatography on silica gel (eluent: ethyl acetate:petroleum ether=1:3; silica gel: 100-140 mesh, Qingdao Marine Chemical Co., Ltd.) to get N-(3-(chloromethyl)benzyl)-3-(difluoromethyl)-1-methyl-1H-pyrazole-4-carboxamide (0.39 g) with yield of 73%.

To a solution of malononitrile oxime ether sodium salt (0.1 g, 0.85 mmol) dissolved in 15 mL acetonitrile in a 50 mL reaction flask was added N-(3-(chloromethyl)benzyl)-3-(difluoromethyl)-1-methyl-1H-pyrazole-4-carboxamide (0.25 g, 0.8 mmol). The reaction was stirred at room temperature, and monitored by Thin-Layer Chromatography (ethyl acetate:petroleum ether=1:2) until the reaction was over, the excessive acetonitrile was evaporated under reduced pressure, the residual was purified by column chromatography on silica gel (eluent: ethyl acetate:petroleum ether=1:3; silica gel: 100-140 mesh, Qingdao Marine Chemical Co., Ltd.) to obtain the title compound 167 (0.15 g) as yellow oil with yield of 51%.

Example 13: The Preparation of Compound 185

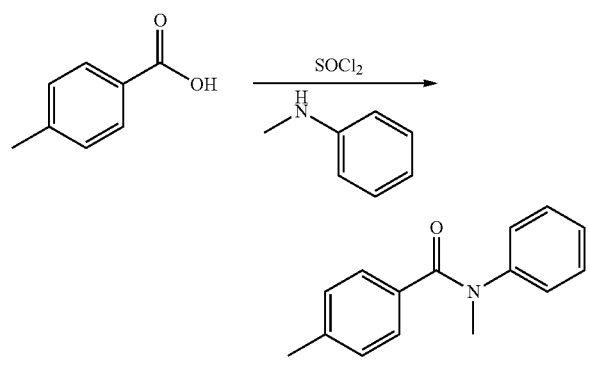

4-methylbenzoic acid (1.5 g, 11.02 mmol) was dissolved in 20 mL sulfuryl dichloride, and then heated to reflux for 3 h, the excessive sulfuryl dichloride was evaporated under reduced pressure to get 4-methylbenzoyl chloride, and then the carbonyl chloride was dissolved in 30 mL dichloromethane for the following reaction. To a cooled solution of N-methylaniline (1.18 g, 11.02 mmol) dissolved in 20 mL dichloromethane and 5 mL triethylamine was added slowly the solution of the carbonyl chloride at 0-5° C. After the reaction was stirred for 4 h at room temperature, analysis by Thin-Layer Chromatography showed complete conversion to product, the excessive solvent was evaporated under reduced pressure. the residual was purified by column chromatography on silica gel (eluent: ethyl acetate:petroleum ether=1:3; silica gel: 100-140 mesh, Qingdao Marine Chemical Co., Ltd.) to obtain N,4-dimethyl-N-phenylbenzamide (1.8 g) as white solid with yield of 73%. $^1$H NMR (300 MHz, CDCl$_3$) δ (ppm): 2.25 (s, 3H), 3.49 (s, 3H), 6.94-7.05 (m, 4H), 7.14-7.26 (m, 5H).

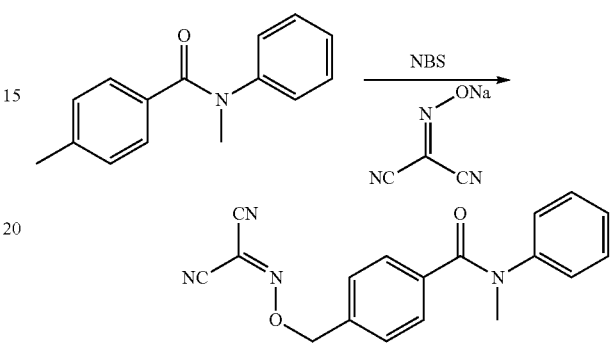

A mixture of N,4-dimethyl-N-phenylbenzamide (0.8 g, 3.55 mmol), NBS (0.64 g, 3.56 mmol), AIBN (0.01 g) and tetrachloromethane (25 ml) was refluxed and monitored by Thin-Layer Chromatography until the reaction was over. The excessive tetrachloromethane was evaporated under reduced pressure, the residual was purified by column chromatography on silica gel (eluent: ethyl acetate:petroleum ether=1:5; silica gel: 100-140 mesh, Qingdao Marine Chemical Co., Ltd.) to obtain 4-(bromomethyl)-N-methyl-N-phenylbenzamide (0.79 g) with yield of 73%.

To a solution of malononitrile oxime ether sodium salt (0.16 g, 1.37 mmol) dissolved in 15 mL acetonitrile in a 50 mL reaction flask was added 4-(bromomethyl)-N-methyl-N-phenylbenzamide (0.4 g, 1.32 mmol). The reaction was stirred at room temperature, and monitored by Thin-Layer Chromatography (ethyl acetate:petroleum ether=1:3) until the reaction was over, the excessive acetonitrile was evaporated under reduced pressure, the residual was purified by column chromatography on silica gel (eluent: ethyl acetate: petroleum ether=1:3; silica gel: 100-140 mesh, Qingdao Marine Chemical Co., Ltd.) to obtain the title compound 185 (0.25 g) as yellow solid with yield of 60%.

Example 14: The Preparation of Compound 202

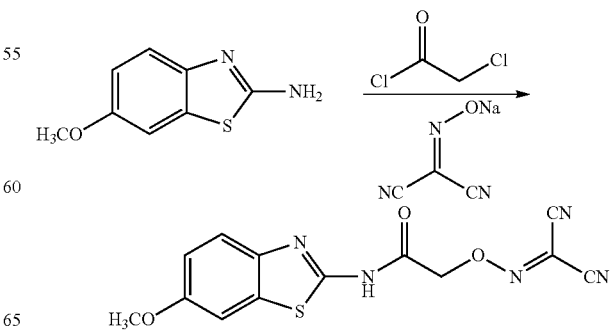

To a cooled solution of 6-methoxybenzo[d]thiazol-2-amine (2.0 g, 11.10 mmol) dissolved in 30 mL dichloromethane and 5 mL triethylamine was added slowly the solution of chloroacetyl chloride (2.0 g, 11.10 mmol) in dichloromethane (10 mL) at 0-5° C. After the reaction was stirred for 4 h at room temperature, analysis by Thin-Layer Chromatography showed complete conversion to product, the excessive solvent was evaporated under reduced pressure. the residual was purified by column chromatography on silica gel (eluent: ethyl acetate:petroleum ether=1:2; silica gel: 100-140 mesh, Qingdao Marine Chemical Co., Ltd.) to obtain 2-chloro-N-(6-methoxybenzo[d]thiazol-2-yl)acetamide (2.42 g) with yield of 85%.

To a solution of malononitrile oxime ether sodium salt (0.92 g, 7.79 mmol) dissolved in 25 mL acetonitrile in a 50 mL reaction flask was added 2-chloro-N-(6-methoxybenzo[d]thiazol-2-yl)acetamide (2.0 g, 7.79 mmol). The reaction was stirred at room temperature, and monitored by Thin-Layer Chromatography (ethyl acetate:petroleum ether=1:1) until the reaction was over, the excessive acetonitrile was evaporated under reduced pressure, the residual was purified by column chromatography on silica gel (eluent: ethyl acetate:petroleum ether=1:1; silica gel: 100-140 mesh, Qingdao Marine Chemical Co., Ltd.) to obtain the title compound 202 (1.14 g) as yellow solid with yield of 46%.

Example 15: The Preparation of Compound 203

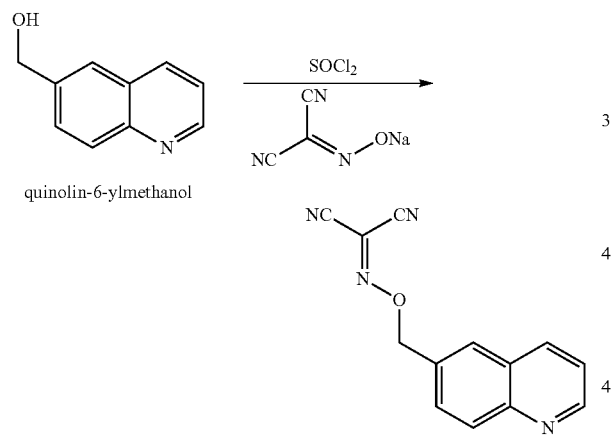

To a solution of quinolin-6-ylmethanol (1 g, 6.28 mmol) dissolved in 25 mL acetonitrile in a 50 mL reaction flask was added slowly thionyl chloride (5 mL). The reaction was stirred overnight, and monitored by Thin-Layer Chromatography until the reaction was over, and the poured into water (100 mL). The water phase was extracted with ethyl acetate (2×50 mL), the organic phase was washed with saturated brine, dried over anhydrous magnesium sulfate, filtered and then concentrated under reduced pressure. the residual was purified by column chromatography on silica gel (eluent: ethyl acetate:petroleum ether=1:10; silica gel: 100-140 mesh, Qingdao Marine Chemical Co., Ltd.) to get 6-(chloromethyl)quinoline (0.75 g) with yield of 67%.

To a solution of malononitrile oxime ether sodium salt (0.33 g, 2.81 mmol) dissolved in 15 mL acetonitrile in a 50 mL reaction flask was added 6-(chloromethyl)quinoline (0.5 g, 2.81 mmol). The reaction was stirred at room temperature, and monitored by Thin-Layer Chromatography (ethyl acetate:petroleum ether=1:3) until the reaction was over, the excessive acetonitrile was evaporated under reduced pressure, the residual was purified by column chromatography on silica gel (eluent: ethyl acetate:petroleum ether=1:3; silica gel: 100-140 mesh, Qingdao Marine Chemical Co., Ltd.) to obtain the title compound 203 (0.35 g) as brown oil with yield of 53%.

Example 16: The Preparation of Compound 210

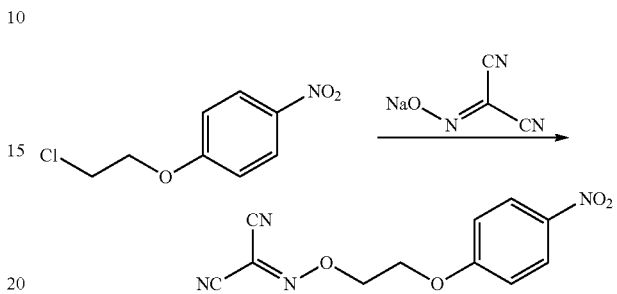

To a solution of malononitrile oxime ether sodium salt (0.29 g, 2.48 mmol) dissolved in 25 mL acetonitrile in a 50 mL reaction flask was added 1-(2-chloroethoxy)-4-nitrobenzene (0.5 g, 2.48 mmol). The reaction was stirred at 80° C., and monitored by Thin-Layer Chromatography (ethyl acetate:petroleum ether=1:5) until the reaction was over, the excessive acetonitrile was evaporated under reduced pressure, the residual was purified by column chromatography on silica gel (eluent: ethyl acetate:petroleum ether=1:5; silica gel: 100-140 mesh, Qingdao Marine Chemical Co., Ltd.) to obtain the title compound 210 (0.26 g) as white solid with yield of 40%.

Example 17: The Preparation of Compound 222

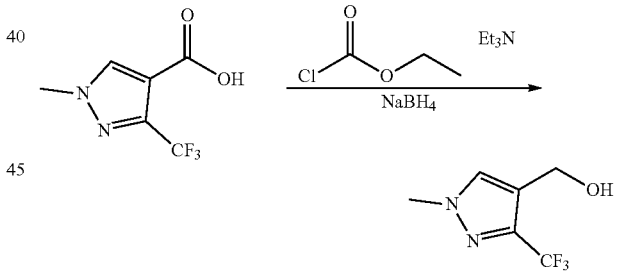

To a cooled solution of 1-methyl-3-(trifluoromethyl)-1H-pyrazole-4-carboxylic acid (1 g, 5.15 mmol) dissolved in 25 mL tetrahydrofuran and triethylamine (0.63 g, 6.18 mmol) in a 50 mL reaction flask, ethyl chloroformate (0.67 g, 6.18 mmol) was added slowly. After the reaction was stirred at room temperature, analysis by Thin-Layer Chromatography showed complete conversion to product. Sodium borohydride (1.95 g, 51.52 mmol) was added and then methanol (10 mL) was added slowly at 00. The mixture was stirred at 0-5° C. for 30 min, the reaction was stirred overnight, and monitored by Thin-Layer Chromatography until the reaction was over, and the poured into water (100 mL). The water phase was extracted with ethyl acetate (2×50 mL), the organic phase was washed with saturated brine, dried over anhydrous magnesium sulfate, filtered and then concentrated under reduced pressure. the residual was purified by column chromatography on silica gel (eluent: ethyl acetate:petroleum ether=1:3; silica gel: 100-140 mesh, Qingdao Marine Chemical Co., Ltd.) to get N-(3-(chloromethyl)phenyl)-3-(difluoromethyl)-1-methyl-1H-pyrazole-4-carboxamide (0.53 g) with yield of 57%.

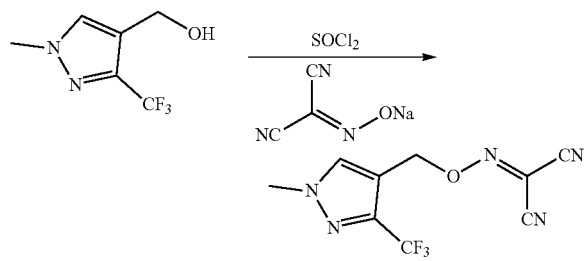

To a solution of N-(3-(chloromethyl)phenyl)-3-(difluoromethyl)-1-methyl-1H-pyrazole-4-carboxamide (0.3 g, 1.67 mmol) dissolved in 25 mL acetonitrile in a 50 mL reaction flask was added slowly thionyl chloride (5 mL). The reaction was stirred overnight, and monitored by Thin-Layer Chromatography until the reaction was over, and the poured into water (100 mL). The water phase was extracted with ethyl acetate (2×50 mL), the organic phase was washed with saturated brine, dried over anhydrous magnesium sulfate, filtered and then concentrated under reduced pressure. the residual was purified by column chromatography on silica gel to get 4-(chloromethyl)-1-methyl-3-(trifluoromethyl)-1H-pyrazole (0.25 g) with yield of 76%.

To a solution of malononitrile oxime ether sodium salt (0.13 g, 1.11 mmol) dissolved in 15 mL acetonitrile in a 50 mL reaction flask was added 4-(chloromethyl)-1-methyl-3-(trifluoromethyl)-1H-pyrazole (0.2 g, 1.11 mmol). The reaction was stirred at room temperature, and monitored by Thin-Layer Chromatography (ethyl acetate:petroleum ether=1:2) until the reaction was over, the excessive acetonitrile was evaporated under reduced pressure, the residual was purified by column chromatography on silica gel (eluent: ethyl acetate:petroleum ether=1:3; silica gel: 100-140 mesh, Qingdao Marine Chemical Co., Ltd.) to obtain the title compound 222 (0.13 g) as yellow oil with yield of 46%.

Example 18: The Preparation of Compound 230

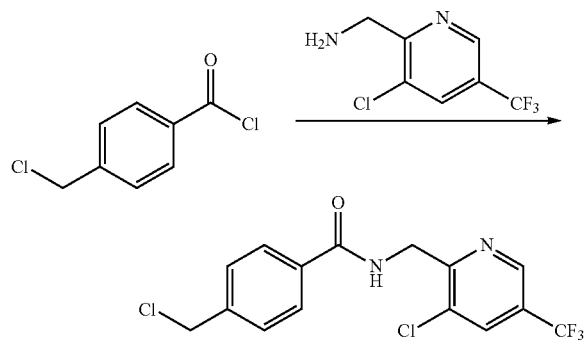

To a cooled solution of (3-chloro-5-(trifluoromethyl)pyridin-2-yl)methanamine (0.45 g, 2.12 mmol) dissolved in 30 mL dichloromethane and 5 mL triethylamine in a 100 mL reaction flask was added slowly the solution of 4-(chloromethyl)benzoyl chloride (0.4 g, 2.12 mmol) in dichloromethane (10 mL). After the reaction was stirred at room temperature, analysis by Thin-Layer Chromatography showed complete conversion to product, the reaction mixture was concentrated under reduced pressure. the residual was purified by column chromatography on silica gel (eluent: ethyl acetate:petroleum ether=1:2; silica gel: 100-140 mesh, Qingdao Marine Chemical Co., Ltd.) to get N-((3-chloro-5-(trifluoromethyl)pyridin-2-yl)methyl)-4-(chloromethyl)benzamide (0.52 g) with yield of 68%.

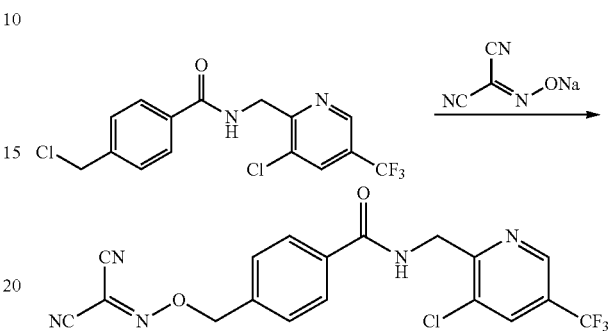

To a solution of malononitrile oxime ether sodium salt (0.1 g, 0.85 mmol) dissolved in 25 mL acetonitrile in a 50 mL reaction flask was added N-((3-chloro-5-(trifluoromethyl)pyridin-2-yl)methyl)-4-(chloromethyl)benzamide (0.3 g, 0.83 mmol). The reaction was stirred at room temperature, and monitored by Thin-Layer Chromatography (ethyl acetate:petroleum ether=1:5) until the reaction was over, the excessive acetonitrile was evaporated under reduced pressure, the residual was purified by column chromatography on silica gel (eluent: ethyl acetate:petroleum ether=1:5; silica gel: 100-140 mesh, Qingdao Marine Chemical Co., Ltd.) to obtain the title compound 230 (0.19 g) as yellow solid with yield of 55%.

Biological Testing

Example 19: Rice Blast and Gray Mold Testing

Determination method of fungicidal activity in vitro: High Through Put is used in the test, the compound is dissolved in a proper solvent (the solvent is selected from acetone, methanol, DMF and so on according to their dissolving capability to the sample.) to become a testing solution whose concentration is designed. In a no animalcule condition, the testing solution and pathogens suspension are added into the cells of 96 cells culture board, which then should be placed in the constant temperature box. 24 hours later, pathogengermination or growth can be investigated by eyeballing, and the activity in vitro of the compound si evaluated based on germination or growth of control treatment.

The activities in vitro (inhibition rate) of some compounds are as follows:

At the dosage of 25 mg/L, the inhibition rate of compounds 5, 7, 23, 57, 59, 65, 69, 85, 91, 93, 99, 102, 106, 107, 109, 112, 113, 114, 119, 122, 142, 168, 189, 194, 201, 203, 205, 207, 208, 209, 210, 213, 214, 215, 216, 218, 220, 221, 222, 224, 225, 228, 229, 230, 231, 232, 233 was 100% against rice blast At the dosage of 25 mg/L, the inhibition rate of compounds 4, 7, 22, 36, 53, 59, 60, 69, 86, 96, 99, 102, 105, 107, 109, 112, 113, 115, 116, 118, 120, 150, 159, 167, 185, 187, 202, 203, 204, 205, 206, 208, 209, 210, 214, 215, 216, 218, 220, 221, 228, 230, 231, 232 was 100% against gray mold.

Example 20: The Determination Method of Protective Activity In Vivo

The method is as followed: The compound is dissolved in a proper solvent to get mother solution. The solvent is selected from acetone, methanol, DMF and so on according to their dissolving capability to the sample. The volume rate of solvent and testing solution (v/v) is equal to or less than 5%. The mother solution is diluted with water containing 0.1% tween-80 to get the testing solution whose concentration is designed. Plants are sprayed on leaves with the preparation of active compound according to the invention and spray application is repeated 3 times. Plants, used as controls, are treated with an aqueous solution not containing the active material. The plants are inoculated one day after treating the plants with the compounds of this invention. The plants are stored in a humidity chamber (25° C. (day), 20° C. (night), 95-99% humidity) and then transferred into greenhouse after 24 hours. The activity of compound is obtained by eyeballing after 7 days according to the *A Manual of Assessment Keys for Plant Diseases* published by American Phytopathological Society. 0% means an efficacy which corresponds to that of the control, while an efficacy of 100% means that no disease is observed.

At the dosage of 400 ppm, the compounds 86, 91, 94, 103, 109, 110, 114, 115, 142, 187, 188, 189, 233 showed more than 80% control against corn rust Example 21: The Determination of Controlling Plant Bacterial Disease The compounds of the present invention have been tested for the control of various plant bacterial diseases. The test procedure is as follows:

Melon bacterial fruit blotch: The testing compound is dissolved in a small amount of DMF and diluted with water to the desired concentration. The pathogenic bacteria in the stable growth phase is mixed with the testing solution. After melon seeds (accelerating germination) soaked in the solution containing pathogenic bacteria and compound for 0.5 hour, the seeds are sown in earthworm soil cup and then transferred into a greenhouse to allow disease to develop. After 2 weeks, The activity of the compound is evaluated based on germination or growth of control treatment Soft rot of chinese cabbage: Chinese cabbage leaves are cut into 2 cm square and placed on the double filter paper in a petri dish. The testing compound is dissolved in DMF and diluted with water to the desired concentration. The testing solution is sprayed onto the surface of the cabbage leaf and dried in a fume hood. The surface of cabbage leaf is pierced using inoculation needle. A spore suspension (5 μl) of the chinese cabbage soft rot bacteria in the stable growth phase is inoculated onto the breakage of leaves, disease development is allowed to progress in a growth cabinet under dark condition for 48 hours. The activity of the compound is evaluated based on germination or growth of control treatment.

Bacterial leaf spot of cucumber, bacterial leaf spot of tomato, bacterial leaf streak of rice, bacterial blight of rice: The testing compound is dissolved in DMF and diluted with water to the desired concentration. The testing solution is sprayed to the host plant by a special plant sprayer. After air drying in cool place, the plant is inoculated with pathogen in the stable growth phase, and then transferred into a greenhouse and incubated for 10 days under a humid atmosphere in common. Grading is carried out, in comparison with the control plants.

The test results are as follows:

At the dosage of 800 mg/L, the compounds 9, 59, 83 and 115 showed 100% control against melon bacterial fruit blotch.

At the dosage of 600 mg/L, the compounds 9, 19, 34, 37, 59, 83 and 115 showed 100% control against bacterial leaf spot of cucumber, bacterial leaf streak of rice and bacterial blight of rice.

At the dosage of 400 mg/L, the compounds 9, 19, 34, 36, 37, 59, 83 and 115 showed 100% control against soft rot of chinese cabbage and bacterial leaf spot of tomato.

Example 22: Field Trial

Compounds 59 and 115 were selected from the above compounds for field trial to control bacterial leaf streak of rice (*Xanthomonas oryzae* pv. *oryzicola*) at dosage of 400 g a.i./hm². The check (thiazole zinc and kocide 3000, commercially available) was set at one dose (400 g a.i./hm²). The plot size was 15 m² and treatments were assigned to plots randomly. Spray applications on leaves and stems were made on 7-day intervals and each application was repeated 3 times. A week after 3 spray applications, five random points of each plot were investigated to calculate the effectiveness of the testing compounds in controlling disease according to pesticide guidelines for the field efficacy trials

TABLE 3

Field trial results for test compounds against bacterial leaf streak of rice

| compound | Concentrations (g a.i./hm²) | repeat I | repeat II | repeatIII | average |
|---|---|---|---|---|---|
| 115 | 400 | 61.08 | 53.23 | 66.00 | 60.10 |
| 59 | 400 | 56.96 | 58.37 | 51.24 | 55.52 |
| kocide 3000 | 400 | 34.91 | 33.29 | 39.72 | 35.97 |
| thiazole zinc | 400 | 39.21 | 37.24 | 37.88 | 38.11 |

We claim:
1. A malononitrile oxime ether compound relates to compounds of formula I

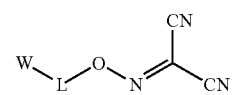

wherein
L is selected from the group consisting of:
—(CR$^1$R$^2$)$_n$—,
—(CR$^1$R$^2$)$_m$—CH$_2$—(C═O)—CH$_2$—(CR$^1$R$^2$)$_p$—,
—(CR$^1$R$^2$)$_m$—(CR$^1$═CR$^2$)—(CR$^1$R$^2$)$_p$,
—(CR$^1$R$^2$)$_m$—(C═O)—O—CH$_2$—(CR$^1$R$^2$)$_p$—,
—(CR$^1$R$^2$)$_m$—(C≡C)—(CR$^1$R$^2$)$_p$—,
—(CR$^1$R$^2$)$_m$—O—(C═O)—CH$_2$—(CR$^1$R$^2$)$_p$—,
—(CR$^1$R$^2$)$_m$—O—CH$_2$—(CR$^1$R$^2$)$_p$—,
—(CR$^1$R$^2$)$_m$—(C═O)—NH—CH$_2$—(CR$^1$R$^2$)$_p$—,
—(CR$^1$R$^2$)$_m$—NH—CH$_2$—(CR$^1$R$^2$)$_p$—,
—(CR$^1$R$^2$)$_m$—NH—(C═O)—CH$_2$—(CR$^1$R$^2$)$_p$— and
—(CR$^1$R$^2$)$_m$—S—CH$_2$—(CR$^1$R$^2$)$_p$—, where
n represents 1, 2, 3 or 4;

m and p independently represent 0, 1, 2 or 3;

$R^1$ and $R^2$ are independently selected from the group consisting of hydrogen, halogen, cyano, [$C_1$-$C_4$]-alkyl, [$C_1$-$C_4$]-haloalkyl, [$C_3$-$C_5$]-cycloalkyl, [$C_2$-$C_4$]-alkenyl, [$C_2$-$C_4$]-haloalkenyl, [$C_2$-$C_4$]-alkynyl, [$C_2$-$C_4$]-haloalkynyl, [$C_1$-$C_4$]-alkoxy, [$C_1$-$C_4$]-haloalkoxy, [$C_1$-$C_4$]-alkoxy-[$C_1$-$C_4$]-alkyl, [$C_1$-$C_4$]-alkoxy-[$C_1$-$C_4$]-alkoxy, and $C_1$-$C_4$ haloalkoxy $C_1$-$C_4$ alkyl;

W is selected from non-substituted or substituted aryl or non-substituted or substituted aromatic heterocycle; and, when L is —$(CR^1R^2)_n$—, $R^1$ and $R^2$ are each hydrogen and n is 1, W is not benzene.

2. The compound according to claim 1, wherein,

L is selected from the group consisting of: —$(CR^1R^2)_n$—, —$(CR^1R^2)_m$—$CH_2$—(C=O)—$CH_2$—$(CR^1R^2)_p$—, —$(CR^1R^2)_m$—($CR^1$=$R^2$)—$(CR^1R^2)_p$—, —$(CR^1R^2)_m$—(C=O)—O—$CH_2$—$(CR^1R^2)_p$—, —$(CR^1R^2)_m$—(C≡C)—$(CR^1R^2)_p$—, —$(CR^1R^2)_m$—O(C=O)—$CH_2$—$(CR^1R^2)_p$—, —$(CR^1R^2)_m$—O—$CH_2$—$(CR^1R^2)_p$—, —$(CR^1R^2)_m$—(C=O)—NH—$CH_2$—$(CR^1R^2)_p$—, —$(CR^1R^2)_m$—NH—$CH_2$—$(CR^1R^2)_p$—, —$(CR^1R^2)_m$—NH—(C=O)—$CH_2$—$(CR^1R^2)_p$— and —$(CR^1R^2)_m$—S—$CH_2$—$(CR^1R^2)_p$—;

n represents 1, 2, 3 or 4;

m and p are each independently represent 0, 1, 2 or 3;

$R^1$ and $R^2$ are each hydrogen; W is selected from one of the groups represented by $W^1$-$W^{84}$:

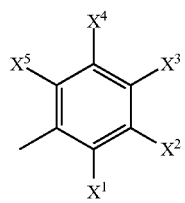

W¹

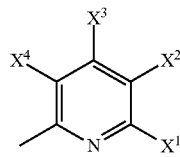

W²

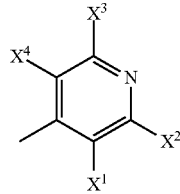

W³

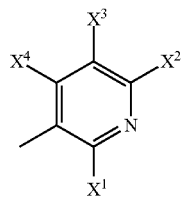

W⁴

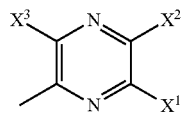

W⁵

-continued

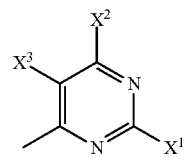

W⁶

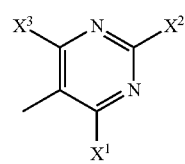

W⁷

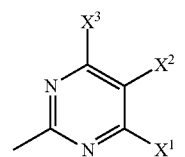

W⁸

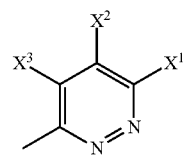

W⁹

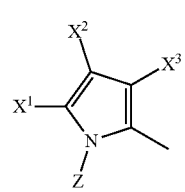

W¹⁰

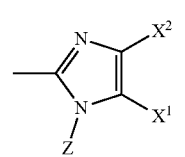

W¹¹

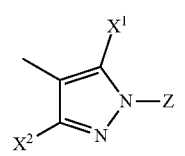

W¹²

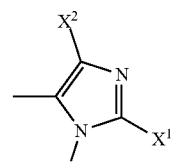

W¹³

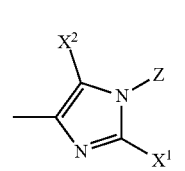

W¹⁴

-continued
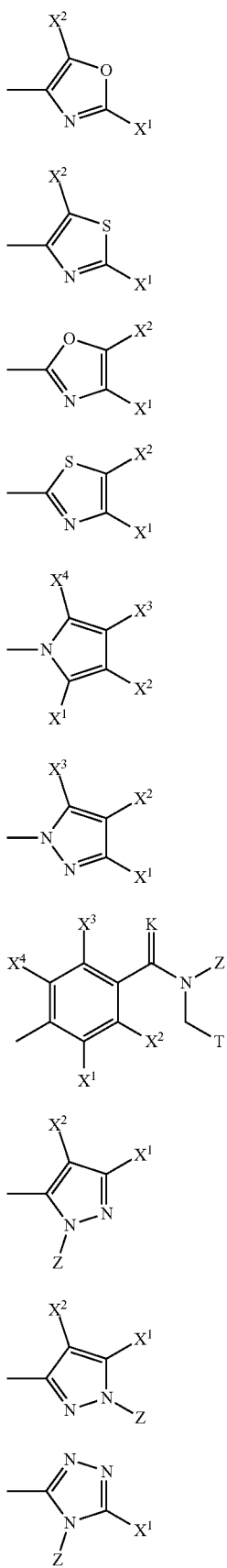
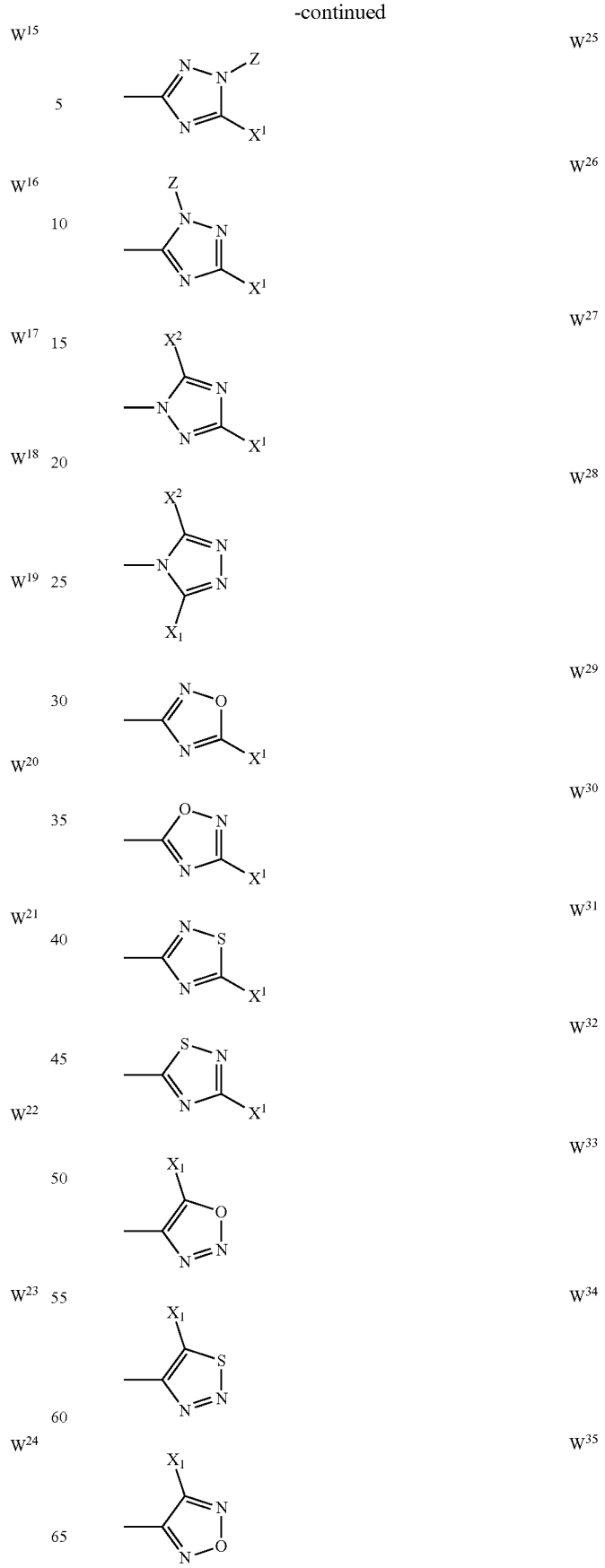

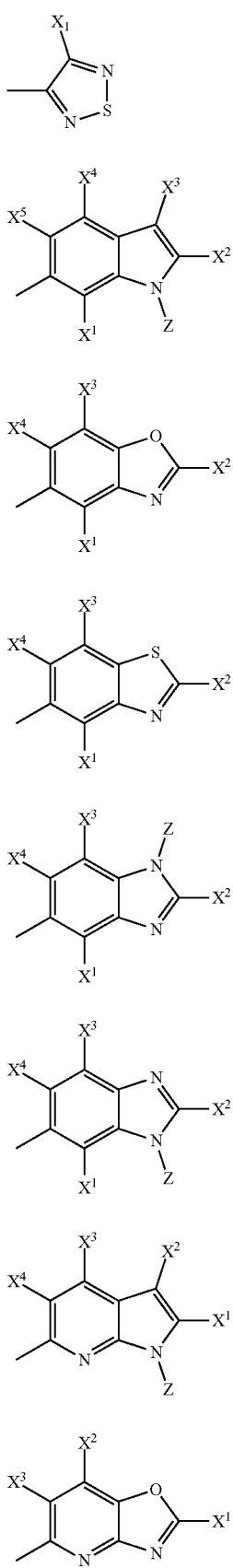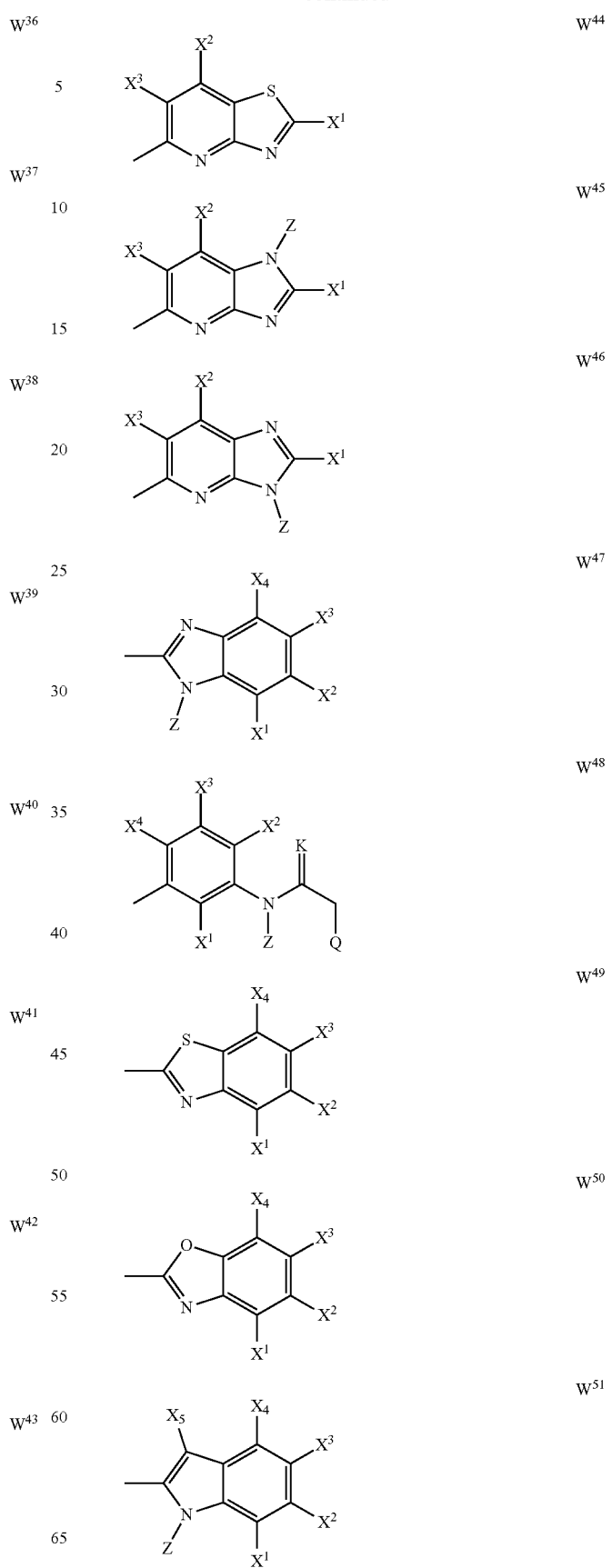

-continued
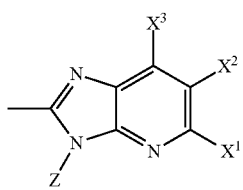
W52
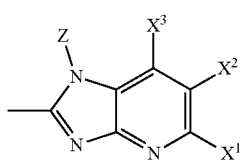
W53
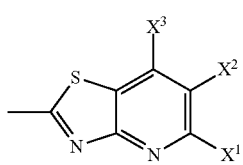
W54
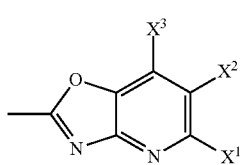
W55
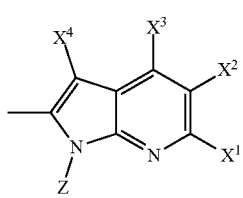
W56
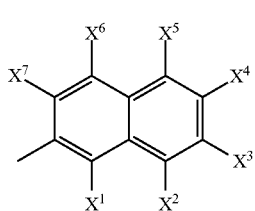
W57
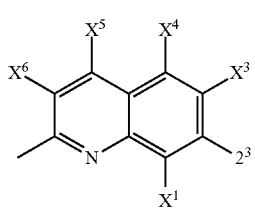
W58
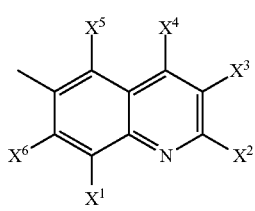
W59
-continued
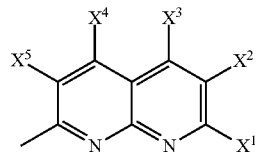
W60
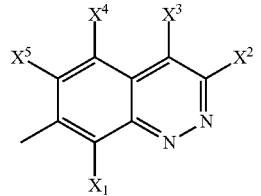
W61
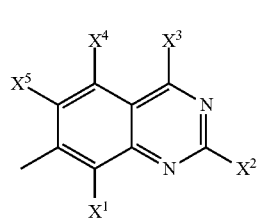
W62
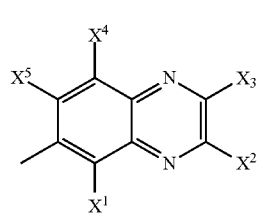
W63
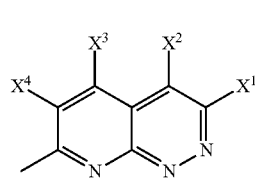
W64
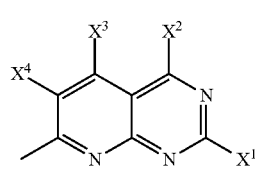
W65
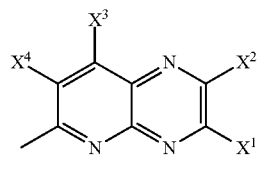
W66
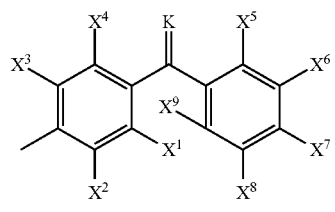
W67

-continued

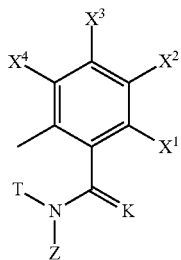
W⁸⁰

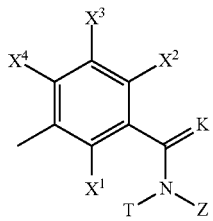
W⁸¹

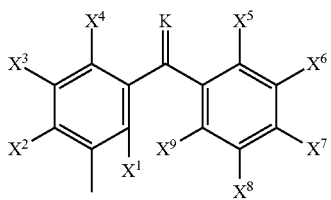
W⁸²

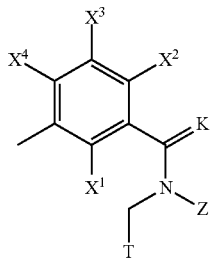
W⁸³

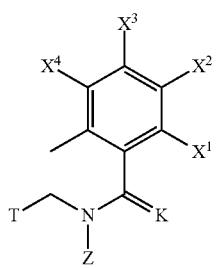
W⁸⁴ wherein: $X^1$, $X^2$, $X^3$, $X^4$, $X^5$, $X^6$, $X^7$, $X^8$ and $X^9$ are each independently selected from the group consisting of hydrogen, halogen, cyano, nitro, $-SF_5$, $[C_1-C_8]$-alkyl, $[C_1-C_8]$-haloalkyl, $[C_3-C_6]$-cycloalkyl, $[C_2-C_8]$-alkenyl, $[C_2-C_8]$-haloalkenyl, $[C_2-C_8]$-alkynyl, $[C_2-C_8]$-haloalkynyl, $[C_1-C_8]$-alkoxy-$[C_1-C_8]$-alkyl, $-OR^3$, $-C(=O)OR^3$, $-N(R^4)S(=O)_2R^5$, $-S(=O)_2NR^3R^5$, $-N(R^4)C(=O)OR^3$, $-CR^4=NOR^3$, $-CH_2ON=C(CN)_2$, $-C(=O)SR^3$, $-C(=S)OR^3$, $-C(=S)SR^3$, $-CR^4=NR^5$, $-CR^4=N-NR^3R^5$, $-OSiR^4R^5R^6$, $-OC(=O)R^4$, $-OC(=O)OR^3$, $-OC(=O)NR^3R^4$, $-OC(=S)NR^3R^4$, $-NR^3R^4$, $-N(R^4)C(=O)NR^3R^5$, $-N(R^4)C(=S)NR^3R^5$, $-N=CR^4R^5$, $-N=C-NR^3R^4$, $-N(R^4)C(=NR^5)NR^3R^6$, $-N(R^4)OR^3$, $-N(R^4)NR^3R^5$, $-N=NR^4$, $-N(R^4)S(=O)R^5$, $-N(R^4)S(=O)_2OR^3$, $-N(R^4)S(=O)OR^3$, $-N(R^4)S(=O)NR^3R^5$, $-N(R^4)S(=O)_2NR^3R^5$, $NR^4C(=O)R^5$, $-SR^3$, $-S(=O)_2R^4$, $-S(=O)R^4$, $-S(=O)OR^3$, $-S(=O)NR^3R^4$, $-S(=O)_2OR^3$, $-S(=O)NR^3R^4$, $-SiR^3R^4R^5$, non-substituted or substituted phenyl, non-substituted or substituted pyridyl, non-substituted or substituted pyrazolyl, non-substituted or substituted thiazolyl, non-substituted or substituted isothiazolyl, and non-substituted or substituted thiadiazolyl, wherein the substituent is selected from the group consisting of halogen, cyano, nitro, $[C_1-C_8]$-alkyl, $[C_1-C_8]$-haloalkyl, $[C_1-C_8]$-alkoxy, $[C_1-C_8]$-haloalkoxy, $[C_1-C_8]$-alkylthio and $[C_1-C_8]$-haloalkylthio;

Z is selected from the group consisting of hydrogen, $[C_1-C_8]$-alkyl, $[C_1-C_8]$-haloalkyl, $[C_3-C_6]$-cycloalkyl, $[C_2-C_8]$-alkenyl, $[C_2-C_8]$-haloalkenyl, $[C_2-C_8]$-alkynyl, $[C_2-C_8]$-haloalkynyl, aryl, aryl-$[C_1-C_8]$alkyl, $[C_1-C_8]$-alkoxy-$[C_1-C_8]$-alkyl, $-C(=O)R^3$ and $-C(=O)OR^3$;

K is selected from the group consisting of oxygen, sulfur, $NR^3$, $N-OR^4$ and $N-NR^3R^4$; $R^3$ is selected from the group consisting of hydrogen, $[C_1-C_8]$alkyl, $[C_1-C_8]$-haloalkyl, $[C_3-C_6]$-cycloalkyl, $[C_1-C_8]$-alkyloxycarbonyl, $[C_2-C_8]$-alkenyl, $[C_2-C_8]$-haloalkenyl, $[C_2-C_8]$-alkynyl, $[C_2-C_8]$-haloalkynyl, unsubstituted or substituted phenyl, non-substituted or substituted pyridyl non-substituted or substituted pyrazolyl, non-substituted or substituted thiazolyl, non-substituted or substituted isothiazolyl and non-substituted or substituted thiadiazolyl, wherein the substituent is selected from the group consisting of halogen, cyano, nitro, hydroxyl, mercapto, amino, $CONH_2$, COOH, CHO, $[C_1-C_4]$-alkyl, $[C_1-C_4]$-haloalkyl, $[C_3-C_6]$-cycloalkyl, $[C_1-C_3]$-alkoxy, $[C_1-C_3]$-haloalkoxy, $[C_1-C_3]$-alkylthio, $[C_1-C_3]$-haloalkylthio, $[C_1-C_3]$-alkylamino, $[C_1-C_3]$-dialkylamino, $[C_3-C_6]$-cycloalkylamino, $[C_1-C_3]$-alkoxycarbonyl, $[C_1-C_3]$-alkylsulfonyl, $[C_1-C_3]$-alkylaminocarbonyl and $[C_1-C_3]$-alkylaminosulfonyl;

$R^4$, $R^5$ and $R^6$ are each independently selected from hydrogen, $[C_1-C_8]$-alkane, $[C_1-C_8]$-haloalkyl, $[C_3-C_6]$-cycloalkyl, $[C_1-C_8]$-alkoxy, $[C_1-C_8]$-haloalkoxy, $[C_1-C_8]$-alkoxycarbonyl, $[C_2-C_8]$-alkenyl, $[C_2-C_8]$-haloalkenyl, $[C_2-C_8]$-alkynyl, $[C_2-C_8]$-haloalkynyl, non-substituted or substituted phenyl, non-substituted or substituted pyridyl, non-substituted or substituted pyrazolyl, non-substituted or substituted thiazolyl, non-substituted or substituted isothiazolyl and non-substituted or substituted thiadiazolyl, wherein the substituent group is selected from the group consisting of halogen, cyano, nitro, hydroxyl mercapto, amino, $CONH_2$, COOH, CHO, $[C_1-C_4]$-alkyl, $[C_1-C_4]$-haloalkyl, $[C_3-C_6]$-cycloalkyl, $[C_1-C_3]$-alkoxy, $[C_1-C_3]$-haloalkoxy, $[C_1-C_3]$-alkylthio, $[C_1-C_3]$-haloalkylthio, $[C_1-C_3]$-alkylamino, $[C_1-C_3]$-dialkylamino, $[C_3-C_6]$-cycloalkylamino, $[C_1-C_3]$-alkoxycarbonyl, $[C_1-C_3]$-alkylsulfonyl, $[C_1-C_3]$-alkylaminocarbonyl and $[C_1-C_3]$-alkylaminosulfonyl;

Q is selected from the group consisting of $Q^{1-10}$, non-substituted or substituted phenyl, non-substituted or substituted pyridyl, non-substituted or substituted pyrazolyl, non-substituted or substituted thiazolyl, non-substituted or substituted isothiazolyl and non-substituted or substituted thiadiazolyl, wherein the substituent group is selected from the group consisting of halogen, cyano, nitro, hydroxyl, mercapto, amino, $CONH_2$, COOH, CHO, $[C_1-C_4]$-alkyl, $[C_1-C_4]$-haloalkyl, $[C_3-C_6]$-cycloalkyl, $[C_1-C_3]$-alkoxy, $[C_1-C_3]$- haloalkoxy, [C₁-C₃]-alkylthio, [C₁-C₃]haloalkylthio, [C₁-C₃]-alkylamino, [C₁-C₃]-dialkylamino, [C₃-C₆]-cycloalkylamino, [C₁-C₃]-alkoxycarbonyl, [C₁-C₃]-alkylsulfonyl, [C₁-C₃]-alkylaminocarbonyl and [C₁-C₃]-alkylaminosulfonyl, and where $Q^{1-10}$ are:

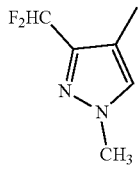
Q¹

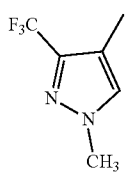
Q²

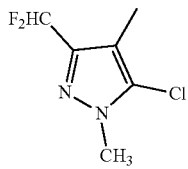
Q³

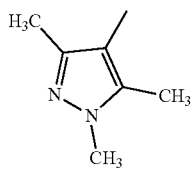
Q⁴

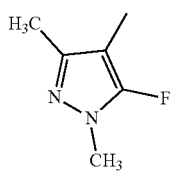
Q⁵

Q⁶

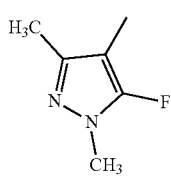
Q⁷

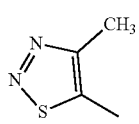
Q⁸

Q⁹

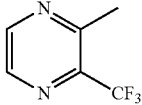
Q¹⁰ and

T is selected from the group consisting of cyano, [C₁-C₈]-alkyl, [C₁-C₈]-haloalkyl, [C₃-C₆]-cycloalkyl, [C₂-C₈]-alkenyl, [C₂-C₈]-haloalkenyl, [C₂-C₈]-alkynyl, [C₂-C₈]-haloalkynyl, non-substituted or substituted phenyl, non-substituted or substituted pyridyl, non-substituted or substituted pyrazolyl, non-substituted or substituted thiazolyl, non-substituted or substituted isothiazolyl and non-substituted or substituted thiadiazolyl, wherein the substituent is selected from the group consisting of halogen, cyano, nitro, hydroxyl, mercapto, amino, CONH₂, COOH, CHO, [C₁-C₄]-alkyl, [C₁-C₄]-haloalkyl, [C₃-C₆]-cycloalkyl, [C₁-C₃]-alkoxy, [C₁-C₃]-haloalkoxy, [C₁-C₃]-alkylthio, [C₁-C₃]-haloalkylthio, [C₁-C₃]-alkylamino, [C₁-C₃]-dialkylamino, [C₃-C₆]-cycloalkylamino, [C₁-C₃]-alkoxycarbonyl, [C₁-C₃]-alkylsulfonyl, [C₁-C₃]-alkylaminocarbonyl and [C₁-C₃]alkylaminosulfonyl.

3. The compound according to claim 2, wherein
L is selected from the group consisting of —(CR¹R²)ₙ—, —(CR¹R²)ₘ—NH—(C=O)—CH₂—(CR¹R²)—, —(CR¹R²)ₘ—O—CH₂—(CR¹R²)ₚ— and —(CR¹R²)ₘ—S—CH₂—(CR¹R²)ₚ—;
where
n represents 1, 2, 3 or 4;
m and p independently represent 0, 1, 2 or 3;
R¹ and R² are selected from hydrogen;
W is selected from the group consisting of W¹, W², W³, W⁴, W¹², W¹⁶, W¹⁸, W²¹, W²³, W⁴⁸, W⁴⁹, W⁶⁷, W⁶⁸, W⁶⁹, W⁷⁰, W⁷¹, W⁷², W⁷³, W⁷⁴, W⁷⁵, W⁷⁶, W⁷⁷, W⁷⁸, W⁷⁹, W⁸⁰, W⁸¹, W⁸², W⁸³ and W⁸⁴;
X¹, X², X³, X⁴, X⁵, X⁶, X⁷, X⁸ and X⁹ are each independently selected from the group consisting of hydrogen, halogen, cyano, nitro, [C₁-C₃]-alkyl, [C₁-C₃]-haloalkyl, [C₁-C₃]-alkoxy—[C₁-C₃]-alkyl, —OR³, —C(=O)OR³, —N(R⁴)S(=O)₂R⁵, —S(=O)₂NR³R⁵, —N(R⁴)C(=O)OR³, —CR⁴=NOR³, —CH₂ON=C(CN)₂, NR⁴C(=O)R⁵, non-substituted or substituted phenyl and non-substituted or substituted pyridyl, wherein the substituent is selected from the group consisting of halogen, cyano, nitro, [C₁-C₃]-alkyl, [C₁-C₃]-haloalkyl, [C₁-C₃]-alkoxy, [C₁-C₃]-haloalkoxy, [C₁-C₃]-alkylthio and [C₁-C₃]-haloalkylthio;
Z is selected from the group consisting of hydrogen, [C₁-C₃]-alkyl, [C₁-C₃]-haloalkyl, phenylmethyl, —C(=O)R³ and —C(=O)OR³;
K is selected from oxygen or sulfur;
R³ is selected the group consisting of hydrogen, [C₁-C₃]-alkyl, [C₁-C₃]-haloalkyl, [C₁-C₃]-alkoxycarbonyl, non-substituted or substituted phenyl and non-substituted or substituted pyridyl, wherein the substituent is selected from the group consisting of halogen, cyano, nitro, [C₁-C₃]-alkyl, [C₁-C₃]-haloalkyl, [C₁-C₃]-alkoxy, [C₁-C₃]-haloalkoxy, [C₁-C₃]-alkylthio and [C₁-C₃]-haloalkylthio;

$R^4$ and $R^5$ are each independently selected from the group consisting of hydrogen, [C₁-C₃]-alkyl, [C₁-C₃]-haloalkyl, [C₁-C₃]-alkoxy, [C₁-C₃]-haloalkoxy, [C₁-C₃]-alkoxycarbonyl, non-substituted or substituted phenyl and non-substituted or substituted pyridyl group, wherein the substituent is selected from the group consisting of halogen cyano, nitro, [C₁-C₃]-alkyl, [C₁-C₃]-haloalkyl, [C₁-C₃]-alkoxy, [C₁-C₃]-haloalkoxy, [C₁-C₃]-alkylthio and [C₁-C₃]-haloalkylthio;

Q is selected from the group consisting of $Q^{1-10}$, non-substituted or substituted phenyl and non-substituted or substituted pyridyl, where the substituent group is selected from the group consisting of halogen, cyano, nitro, hydroxyl, mercapto, amino, CONH₂, COOH, CHO, [C₁-C₃]alkyl, [C₁-C₃]-haloalkyl, [C₃-C₆]-cycloalkyl, [C₁-C₃]alkoxy, [C₁-C₃]haloalkoxy, [C₁-C₃]-alkylthio, [C₁-C₃]-haloalkyl, [C₁-C₃]-alkylamino, [C₁-C₃]-dialkylamino, [C₃-C₆]-cycloalkylamino, [C₁-C₃]-alkoxycarbonyl, [C₁-C₃]-alkylsulfonyl, [C₁-C₃]alkylaminocarbonyl and [C₁-C₃]-alkylaminosulfonyl and where $Q^{1-10}$ are:

and

T is selected from cyano, [C₁-C₃]-alkyl, [C₁-C₃]-haloalkyl, [C₃-C₆]-cycloalkyl, non-substituted or substituted phenyl and non-substituted or substituted pyridyl, wherein the substituent group is selected from the group consisting of halogen, cyano, nitro, [C₁-C₃]-alkyl, [C₁-C₃]-haloalkyl, [C₃-C₆]-cycloalkyl, [C₁-C₃]-alkoxy, [C₁-C₃]-haloalkoxy, [C₁-C₃]-alkylthio, [C₁-C₃]-halo-alkylthio, [C₁-C₃]-alkylamino, [C₁-C₃]-dialkylamino, [C₃-C₆]-cycloalkylamino, [C₁-C₃]-alkoxycarbonyl, [C₁-C₃]-alkylsulfonyl, [C₁-C₃]-alkylaminocarbonyl and [C₁-C₃]-alkylaminosulfonyl.

4. The compound according to claim 2, wherein
L is selected from the group consisting of: —(CR¹R²)ₙ—, —(CR¹R²)ₘ—NH—(C=O)—CH₂—(CR¹R²)ₚ—, —(CR¹R²)ₘ—O—CH₂—(CR¹R²)ₚ— and —(CR¹R²)ₘ—S—CH₂—(CR¹R²)ₚ—;
n represents 1 or 2;
m and p independently represent 0, 1 or 2;
$R^1$ and $R^2$ are selected from hydrogen;
W is selected from the group consisting of $W^1$, $W^2$, $W^3$, $W^4$, $W^{12}$, $W^{16}$, $W^{18}$, $W^{21}$, $W^{23}$, $W^{48}$, $W^{49}$, $W^{67}$, $W^{68}$, $W^{69}$, $W^{70}$, $W^{71}$, $W^{72}$, $W^{73}$, $W^{74}$, $W^{75}$, $W^{76}$, $W^{77}$, $W^{78}$, $W^{79}$, $W^{80}$, $W^{81}$, $W^{82}$, $W^{83}$ and $W^{84}$;
$X^1$, $X^2$, $X^3$, $X^4$, $X^5$, $X^6$, $X^7$, $X^8$ and $X^9$ are each independently selected from the group consisting of hydrogen, halogen, cyano, nitro, [C₁-C₃]-alkyl, [C₁-C₃]-haloalkyl, [C₁-C₃]-alkoxy-[C₁-C₃]-alkyl, —OR³, —C(=O)OR³, —N(R⁴)S(=O)₂R⁵, —S(=O)₂NR³R⁵, —N(R⁴)C(=O)OR³, —CR⁴=NOR³, —CH₂ON=C(CN)₂, NR⁴C(=O)R⁵, non-substituted or substituted phenyl and non-substituted or substituted pyridyl, wherein the substituent is selected from the group consisting of halogen, cyano, nitro, [C₁-C₃]-alkyl, [C₁-

$C_3$]-haloalkyl, [$C_1$-$C_3$]-alkoxy, [$C_1$-$C_3$]-haloalkoxy, [$C_1$-$C_3$]-alkylthio and [$C_1$-$C_3$]-haloalkylthio;

Z is selected from the group consisting of hydrogen, [$C_1$-$C_3$]-alkyl, [$C_1$-$C_3$]-haloalkyl, phenylmethyl, —C(=O)$R^3$ and —C(=O)O$R^3$;

K is selected from the group consisting of oxygen and sulfur;

$R^3$ is selected from the group consisting of hydrogen, [$C_1$-$C_3$]-alkyl, [$C_1$-$C_3$]-haloalkyl, [$C_1$-$C_3$]-alkoxycarbonyl, non-substituted or substituted phenyl and non-substituted or substituted pyridyl, wherein the substituent is selected from the group consisting of halogen, cyano, nitro, [$C_1$-$C_3$]-alkyl, [$C_1$-$C_3$]-haloalkyl, [$C_1$-$C_3$]-alkoxy, [$C_1$-$C_3$]-haloalkoxy, [$C_1$-$C_3$]-alkylthio and [$C_1$-$C_3$]haloalkylthio;

$R^4$ and $R^5$ are each independently selected from the group consisting of hydrogen, [$C_1$-$C_3$]-alkyl, [$C_1$-$C_3$]-haloalkyl, [$C_1$-$C_3$]-alkoxy, [$C_1$-$C_3$]-haloalkoxy, [$C_1$-$C_3$]-alkoxycarbonyl, non-substituted or substituted phenyl group and non-substituted or substituted pyridyl group, where the substituent group is selected from the group consisting of halogen, cyano, nitro, [$C_1$-$C_3$]-alkyl, [$C_1$-$C_3$]-haloalkyl, [$C_1$-$C_3$]-alkoxy, [$C_1$-$C_3$]-haloalkoxy, [$C_1$-$C_3$]-alkylthio and [$C_1$-$C_3$]-haloalkylthio;

Q is selected from the group consisting of $Q^{1-10}$, non-substituted or substituted phenyl group and non-substituted or substituted pyridyl group, wherein the substituent is selected from the group consisting of halogen, cyano, nitro, hydroxyl, mercapto, amino, $CONH_2$, COOH, CHO, [$C_1$-$C_3$]-alkyl, [$C_1$-$C_3$] haloalkyl, [$C_3$-$C_6$]-cycloalkyl, [$C_1$-$C_3$]-alkoxy, [$C_1$-$C_3$] haloalkoxy, [$C_1$-$C_3$]-alkylthio, [$C_1$-$C_3$]haloalkyl, [$C_1$-$C_3$]-alkylamino, [$C_1$-$C_3$]-dialkylamino, [$C_3$-$C_6$]-cycloalkylamino, [$C_1$-$C_3$]-alkoxycarbonyl, [$C_1$-$C_3$]-alkylsulfonyl, [$C_1$-$C_3$]alkylaminocarbonyl and [$C_1$-$C_3$]-alkylaminosulfonyl;

T is selected from the group consisting of cyano, [$C_1$-$C_3$]-alkyl, [$C_1$-$C_3$]-haloalkyl, [$C_3$-$C_6$]-cycloalkyl, non-substituted or substituted phenyl and non-substituted or substituted pyridyl, wherein the substituent is selected from the group consisting of halogen, cyano, nitro, [$C_1$-$C_3$]-alkyl, [$C_1$-$C_3$]-haloalkyl, [$C_3$-$C_6$]-cycloalkyl, [$C_1$-$C_3$]-alkoxy, [$C_1$-$C_3$]haloalkoxy, [$C_1$-$C_3$]-alkylthio, [$C_1$-$C_3$]-alkylthio, [$C_1$-$C_3$]-alkylamino, [$C_1$-$C_3$]-dialkylamino, [$C_3$-$C_6$]-cycloalkylamino, [$C_1$-$C_3$]-alkoxycarbonyl, [$C_1$-$C_3$]-alkylsulfonyl, [$C_1$-$C_3$]-alkylaminocarbonyl and [$C_1$-$C_3$]-alkylaminosulfonyl.

5. The compound according to claim 4, wherein

L is selected from the group consisting of —($CR^1R^2$)$_n$—, —($CR^1R^2$)$_m$—NH—(C=O)—$CH_2$—($CR^1R^2$)$_p$—, —($CR^1R^2$)$_m$—O—$CH_2$—($CR^1R^2$)$_p$— and —($CR^1R^2$)$_m$—S—$CH_2$—($CR^1R^2$)$_p$—;

n represents 1 or 2;
m represents 0 or 1;
p represents 0, 1 or 2;
$R^1$, $R^2$ are selected from hydrogen;

W is selected from the group consisting of $W^1$, $W^2$, $W^3$, $W^4$, $W^{12}$, $W^{16}$, $W^{18}$, $W^{21}$, $W^{23}$, $W^{48}$, $W^{49}$, $W^{67}$, $W^{69}$, $W^{70}$, $W^{71}$, $W^{72}$, $W^{73}$, $W^{74}$, $W^{75}$, $W^{76}$, $W^{77}$, $W^{78}$, $W^{79}$, $W^{80}$, $W^{81}$, $W^{82}$, $W^{83}$ and $W^{84}$;

$X^1$, $X^2$, $X^3$, $X^4$, $X^5$, $X^6$, $X^7$, $X^8$ and $X^9$ are each independently selected from the group consisting of hydrogen, halogen, cyano, nitro, [$C_1$-$C_3$]-alkyl, [$C_1$-$C_3$]-haloalkyl, [$C_1$-$C_3$]-alkoxy, [$C_1$-$C_3$]-alkyl, —O$R^3$, —C(=O)O$R^3$, —N($R^4$)S(=O)$_2R^5$, —S(=O)$_2NR^3R^5$, —N($R^4$)C(=O)O$R^3$, —$CR^4$=NO$R^3$, —$CH_2$ON=C(CN)$_2$, N$R^4$C(=O)$R^5$, non-substituted or substituted phenyl and non-substituted or substituted pyridyl, wherein the substituent group is selected in from the group consisting of halogen, cyano, nitro, [$C_1$-$C_3$]-alkyl, and [$C_1$-$C_3$]-haloalkyl, [$C_1$-$C_3$]-alkoxy, and [$C_1$-$C_3$]-haloalkoxy;

Z is selected from the group consisting of hydrogen, methyl, phenylmethyl, —C(=O)$R^3$ and —C(=O)O$R^3$;

K is oxygen;

$R^3$ is selected from the group consisting of hydrogen, [$C_1$-$C_3$]-alkyl, [$C_1$-$C_3$]-haloalkyl, [$C_1$-$C_3$]-alkoxycarbonyl, non-substituted or substituted phenyl and non-substituted or substituted pyridyl, wherein the substituent group is selected from the group consisting of halogen, cyano, nitro, [$C_1$-$C_3$]-alkyl, [$C_1$-$C_3$]-haloalkyl, [$C_1$-$C_3$]-alkoxy, [$C_1$-$C_3$]-haloalkoxy, [$C_1$-$C_3$]-alkylthio and [$C_1$-$C_3$]-haloalkylthio;

$R^4$ and $R^5$ are each independently selected from the group consisting of hydrogen, [$C_1$-$C_3$]-alkyl, [$C_1$-$C_3$]-haloalkyl, [$C_1$-$C_3$]-alkoxy, [$C_1$-$C_3$]-haloalkoxy, [$C_1$-$C_3$]-alkoxycarbonyl, a non-substituted or substituted phenyl and non-substituted or substituted pyridyl, wherein the substituent is selected from the group consisting of halogen, cyano, nitro, [$C_1$-$C_3$]-alkyl, [$C_1$-$C_3$]-haloalkyl, [$C_1$-$C_3$]-alkoxy, [$C_1$-$C_3$]-haloalkoxy, [$C_1$-$C_3$]-alkylthio and [$C_1$-$C_3$]-haloalkylthio;

Q is selected from the group consisting of $Q^{1-10}$, non-substituted or substituted phenyl group and non-substituted or substituted pyridyl, wherein the substituent is selected from the group consisting of halogen, cyano, nitro, hydroxyl, mercapto, amino, $CONH_2$, COOH, CHO, [$C_1$-$C_3$]-alkyl, [$C_1$-$C_3$]-haloalkyl, [$C_3$-$C_6$]-cycloalkyl, [$C_1$-$C_3$]-alkoxy, [$C_1$-$C_3$]-haloalkoxy, [$C_1$-$C_3$]-alkylthio, [$C_1$-$C_3$] haloalkylthio, [$C_1$-$C_3$]-alkylamino, [$C_1$-$C_3$]-dialkylamino, [$C_3$-$C_6$]-cycloalkylamino, [$C_1$-$C_3$]-alkyloxycarbonyl, [$C_1$-$C_3$]-alkylsulfonyl, [$C_1$-$C_3$]-alkylaminocarbonyl and [$C_1$-$C_3$]-alkylaminosulfonyl;

T is selected consisting of cyano, [$C_1$-$C_3$]-alkyl, [$C_1$-$C_3$]-haloalkyl, [$C_3$-$C_6$]-cycloalkyl, a non-substituted or substituted phenyl group and non-substituted or substituted pyridyl group, where the substituent is selected from the group consisting of halogen, cyano, nitro, [$C_1$-$C_3$]-alkyl, [$C_1$-$C_3$]-haloalkyl, [$C_3$-$C_6$]-cycloalkyl, [$C_1$-$C_3$]-alkoxy, [$C_1$-$C_3$]-haloalkoxy, [$C_1$-$C_3$]alkylthio, and [$C_1$-$C_3$]-haloalkylthio.

6. The compound according to claim 5, wherein

L is selected from the group consisting of —($CR^1R^2$)$_n$—, —($CR^1R^2$)$_m$—NH—(C=O)—$CH_2$—($CR^1R^2$)$_p$—, —($CR^1R^2$)$_m$—O—$CH_2$—($CR^1R^2$)$_p$— and —($CR^1R^2$)$_m$—S—$CH_2$—($CR^1R^2$)$_p$—;

n represents 1 or 2;
m represents 0;
p represents 0 or 1;
$R^1$ and $R^2$ are each hydrogen; and W is selected from the group consisting of $W^1$, $W^2$, $W^3$, $W^4$, $W^{12}$, $W^{16}$, $W^{18}$, $W^{21}$, $W^{23}$, $W^{48}$, $W^{49}$, $W^{67}$, $W^{68}$, $W^{69}$, $W^{70}$, $W^{71}$, $W^{72}$, $W^{74}$, $W^{79}$, $W^{80}$, $W^{81}$, $W^{82}$ and $W^{83}$;

$X^1$, $X^2$, $X^3$, $X^4$, $X^5$, $X^6$, $X^7$, $X^8$, and $X^9$ are each independently selected from the group consisting of hydrogen, fluorine, chlorine, bromine, cyano, nitro, methyl, ethyl, isopropyl, chloromethyl, bromomethyl, difluoromethyl, trifluoromethyl, heptafluoroisopropyl, —O$R^3$, —C(=O)O$R^3$, —N($R^4$)S(=O)$_2R^5$, —S(=O)$_2$ N$R^3R^4$, —N($R^4$)C(=O)O$R^3$, —$CR^4$=NO$R^3$, —$CH_2$ON=C(CN)$_2$, N$R^4$C(=O)$R^5$, non-substituted or substituted phenyl group and non-substituted or substituted pyridyl group, wherein the substituent group is selected from the group consisting of halogen, cyano, nitro, trifluoromethyl, heptafluoropropyl, heptafluoroisopropyl, methoxy, and trifluoromethoxy;
Z is selected from the group consisting of hydrogen, methyl, and phenylmethyl;
K is oxygen;
$R^3$ is selected from the group consisting of hydrogen, methyl, ethyl, propyl, isopropyl, cyclopropyl, difluoromethyl, trifluoromethyl, heptafluoropropyl, heptafluoroisopropyl, methoxycarbonyl, non-substituted or substituted phenyl and non-substituted or substituted pyridyl, wherein the substituent group is selected from the group consisting of halogen, cyano, nitro, and trifluoromethyl;
$R^4$, $R^5$ are each independently selected from the group consisting of hydrogen, methyl, ethyl, propyl, isopropyl, cyclopropyl, difluoromethyl, trifluoromethyl, heptafluoropropyl, heptafluoroisopropyl, methoxy, trifluoromethoxy, methoxycarbonyl, non-substituted or substituted phenyl and non-substituted or substituted pyridyl, wherein the substituent group is selected from the group consisting of halogen, cyano, nitro, methyl, ethyl, propyl, chloromethyl, bromomethyl, trifluoromethyl, heptafluoroisopropyl, methoxy, and trifluoromethoxy;
Q is selected from the group consisting of $Q^{1-10}$, non-unsubstituted or substituted phenyl and non-substituted or substituted pyridyl, wherein the substituent is selected from the group consisting of halogen, cyano, nitro, hydroxyl, mercapto, amino, $[C_1-C_3]$-haloalkyl, $[C_1-C_3]$-alkoxy, $[C_1-C_3]$ haloalkoxy, $[C_1-C_3]$-alkylthio, and $[C_1-C_3]$-haloalkylthio;
T is selected from the group consisting of cyano, $[C_1-C_3]$-alkyl group, $[C_1-C_3]$-haloalkyl, $[C_3-C_6]$-cycloalkyl group, non-substituted or substituted phenyl and non-substituted or substituted pyridyl, wherein the substituent group is selected from the group consisting of halogen, cyano, nitro, $[C_1-C_3]$-alkyl, $[C_1-C_3]$-haloalkyl, $[C_3-C_6]$-cycloalkyl, $[C_1-C_3]$-alkoxy, $[C_1-C_3]$-haloalkoxy, $[C_1-C_3]$-alkylthio, and $[C_1-C_3]$-alkylthio.

7. The compound according to claim 6, wherein, L is selected from —$CH_2$—, —$CH_2$—$CH_2$—, —NH—(C=O)—$CH_2$— or —O—$CH_2$—$CH_2$—; W is selected from the group consisting of $W^1$, $W^2$, $W^3$, $W^4$, $W^{12}$, $W^{16}$, $W^{18}$, $W^{21}$, $W^{23}$, $W^{48}$, $W^{49}$, $W^{67}$, $W^{68}$, $W^{69}$, $W^{70}$, $W^{71}$, $W^{72}$, $W^{74}$, $W^{79}$, $W^{80}$, $W^{81}$, $W^{82}$ and $W^{83}$;
$X^1$, $X^2$, $X^3$, $X^4$, $X^5$, $X^6$, $X^7$, $X^8$, and $X^9$ are each independent selected from the group consisting of hydrogen, fluorine, chlorine, bromine, cyano, nitro, methyl, ethyl, isopropyl, chloromethyl, bromomethyl, difluoromethyl, trifluoromethyl, heptafluoroisopropyl, —$OR^3$, —C(=O)$OR^3$, —N($R^4$)S(=O)$_2R^5$, —S(=O)$_2NR^3R^4$, —N($R^4$)C(=O)$OR^3$, —$CR^4$=$NOR^3$, —$CH_2ON$=C(CN)$_2$, $NR^4C$(=O)$R^5$, non-substituted or substituted phenyl and non-substituted or substituted pyridyl, wherein the substituent is selected from the group consisting of halogen, cyano, nitro, trifluoromethyl, heptafluoropropyl, heptafluoroisopropyl, methoxy, trifluoromethoxy; Z is selected from the group consisting of hydrogen, methyl, phenylmethyl; K is oxygen; $R^3$ is selected from the group consisting of hydrogen, methyl, ethyl, propyl, isopropyl, cyclopropyl, difluoromethyl, non-substituted or substituted phenyl and non-substituted or substituted pyridyl, wherein the substituent is selected from the group consisting of halogen, cyano, nitro, trifluoromethyl; $R^4$ and $R^5$ are each independently selected from the group consisting of hydrogen, methyl, ethyl, propyl, isopropyl, cyclopropyl, difluoromethyl, trifluoromethyl, heptafluoropropyl, heptafluoroisopropyl, methoxy, trifluoromethoxy, methoxycarbonyl, non-substituted or substituted phenyl and non-substituted or substituted pyridyl, wherein the substituent is selected from the group consisting of halogen, cyano, nitro, methyl, ethyl, propyl, chloromethyl, bromomethyl, trifluoromethyl, heptafluoroisopropyl, methoxy, trifluoromethoxy;
Q is selected from the group consisting of $Q^{1-10}$, non-substituted or substituted phenyl and non-substituted or substituted pyridyl, wherein the substituent is selected from the group consisting of halogen, cyano, nitro, hydroxyl, mercapto, amino, chloromethyl, bromomethyl, difluoromethyl, trifluoromethyl, heptafluoroisopropyl, methoxy, ethoxy, propoxy, isopropoxy, trifluoromethoxy, methylthio, ethylthio, trifluoromethylthio, and trifluoroethylthio;
T is selected from the group consisting of cyano, methyl, ethyl, propyl, isopropyl, cyclopropyl, trifluoroethyl, difluoroethyl, cyclopropyl, cyclobutanyl, a cyclopentyl, cyclohexyl, non-substituted or substituted phenyl group and non-substituted or substituted pyridyl, wherein the substituent is selected from the group consisting of halogen, cyano, nitro, methyl, ethyl, propyl, isopropyl, chloromethyl, bromomethyl, trifluoromethyl, heptafluoroisopropyl, cyclopropyl, cyclobutanyl, cyclopentyl, cyclohexyl, methoxy, ethoxy, propoxy, isopropoxy, trifluoromethoxy, methylthio, ethylthio, trifluoromethylthio, and trifluoroethylthio; when L represents —$CH_2$—, W is not benzene.

8. The compound according to claim 7, wherein, L is selected from the group consisting of —$CH_2$—, —$CH_2$—$CH_2$—, —NH—(C=O)—$CH_2$— and —O—$CH_2$—$CH_2$—; W is selected from the group consisting of $W^1$, $W^2$, $W^3$ and $W^4$; $X^1$, $X^2$, $X^3$, $X^4$, $X^5$, $X^6$, $X^7$, $X^8$, and $X^9$ are each independently selected from the group consisting of hydrogen, fluorine, chlorine, bromine, cyano, nitro, methyl, ethyl, isopropyl, chloromethyl, bromomethyl, difluoromethyl, trifluoromethyl, heptafluoroisopropyl, —$OR^3$, —C(=O)$OR^3$, —N($R^4$)S(=O)$_2R^5$, —S(=O)$_2NR^3R^4$, —N($R^4$)C(=O)$OR^3$, —$CR^4$=$NOR^3$, —$CH_2ON$=C(CN)$_2$, $NR^4C$(=O)$R^5$, non-substituted or substituted phenyl group and non-substituted or substituted pyridyl group wherein the substituent group is selected from the group consisting of halogen, cyano, nitro, trifluoromethyl, heptafluoropropyl, heptafluoroisopropyl, methoxy, trifluoromethoxy; $R^3$ is selected from the group consisting of hydrogen, methyl, ethyl, propyl, isopropyl, and cyclopropyl, difluoromethyl, trifluoromethyl, heptafluoropropyl, heptafluoroisopropyl, methoxycarbonyl, non-substituted or substituted phenyl group and non-substituted or substituted pyridyl group, wherein the substituent group is selected from the group consisting of halogen, cyano, nitro, and trifluoromethyl; $R^4$, $R^5$ are each independently selected from the group consisting of hydrogen, methyl, ethyl, propyl, isopropyl, cyclopropyl, difluoromethyl, trifluoromethyl, heptafluoropropyl, heptafluoroisopropyl, methoxy, triflouromethoxy, methoxycarbonyl, non-substituted or substituent phenyl and non-substituted or substituent pyridyl, wherein the substituent group is selected from the group consisting of halogen, cyano, nitro, methyl, ethyl, and propyl, chloromethyl, bromomethyl, trifluoromethyl, heptafluoroisopropyl, methoxy and trifluoromethoxy.

9. The compound according to claim 7, wherein L is selected from the group consisting of —CH$_2$—, —CH$_2$—CH$_2$—, —NH—(C=O)—CH$_2$— and —O—CH$_2$—CH$_2$—; W is selected from the group consisting of W$^{12}$, W$^{16}$, W$^{18}$, W$^{23}$, W$^{49}$, W$^{67}$, W$^{68}$, W$^{69}$ and W$^{82}$; X$^1$, X$^2$, X$^3$, X$^4$, X$^5$, X$^6$, X$^7$, X$^8$, and X$^9$ are each independently selected from the group consisting of hydrogen, fluorine, chlorine, bromine, cyano, nitro, methyl, ethyl, isopropyl, chloromethyl, bromomethyl, difluoromethyl, trifluoromethyl, heptafluoroisopropyl, —OR$^3$, —C(=O)OR$^3$, —N(R$^4$)S(=O)$_2$R$^5$, —S(=O)$_2$NR$^3$R$^4$, —N(R$^4$)C(=O)OR$^3$, —CR$^4$=NOR$^3$, —CH$_2$ON=C(CN)$_2$, NR$^4$C(=O)R$^5$, non-substituted or substituted phenyl and non-substituted or substituted pyridyl, wherein the substituent group is selected from the group consisting of halogen, cyano, nitro, trifluoromethyl, heptafluoropropyl, heptafluoroisopropyl, methoxy, and trifluoromethoxy; Z is selected from the group consisting of hydrogen, methyl, and phenylmethyl; K is oxygen; R$^3$ is selected from the group consisting of hydrogen, methyl, ethyl, propyl, isopropyl, cyclopropyl, difluoromethyl, trifluoromethyl, heptafluoropropyl, heptafluoroisopropyl, methoxycarbonyl, non-substituted or substituted phenyl group and non-substituted or substituted pyridyl group, wherein substituent group is selected from the group consisting of halogen, cyano group, nitro group and trifluoromethyl; and R$^4$ and R$^5$ are each independently selected from the group consisting of hydrogen and methyl groups, Ethyl, propyl, isopropyl, cyclopropyl, difluoromethyl, trifluoromethyl, heptafluoropropyl, heptafluoroisopropyl, methoxy, trifluoromethoxy, methoxycarbonyl, non-substituted or substituted phenyl group and non-substituted or substituted pyridyl group, wherein the substituent group is selected from the group consisting of halogen, cyano, nitro, methyl, ethyl, propyl, chloromethyl, bromomethyl, trifluoromethyl, heptafluoroisopropyl, methoxy, and trifluoromethoxy.

10. The compound according to claim 7, wherein L is selected from the group consisting of —CH$_2$—, —CH$_2$—CH$_2$—, —NH—(C=O)—CH$_2$— and —O—CH$_2$—CH$_2$—; W is selected from the group consisting of W$^{21}$, W$^{48}$, W$^{70}$, W$^{71}$, W$^{72}$, W$^{74}$, W$^{79}$, W$^{80}$, W$^{81}$ and W$^{83}$; and X$^1$, X$^2$, X$^3$, X$^4$, X$^5$, X$^6$, X$^7$, X$^8$, and X$^9$ are each independently selected from the group consisting of hydrogen, fluorine, chlorine, bromine, cyano, nitro, methyl, ethyl, isopropyl, chloromethyl, bromomethyl, difluoromethyl, trifluoromethyl, heptafluoroisopropyl, methoxy, and trifluoromethoxy; Z is hydrogen or methyl; K is oxygen; Q is selected from the group consisting of Q$^{1-10}$, non-substituted or substituted phenyl group and a non-substituted or substituted pyridyl group wherein a substituent group is selected from the group consisting of halogen, cyano, nitro, hydroxyl, mercapto, amino, chloromethyl, bromomethyl, difluoromethyl Base, trifluoromethyl, heptafluoroisopropyl, methoxy, ethoxy, propoxy, isopropoxy, trifluoromethoxy, methylthio, ethylthio, trifluoromethylthio, or trifluoroethylthio; T is cyano, methyl, ethyl, propyl, isopropyl, cyclopropyl, trifluoroethyl, difluoroethyl, cyclopropyl, cyclobutane, cyclopentane, alkyl, a cyclohexane group, a phenyl group or a pyridyl group, unsubstituted or substituted by halogen, cyano, nitro, methyl, ethyl, propyl, Isopropyl, chloromethyl, bromomethyl, trifluoromethyl, heptafluoroisopropyl, cyclopropyl, cyclobutane, cyclopentyl, cyclohexane, methoxy, ethoxy, propoxy, isopropoxy, trifluoromethoxy, methylthio, ethylthio, trifluoromethylthio, trifluoroethylthio.

11. A fungicidal or bactericidal composition comprising an effective amount of the malonitrile oxime ether compound according to claim 1.

12. A fungicidal composition comprising the compound according to claim 1 and an acceptable carrier, wherein the weight percentage of the compound in the composition is 0.1-99%.

13. A method for controlling diseases of plants, comprising applying an effective quantity of a composition according to claim 12 to the said plants or to the soil where the said plants grow or are capable of growing.

* * * * *